(12) United States Patent
Terashita et al.

(10) Patent No.: US 6,974,806 B2
(45) Date of Patent: Dec. 13, 2005

(54) LIPID-RICH PLAQUE INHIBITORS

(75) Inventors: Zen-ichi Terashita, Toyonaka (JP); Masahira Nakamura, Kashiba (JP); Shogo Marui, Kobe (JP); Masaki Ogino, Nishinomiya (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 365 days.

(21) Appl. No.: 10/332,632

(22) PCT Filed: Jul. 13, 2001

(86) PCT No.: PCT/JP01/06070

§ 371 (c)(1),
(2), (4) Date: Jan. 10, 2003

(87) PCT Pub. No.: WO02/06264

PCT Pub. Date: Jan. 24, 2002

(65) Prior Publication Data

US 2003/0232809 A1 Dec. 18, 2003

(30) Foreign Application Priority Data

Jul. 13, 2000 (JP) ......................................... 2000-212611
Dec. 26, 2000 (JP) ......................................... 2000-395079

(51) Int. Cl.[7] ............................................. A61K 31/21
(52) U.S. Cl. ....................... 514/100; 549/200; 549/263; 549/265
(58) Field of Search ................................ 549/200, 263, 549/265; 514/100

(56) References Cited

FOREIGN PATENT DOCUMENTS

| EP | 0 305 028 A2 | 3/1989 |
|----|--------------|--------|
| EP | 0 585 913 A2 | 3/1994 |
| EP | 0 602 598 A1 | 6/1994 |
| EP | 0 613 894 A1 | 9/1994 |
| JP | 6263736 | 9/1994 |
| JP | 8295667 | 11/1996 |

*Primary Examiner*—James O. Wilsion
*Assistant Examiner*—Jason H. Johnsen
(74) *Attorney, Agent, or Firm*—Elaine M. Ramesh; Mark Chao

(57) ABSTRACT

The present invention provides a lipid-rich plaque regressing agent comprising a compound represented by Formula:

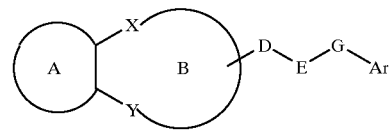

in which ring A is a cyclic hydrocarbon or the like; ring B is a heterocyclic ring or the like; each of X and Y is —NR[1]— (in which R[1] is a hydrocarbon or the like); D is a $C_{1-3}$ alkylene group or the like; E is —NH— or the like; G is a bond or the like; and Ar is an aryl or the like; D may be taken together with a constituent atom of the ring B to form a ring, and R[4] may be taken together with a constituent atom of the ring B to form a ring.

7 Claims, No Drawings

LIPID-RICH PLAQUE INHIBITORS

This application is the National Phase filing of International Patent Application No. PCT/JP01/06070, filed 13 Jul. 2001.

TECHNICAL FIELD

The present invention relates to a lipid-rich plaque regressing agent useful in preventing or treating acute coronary artery syndrome such as acute myocardial infarction, unstable angina and the like, peripheral artery occlusion and the like.

BACKGROUND ART

As an agent for reducing the level of blood cholesterol which causes arteriosclerosis, an agent which inhibits the absorption of bile acid by capturing it such as cholestyramine and cholestipol (U.S. Pat. No. 4,027,009), an agent which inhibits the absorption of cholesterol via an intestinal tract by inhibiting an acyl coenzyme A cholesterol acyl transferase (ACAT) such as melinamide (French Patent 1476569) and a cholesterol synthesis inhibitor, especially an agent which inhibits 3-hydroxy-3-methylglutaryl coenzyme A (HMG-CoA) reductase such as lovastatin (U.S. Pat. No. 4,231,938), simvastatin (U.S. Pat. No. 4,444,784) and pravastatin (U.S. Pat. No. 4,346,227) are employed in pharmaceuticals.

However, an HMG-CoA reductase inhibitor may cause a problem associated with side effects due to its inhibitory effect not only on cholesterol biosynthesis but also on a biologically essential component such as ubiquinone, dolichol and hem A.

Acute coronary artery syndrome (for example, unstable angina, acute myocardial infarction and ischemic sudden death) is caused by the destruction of a coronary artery plaque (atheroma) followed by the formation of a thrombus and the resultant plugging of the lumen of the coronary artery. Peripheral artery occlusion is caused by the destruction of an artery plaque (atheroma) followed by the formation of a thrombus and the resultant plugging of the lumen of a peripheral artery. These diseases are related closely with the characteristics of the plaque, and a lipid-rich plaque formed by the deposition of a macrophage retaining lipids such as cholesterol extensively onto an inner wall of a blood vessel is believed to cause acute coronary artery syndrome and peripheral artery occlusion.

Accordingly, the regression and removal of a lipid-rich plaque are very important for preventing or treating acute coronary artery syndrome such as acute myocardial infarction and unstable angina as well as peripheral artery occlusion. Also since a lipid-rich plaque is observed in a human whose blood cholesterol level is not high and a lipid-rich plaque once formed is difficult to be removed, an agent capable of regressing such a lipid-rich plaque efficiently has been desired. Since a lipid-rich plaque is observed in a human whose blood cholesterol level is not high, the ACAT inhibition to reduce the intestinal absorption of cholesterol is not considered to be sufficient for regressing and removing the lipid-rich plaque.

SUMMARY OF THE INVENTION

The present invention provides a lipid-rich plaque regressing agent useful in preventing or treating acute coronary artery syndrome such as acute myocardial infarction and unstable angina as well as peripheral artery occlusion.

The present invention also provides a lipid-rich plaque regressing agent which is migrated readily into a blood vessel or tissue to act directly on a macrophage in which lipids such as cholesterol are retained extensively whereby exerting a direct regressing effect on an arteriosclerotic focus.

In consideration of the above, we studied intensively and, as a result, we found out that an ACAT inhibitor having a certain structure has an unexpectedly high lipid-rich plaque regressing effect, which is sufficiently effective even at a concentration which does not affect the blood cholesterol level, and thereby completed the present invention.

Thus, the present invention relates to:

(1) a lipid-rich plaque regressing agent comprising a compound represented by Formula [I]:

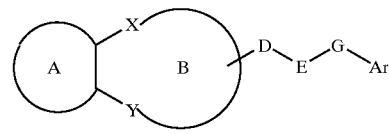

in which ring A is an optionally substituted cyclic hydrocarbon or an optionally substituted heterocyclic ring; ring B is a 5- or 6-membered homocyclic or heterocyclic ring; each of X and Y is —NR$^1$— (in which R$^1$ is a hydrogen atom, optionally substituted hydrocarbon group, optionally substituted hydroxyl group or optionally substituted amino group), —O—, —S—, —CO—, —CS—, —C(R$^2$)R$^{2a}$— (in which each of R$^2$ and R$^{2a}$ is a hydrogen atom, optionally substituted hydroxyl group or optionally substituted hydrocarbon group), —N= or =CR$^3$— (in which R$^3$ is a hydrogen atom, halogen atom, optionally substituted hydrocarbon group, optionally substituted hydroxyl group or a mercapto group which may be substituted by an optionally substituted hydrocarbon group); D is a C$_{1-3}$ alkylene group which may be substituted by an oxo group or thioxo group, —NH— or —CH$_2$NH—; E is —NR$^4$— (in which R$^4$ is a hydrogen atom or optionally substituted hydrocarbon group), —O—, —S(O)n- (n is 0, 1 or 2) or —CONR$^5$— (in which R$^5$ is a hydrogen atom or optionally substituted hydrocarbon group); G is a bond or C$_{1-3}$ alkylene group; Ar is an optionally substituted aryl group or optionally substituted heterocyclic group, D may be taken together with a constituent atom in the ring B to form a 5- to 7-membered ring which may be substituted by an oxo group or thioxo group, R$^4$ may be taken together with a constituent atom of the ring B to form a 5- to 7-membered ring which may be substituted by an oxo group or thioxo group, and the ring B may have a further substituent in addition to -D-E-G-Ar or a salt thereof;

(2) the lipid-rich plaque regressing agent according to the above-mentioned (1) comprising a compound represented by Formula [II]:

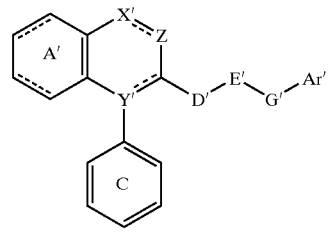

in which ring A' is an optionally substituted 6-membered cyclic hydrocarbon group; ring C is an optionally substituted benzene ring; one of X' and Z is —NR$^{1'}$— (in which R$^{1'}$ is a hydrogen atom, optionally substituted hydrocarbon group or optionally substituted amino group), —O— or —S— and the other is —CO—, —CS— or —C(R$^{2'}$)R$^{2a'}$— (in which each of R$^{2'}$ and R$^{2a'}$ is a hydrogen atom or optionally substituted hydrocarbon group), or one of them is —N═ and the other is ═CR$^{3'}$— (in which R$^{3'}$ is a hydrogen atom, halogen atom, optionally substituted hydrocarbon group, optionally substituted amino group, optionally substituted hydroxyl group or mercapto group which may be substituted by an optionally substituted hydrocarbon group); ═══ is a single bond or double bond; Y', when ═══ adjacent to Y' is a single bond, is

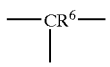

in which R$^6$ is a hydrogen atom, hydroxyl group or optionally substituted hydrocarbon group) or a nitrogen atom, Y', when ═══ adjacent to Y' is a double bond, is a carbon atom; D' is a C$_{1-3}$ alkylene group which may be substituted by an oxo group or thioxo group; E' is —NR$^7$— (in which R$^7$ is a hydrogen atom or optionally substituted hydrocarbon group), —O— or —S(O)n- (in which n is 0, 1 or 2); G' is a bond or C$_{1-3}$ alkylene group; Ar' is an optionally substituted aryl group or optionally substituted heterocyclic group, D' may be taken together with Z to form a 5- to 7-membered ring which may be substituted by an oxo group or thioxo group, R$^7$ may be taken together with Z to form a 5- to 7-membered ring which may be substituted by an oxo group or thioxo group or a salt thereof;

(3) the lipid-rich plaque regressing agent according to the above-mentioned (1) comprising a compound represented by Formula [III]:

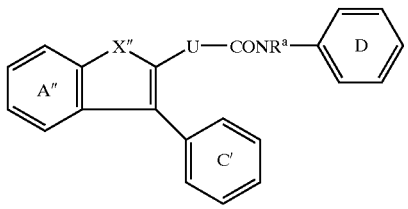

in which each of ring A", ring C' and ring D is an optionally substituted benzene ring, X" is —NR$^8$— (in which R$^8$ is a hydrogen atom or optionally substituted hydrocarbon group), —O— or —S—, U is —(CH$_2$)m-(in which m is 1 or 2) or —NH—, R$^a$ is a hydrogen atom or optionally substituted hydrocarbon group) or a salt thereof;

(4) the lipid-rich plaque regressing agent according to the above-mentioned (1) comprising a compound represented by Formula [IV]:

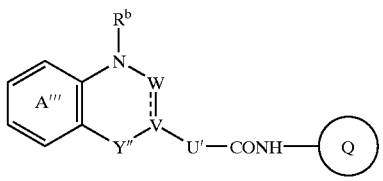

in which ring A''' is an optionally substituted benzene ring, Q is an optionally substituted aromatic ring, W is —CH$_2$—, —CO— or —CS—, V is

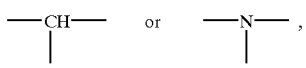

or W and V are taken together to form

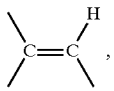

Y" is —CH$_2$—, —O—, —S—, —CO—, —CS— or —NR$^9$— (in which R$^9$ is a hydrogen atom or hydrocarbon group), U' is —NH—, —CH$_2$— or —CH$_2$NH—, R$^b$ is a hydrogen atom or optionally substituted hydrocarbon group, ═══ is a single bond or double bond or a salt thereof;

(5) the lipid-rich plaque regressing agent according to the above-mentioned (1) comprising a compound represented by Formula [V]:

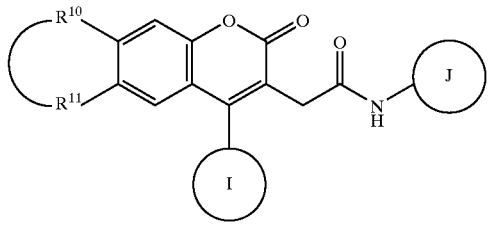

in which each of R$^{10}$ and R$^{11}$ is a hydrogen atom, halogen atom, optionally substituted linear hydrocarbon group or hydroxyl group which may be substituted by an optionally substituted linear hydrocarbon group, or the both may be taken together with the adjacent carbon atoms to form an optionally substituted cyclic hydrocarbon or a dihydrofuran ring which may be substituted by an oxo group, ring I is an optionally substituted benzene ring or optionally substituted pyridine ring (preferably optinally substituted with benzen ring), ring J is an optionally substituted benzene ring or optionally substituted pyridine ring or a salt thereof;

(6) the lipid-rich plaque regressing agent according to the above-mentioned (5) wherein each of R$^{10}$ and R$^{11}$ is a hydrogen atom, halogen atom or optionally substituted linear hydrocarbon group, or the both may be taken together with the adjacent carbon atoms to form an optionally substituted cyclic hydrocarbon;

(7) the lipid-rich plaque regressing agent according to the above-mentioned (1) comprising a compound represented by Formula [VI]:

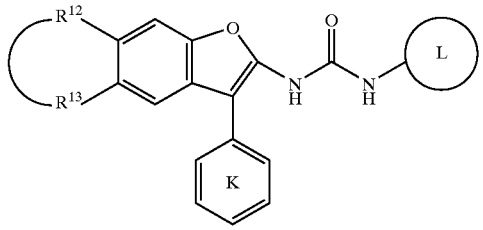

in which each of R$^{12}$ and R$^{13}$ is a hydrogen atom, halogen atom or optionally substituted linear hydrocarbon group, or the both may be taken together with the adjacent carbon atoms to form an optionally substituted cyclic hydrocarbon,

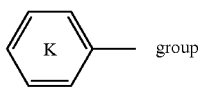 group is an optionally substituted phenyl group, ring L is an optionally substituted benzene ring or optionally substituted pyridine ring or a salt thereof;

(8) the lipid-rich plaque regressing agent according to the above-mentioned (1) which is a prophylactic and therapeutic agent against acute coronary artery syndrome;
(9) the lipid-rich plaque regressing agent according to the above-mentioned (1) which is a prophylactic and therapeutic agent against acute myocardial infarction;
(10) the lipid-rich plaque regressing agent according to the above-mentioned (1) which is a prophylactic and therapeutic agent against unstable angina;
(11) the lipid-rich plaque regressing agent according to the above-mentioned (1) which is a prophylactic and therapeutic agent against peripheral artery occlusion;
(12) a compound represented by Formula [V]:

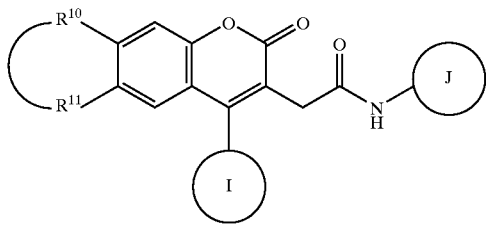

in which each of $R^{10}$ and $R^{11}$ is a hydrogen atom, halogen atom, optionally substituted linear hydrocarbon group or hydroxyl group which may be substituted by an optionally substituted linear hydrocarbon group, or the both may be taken together with the adjacent carbon atoms to form an optionally substituted cyclic hydrocarbon or a dihydrofuran ring which may be substituted by an oxo group, ring I is an optionally substituted benzene ring or optionally substituted pyridine ring (preferably optionally substituted benzene ring), ring J is an optionally substituted benzene ring or optionally substituted pyridine ring, provided that when $R^{10}$ is a hydrogen atom then $R^{11}$ is a substituted linear hydrocarbon group, or a salt thereof;

(13) the compound according to the above-mentioned (12) wherein each of $R^{10}$ and $R^{11}$ is a hydrogen atom, halogen atom or optionally substituted linear hydrocarbon group, or the both are taken together with the adjacent carbon atoms to form an optionally substituted cyclic hydrocarbon;
(14) the compound according to the above-mentioned (12) wherein each of $R^{10}$ and $R^{11}$ is a halogen atom or optionally substituted $C_{1-7}$ alkyl group;
(15) the compound according to the above-mentioned (12) wherein the cyclic hydrocarbon is a $C_{5-7}$ cyclic hydrocarbon;
(16) the compound according to the above-mentioned (12) wherein the ring J is a benzene ring substituted by halogenated alkyl group and/or halogen atom;
(17) the compound according to the above-mentioned (12) wherein the ring I is a benzene ring which may be substituted by alkyl group, halogenated alkyl group or halogen atom;

(18) a compound represented by Formula [VI]:

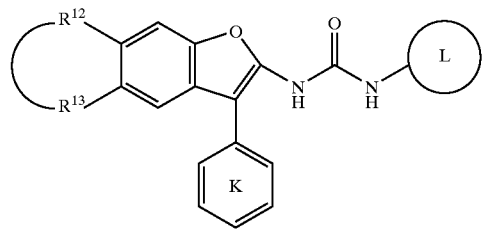

in which each of $R^{12}$ and $R^{13}$ is a hydrogen atom, halogen atom or optionally substituted linear hydrocarbon group, or the both may be taken together with the adjacent carbon atoms to form an optionally substituted cyclic hydrocarbon,

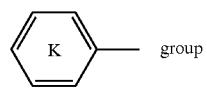 group is an optionally substituted phenyl group (provided that 2-chlorophenyl and 2-fluorophenyl are excluded), ring L is an optionally substituted benzene ring or optionally substituted pyridine ring, provided that when

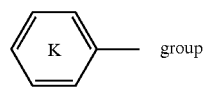 group is a phenyl group, then $R^{13}$ is not a methyl group, and when

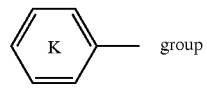 group is a 2-methylphenyl group, then $R^{13}$ is not a chlorine atom, or a salt thereof;
(19) the compound according to the above-mentioned (18) wherein each of $R^{12}$ and $R^{13}$ is a halogen atom or $C_{1-3}$ alkyl group;
(20) the compound according to the above-mentioned (18) wherein the cyclic hydrocarbon is a $C_{5-7}$ cyclic hydrocarbon;
(21) the compound according to the above-mentioned (18) wherein:

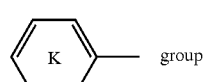 group is a phenyl group which may be substituted by a $C_{1-3}$ alkyl group;
(22) the compound according to the above-mentioned (18) wherein the ring L is a substituted benzene ring;
(23) 2-[7-Chloro-4-(3-chlorophenyl)-6-methyl-2-oxo-2H-chromen-3-yl]-N-[4-chloro-2-(trifluoromethyl)phenyl] acetamide; 2-[7-chloro-4-(3-chlorophenyl)-6-methyl-2-oxo-2H-chromen-3-yl]-N-[4-fluoro-2-(trifluoromethyl) phenyl]acetamide; 2-[7-chloro-4-(3-chloro-4-fluorophenyl)-6-methyl-2-oxo-2H-chromen-3-yl]-N-[4-chloro-2-(trifluoromethyl)phenyl]acetamide; 2-[7-chloro-4-(3-chloro-4-fluorophenyl)-6-methyl-2-oxo-2H-chromen-3-yl]-N-[4-fluoro-2-(trifluoromethyl)phenyl] acetamide; 2-[7-chloro-6-methyl-4-(3-methylphenyl)-2- oxo-2H-chromen-3-yl]-N-[4-chloro-2-(trifluoromethyl)phenyl]acetamide; 2-[7-chloro-6-methyl-4-(3-methylphenyl)-2-oxo-2H-chromen-3-yl]-N-[4-fluoro-2-(trifluoromethyl)phenyl]acetamide; 2-[7-chloro-2-oxo-4-phenyl-6-[(4-phenylpiperazin-1-yl)methyl]-2H-chromen-3-yl]-N-[4-chloro-2-(trifluoromethyl)phenyl]acetamide; 2-[7-chloro-2-oxo-4-phenyl-6-[(4-phenylpiperazin-1-yl)methyl]-2H-chromen-3-yl]-N-[4-fluoro-2-(trifluoromethyl)phenyl]acetamide; 2-[7-chloro-6-[[4-(4-chlorophenyl)-3,6-dihydropyridin-1(2H)-yl]methyl]-2-oxo-4-phenyl-2H-chromen-3-yl]-N-[4-chloro-2-(trifluoromethyl)phenyl]acetamide; 2-[7-chloro-6-[[4-(4-chlorophenyl)-3,6-dihydropyridin-1(2H)-yl]methyl]-2-oxo-4-phenyl-2H-chromen-3-yl]-N-[4-fluoro-2-(trifluoromethyl)phenyl]acetamide; 2-[7-chloro-6-[[4-(3-methylphenyl)piperidin-1-yl]methyl]-2-oxo-4-phenyl-2H-chromen-3-yl]-N-[4-chloro-2-(trifluoromethyl)phenyl]acetamide; 2-[7-chloro-6-[[4-(3-methylphenyl)piperidin-1-yl]methyl]-2-oxo-4-phenyl-2H-chromen-3-yl]-N-[4-fluoro-2-(trifluoromethyl)phenyl]acetamide; or a salt thereof;

(24) a prodrug of the compound according to any one of the above-mentioned (12), (18) and (23);

(25) a pharmaceutical composition comprising the compound according to any one of the above-mentioned (12), (18) and (23) or a prodrug thereof;

(26) an agent for inhibiting progression of an arteriosclerotic focus comprising a compound having a lipid-rich plaque regressing effect or a salt thereof;

(27) the agent according to the above-mentioned (26) in combination with an HMG-CoA reductase inhibitor.

(28) a method for producing the compound according to the above-mentioned (12) or a salt thereof, which comprises reacting a compound represented by Formula [VII]:

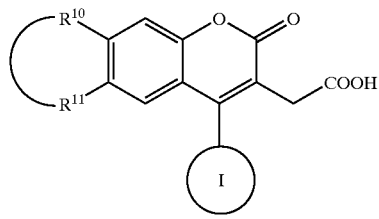

[in which each symbol is as defined in the above-mentioned (12)] or a salt thereof or a reactive derivative thereof with a compound represented by Formula [VIII]:

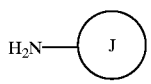

[in which each symbol is as defined in the above-mentioned (12)] or a salt thereof;

(29) a method for producing the compound according to the above-mentioned (18) or a salt thereof, which comprises reacting a compound represented by Formula [IX]:

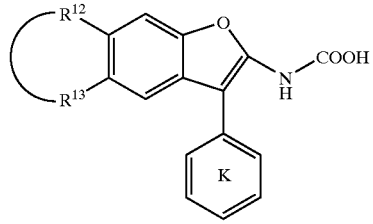

[in which each symbol is as defined in the above-mentioned (18)] or a salt thereof or a reactive derivative thereof with a compound represented by Formula [X]:

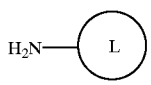

[in which each symbol is as defined in the above-mentioned (18)] or a salt thereof;

(30) a method for producing the compound according to the above-mentioned (18) or a salt thereof, which comprises reacting a compound represented by Formula [XI]:

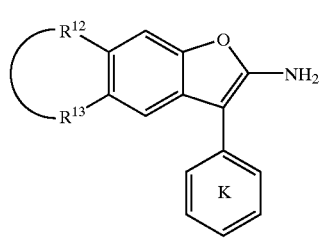

[in which each symbol is as defined in the above-mentioned (18)] or a salt thereof with a compound represented by Formula [XII]:

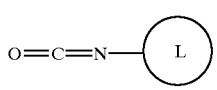

[in which each symbol is as defined in the above-mentioned (18)] or a salt thereof;

(31) a method for regressing a lipid-rich plaque in a mammal, which comprises administering an effective amount of the compound according to the above-mentioned (1) or a salt thereof to a mammal;

(32) a method for preventing and treating acute coronary artery syndrome in a mammal, which comprises administering an effective amount of a compound according to the above-mentioned (1) or a salt thereof to a mammal;

(33) a method for preventing and treating acute myocardial infarction in a mammal, which comprises administering an effective amount of the compound according to the above-mentioned (1) or a salt thereof to a mammal;

(34) a method for preventing and treating unstable angina in a mammal, which comprises administering an effective amount of the compound according to the above-mentioned (1) or a salt thereof to a mammal;

(35) a method for preventing and treating peripheral artery occlusion in a mammal, which comprises administering an effective amount of the compound according to the above-mentioned (1) or a salt thereof to a mammal;

(36) a method for regressing a lipid-rich plaque in a mammal, which comprises administering an effective amount of the compound according to the above-mentioned (12), a salt thereof or a prodrug thereof to a mammal;

(37) a method for regressing a lipid-rich plaque in a mammal, which comprises administering an effective amount of the compound according to the above-mentioned (18), a salt thereof or a prodrug thereof to a mammal;

(38) a use of the compound according to the above-mentioned (1) or a salt thereof for producing a lipid-rich plaque regressing agent;

(39) a use of the compound according to the above-mentioned (1) or a salt thereof for producing a prophylactic and therapeutic agent against acute coronary artery syndrome;

(40) a use of the compound according to the above-mentioned (1) or a salt thereof for producing a prophylactic and therapeutic agent against acute myocardial infarction;

(41) a use of the compound according to the above-mentioned (1) or a salt thereof for producing a prophylactic and therapeutic agent against unstable angina;

(42) a use of the compound according to the above-mentioned (1) or a salt thereof for producing a prophylactic and therapeutic agent against peripheral artery occlusion;

(43) a use of the compound according to the above-mentioned (12), a salt thereof or a prodrug thereof for producing a lipid-rich plaque regressing agent;

(44) a use of the compound according to the above-mentioned (18), a salt thereof or a prodrug thereof for producing a lipid-rich plaque regressing agent, and the like.

BEST MODE FOR CARRYING OUT THE INVENTION

In Formula [I] shown above, a cyclic hydrocarbon in an optionally substituted cyclic hydrocarbon represented by ring A may, for example, be a $C_{3-10}$ saturated hydrocarbon ring (e.g., cyclopropane ring, cyclobutane ring, cyclopentane ring, cyclohexane ring, cycloheptane ring and the like); $C_{5-8}$ unsaturated hydrocarbon ring (e.g., cyclopentene ring, cyclohexene ring, cycloheptene ring, benzene ring and the like). Among those listed above, a $C_{5-7}$ saturated hydrocarbon ring (e.g., cyclopentane ring, cyclohexane ring and the like), $C_{5-6}$ unsaturated hydrocarbon ring (e.g., cyclopentene ring, cyclohexene ring, benzene ring and the like) are preferred, with a benzene ring being especially preferred.

A substituent in an optionally substituted cyclic hydrocarbon described above may for example be:

(i) an optionally halogenated $C_{1-4}$ alkyl group (for example, methyl, chloromethyl, difluoromethyl, trichloromethyl, trifluoromethyl, ethyl, 2-bromoethyl, 2,2,2-trifluoroethyl, propyl, isopropyl, 3,3,3-trifluoropropyl, butyl and the like);

(ii) a $C_{1-4}$ alkyl group substituted by an amino group (for example, aminomethyl, 2-aminoethyl and the like);

(iii) a $C_{1-4}$ alkyl group substituted by a mono- or di-$C_{1-4}$ alkylamino group (for example, methylaminomethyl, dimethylaminomethyl, 2-methylaminoethyl, 2-dimethylaminoethyl and the like);

(iv) a $C_{1-4}$ alkyl group substituted by a carboxyl group (for example, carboxymethyl, carboxyethyl and the like);

(v) a $C_{1-4}$ alkyl group substituted by a $C_{1-4}$ alkoxy-carbonyl group (for example, methoxycarbonylethyl, ethoxycarbonylethyl and the like);

(vi) a $C_{1-4}$ alkyl group substituted by a hydroxyl group (for example, hydroxymethyl, hydroxyethyl and the like);

(vii) a $C_{1-4}$ alkyl group substituted by a $C_{1-4}$ alkoxy group which may be substituted by a $C_{1-4}$ alkoxy group or phenoxy group (for example, methoxymethyl, methoxyethyl, ethoxyethyl and the like);

(viii) a $C_{3-6}$ cycloalkyl group (for example, cyclopropyl, cyclobutyl, cyclopentyl, cyclohexyl and the like);

(ix) a halogen atom (for example, fluorine, chlorine, bromine, iodine and the like);

(x) a nitro group;

(xi) a cyano group;

(xii) a hydroxyl group;

(xiii) a $C_{1-4}$ alkoxy group which may be substituted by an optionally halogenated $C_{1-4}$ alkoxy group (for example, methoxy, difluoromethoxy, trifluoromethoxy, ethoxy, 2,2,2-trifluoroethoxy, propyloxy, butoxy, isopropyloxy and the like), $C_{1-4}$ alkoxy group or phenoxy group;

(xiv) a $C_{1-4}$ alkylthio group which may be substituted by an optionally halogenated $C_{1-4}$ alkylthio group (for example, methylthio, difluoromethylthio, trifluoromethylthio, ethylthio, propylthio, isopropylthio, butylthio and the like), $C_{1-4}$ alkoxy group or phenoxy group;

(xv) an amino group:

(xvi) a mono- or di-$C_{1-4}$ alkylamino group (for example, methylamino, ethylamino, propylamino, dimethylamino, diethylamino and the like);

(xvii) a cyclic amino group (for example, a 5- to 9-membered cyclic amino group which may contain 1 to 3 heteroatoms such as oxygen and sulfur atoms in addition to nitrogen atoms, specifically, pyrrolidinyl, piperidinyl, piperazinyl, morpholinyl and the like);

(xviii) a $C_{1-4}$ alkyl-carbonylamino group (for example, acetylamino, propionylamino, butyrylamino and the like);

(xix) an aminocarbonyloxy group;

(xx) a mono- or di-$C_{1-4}$ alkylamino-carbonyloxy group (for example, methylaminocarbonyloxy, ethylaminocarbonyloxy, dimethylaminocarbonyloxy, diethylaminocarbonyloxy and the like);

(xxi) a $C_{1-4}$ alkylsulfonylamino group (for example, methylsulfonylamino, ethylsulfonylamino, propylsulfonylamino and the like);

(xxii) a $C_{1-4}$ alkoxy-carbonyl group (for example, methoxycarbonyl, ethoxycarbonyl, propoxycarbonyl, isobutoxycarbonyl and the like);

(xxiii) a benzyloxycarbonyl group;

(xxiv) a carboxyl group;

(xxv) a $C_{1-6}$ alkyl-carbonyl group (for example, methylcarbonyl, ethylcarbonyl, butylcarbonyl and the like);

(xxvi) a $C_{3-6}$ cycloalkyl-carbonyl (for example, cyclohexylcarbonyl and the like);

(xxvii) a carbamoyl group;

(xxviii) a mono- or di-$C_{1-4}$ alkylcarbamoyl group (for example, methylcarbamoyl, ethylcarbamoyl, propylcarbamoyl, butylcarbamoyl, diethylcarbamoyl, dibutylcarbamoyl and the like), (xxix) a $C_{1-6}$ alkylsulfonyl group (for example, methylsulfonyl, ethylsulfonyl, propylsulfonyl and the like);

(xxx) a $C_{1-6}$ alkyl group substituted by [1] $C_{1-4}$ alkyl (e.g., methyl), [2] $C_{1-4}$ alkylsulfonyl (e.g., methylsulfonyl), [3], a $C_{6-12}$ aryl group which may have optionally halogenated $C_{1-4}$ alkyl (e.g., methyl, trifluoromethyl), halogen (e.g., fluorine, chlorine) or a hydroxyl group (for example, phenyl, naphthyl, hydroxyphenyl, methylphenyl, chlorophenyl and the like), [4] $C_{7-15}$ aralkyl (for example, benzyl), [5] $C_{1-4}$ alkoxy-$C_{1-4}$ alkyl (for example, propoxyethyl and the like), [6] a 5- to 9-membered heterocyclic group which contains 1 to 3 heteroatoms such as nitrogen, oxygen and sulfur atoms in addition to carbon atoms (for example, piperidinyl, piperazinyl, morpholinyl, thienyl, furyl, pyridyl, pyrimidinyl, thiazolyl, benzothiazolyl, benzoisothiazolyl, benzoxazolyl, benzoisoxazolyl and the like), [7] a cyclic amino group substituted by one or two substituents selected from hydroxyl, thiol, oxo, thioxo and the like (for example, a 5- to 9-membered cyclic amino group which may contain 1 to 3 heteroatoms such as oxygen and sulfur atoms in addition to nitrogen atoms, specifically, pyrrolidinyl, piperidinyl, piperazinyl, 3,6-dihydropyridin-1(2H)-yl, [1,3]thiazolo[4,5-b]pyridin-3(2H)-yl, morpholinyl), (for example, morpholinomethyl, 4-phenyl-1-piperazinylmethyl, 2-morpholinoethyl, 3-piperazinylpropyl, 4-methylsulfonyl-piperazinylmethyl, 4-benzyl-1-piperazinylmethyl, 4-(4-hydroxyphenyl)-1-piperazinylmethyl, 4-hydroxypiperidinylmethyl, 4-hydroxy-4-phenylpiperidinylmethyl, 4-phenylpiperidinylmethyl, 4-(2-pyridyl)-1-piperazinylmethyl, 4-(4-hydroxyphenyl)-1-piperazinylmethyl, (4-phenyl-3,6-dihydropyridin-1(2H)-yl)methyl and the like);

(xxxi) a $C_{1-4}$ alkyl group substituted by a $C_{1-6}$ alkyl-carbonyloxy group (for example, methylcarbonyloxy, ethylcarbonyloxy, butylcarbonyloxy and the like);

(xxxii) a $C_{1-4}$ alkyl group substituted by an amino group substituted by a 5- to 9-membered heterocyclic group which contains 1 to 3 heteroatoms such as nitrogen, oxygen and sulfur atoms in addition to carbon atoms (for example, thienyl, furyl, pyridyl, pyrimidinyl, thiazolyl, benzothiazolyl, benzoisothiazolyl, benzoxazolyl, benzoisoxazolyl and the like) (e.g., methyl(2-pyridyl)amino);

(xxxiii) a $C_{1-4}$ alkyl group substituted by an amino group substituted by $C_{1-4}$ alkyl and $C_{1-4}$ alkyl-carbonyl (e.g., methyl(methylcarbonyl)amino);

(xxxiv) a $C_{1-4}$ alkyl group substituted by an amino group substituted by $C_{1-4}$ alkyl and $C_{6-12}$ aryl-carbonyl (e.g., methyl(benzoyl)amino);

(xxxv) a $C_{1-4}$ alkyl group substituted by a $C_{1-6}$ alkyl-carbonyloxy group (for example, methylcarbonyloxy, ethylcarbonyloxy, butylcarbonyloxy and the like);

(xxxvi) a $C_{1-4}$ alkyl group substituted by a mono- or di-$C_{1-4}$ alkoxy-$C_{1-4}$-alkyl-amino group (e.g., butoxypropylamino);

(xxxvii) a $C_{1-4}$ alkyl group substituted by a 5- to 9-membered heterocyclic group which contains 1 to 3 heteroatoms such as nitrogen, oxygen and sulfur atoms in addition to carbon atoms (for example, thienyl, furyl, pyridyl, pyrimidinyl, thiazolyl, benzothiazolyl, benzoisothiazolyl, benzoxazolyl, benzoisoxazolyl and the like)-thio group (e.g., 2-pyridylthio);

(xxxviii) an oxo group;

(xxxix) a $C_{1-4}$ alkoxy-carbonyl $C_{2-6}$alkenyl group (e.g., methoxycarbonylvinyl and the like);

(xxxx) a $C_{2-6}$ alkenyl group substituted by a carboxyl group (e.g., carboxyvinyl and the like);

(xxxxi) a $C_{1-4}$ alkyl group substituted by a cyano group (e.g., cyanomethyl), and "an optionally substituted heterocyclic group" described below itself may also be employed as a substituent on said cyclic hydrocarbon. The same or difference 1 to 5, preferably 1 to 3 of these substituents may be in any substitutable positions.

Among those listed above, preferred substituents are (i) a halogen atom (for example, fluorine, chlorine, bromine and the like), (ii) an optionally halogenated $C_{1-4}$ alkyl group (for example, methyl, chloromethyl, difluoromethyl, trifluoromethyl, ethyl, propyl, isopropyl and the like), (iii) a $C_{3-6}$ cycloalkyl group (for example, cyclopropyl, cyclobutyl and the like), (iv) a hydroxyl group, (v) an optionally halogenated $C_{1-4}$ alkoxyl group (for example, methoxy, difluoromethoxy, trifluoromethoxy, ethoxy and the like), (vi) an optionally halogenated $C_{1-4}$ alkylthio group (for example, methylthio, trifluorothio, ethylthio and the like), (vii) an amino group, (viii) a mono- or di-$C_{1-4}$ alkylamino group (for example, methylamino, ethylamino, dimethylamino, diethylamino and the like), (ix) a $C_{1-4}$ alkoxy-carbonyl group (for example, methoxycarbonyl, ethoxycarbonyl and the like), (x) a $C_{1-6}$ alkyl group substituted by a cyclic amino group (for example, a 5- to 9-membered cyclic amino group which may contain 1 to 3 heteroatoms such as oxygen and sulfur atoms in addition to nitrogen atoms, specifically, pyrrolidinyl, piperidinyl, morpholinyl and the like) which may be substituted by a $C_{6-12}$ aryl group (for example, phenyl, naphthyl and the like), (for example, morpholinomethyl, 4-phenyl-1-piperazinylmethyl, 2-morpholinoethyl, 3-piperazinylpropyl and the like) and (xi) a carboxyl group and the like, with (i) a halogen atom (for example, fluoro, chloro and the like), (ii) a $C_{1-4}$ alkyl (for example, methyl, ethyl and the like), (iii) a $C_{3-6}$ cycloalkyl group (for example, cyclopropyl, cyclobutyl and the like), (iv) a hydroxyl group, (v) a $C_{1-4}$ alkoxy group (for example, methoxy, ethoxy and the like), (vi) a $C_{1-6}$ alkyl group substituted by a cyclic amino group (for example, a 5- to 9-membered cyclic amino group which may contain 1 to 3 heteroatoms such as oxygen and sulfur atoms in addition to nitrogen atoms, specifically, pyrrolidinyl, piperidinyl, piperazinyl, 3,6-dihydropyridin-1(2H)-yl, morpholinyl and the like) which may be substituted by a $C_{6-12}$ aryl group (for example, phenyl, naphthyl and the like), (for example, morpholinomethyl, 4-phenyl-1-piperazinylmethyl, 2-morpholinoethyl, (4-phenyl-3,6-dihydropyridin-1(2H)-ylmethyl), 3-piperazinylpropyl and the like) and (vii) a carboxyl group being especially preferred.

In Formula [I] shown above, a heterocyclic ring in an optionally substituted heterocyclic group represented by ring A may, for example, be a 5- to 9-membered, preferably 5- or 6-membered aromatic heterocyclic ring having 1 to 4, preferably 1 to 2 heteroatoms such as nitrogen, oxygen and sulfur atoms in addition to carbon atoms.

Such an aromatic heterocyclic group may, for example, be an aromatic monocyclic heterocyclic ring such as furan ring, thiophene ring, pyrrole ring, oxazoline ring, isoxazoline ring, thiazoline ring, isothiazoline ring, imidazole ring, pyrazole ring, 1,2,3-oxadiazole ring, 1,2,4-oxadiazole ring, 1,3,4-oxadiazole ring, 1,2,5-oxadiazole ring, 1,2,3-thiadiazole ring, 1,2,4-thiadiazole ring, 1,3,4-thiadiazole ring, 1,2,3-triazole ring, 1,2,4-triazole ring, tetrazole ring, pyridine ring, pyridazine ring, pyrimidine ring, pyrazine ring, triazine ring and the like. Among those listed above, furan ring, thiophene ring, pyrrole ring, oxazole ring, isoxazole ring, imidazole ring, pyrazole ring, 1,2,3-thiadiazole ring, 1,2,4-triazole ring, tetrazole ring, pyridine ring, pyridazine ring, thiazole ring and thiadiazoline ring are preferred, with furan ring, thiophene ring and pyridine ring being especially preferred.

A substituent which may be possessed by an optionally substituted heterocyclic group described above may, for example, be (i) an optionally halogenated $C_{1-4}$ alkyl group (for example, methyl, chloromethyl, difluoromethyl, trichloromethyl, trifluoromethyl, ethyl, 2,2-dibromoethyl, 2,2,2-trifluoroethyl, propyl, isopropyl, 3,3,3-trifluoropropyl, butyl and the like); (ii) a $C_{3-6}$ cycloalkyl group (for example, cyclopropyl, cyclobutyl, cyclopentyl, cyclohexyl and the like); (iii) a halogen atom (for example, fluorine, chlorine, bromine, iodine and the like); (iv) a nitro group; (v) a cyano group; (vi) a hydroxyl group; (vii) an optionally halogenated $C_{1-4}$ alkoxy group (for example, methoxy, fluoromethoxy, difluoromethoxy, trifluoromethoxy, ethoxy, 2,2,2-trifluoroethoxy, propyloxy, butyloxy, isopropyloxy and the like); (viii) an optionally halogenated $C_{1-4}$ alkylthio group (for example, methylthio, difluoromethylthio, trifluoromethylthio, ethylthio, propylthio, isopropylthio, butylthio and the like); (ix) an amino group; (x) a mono- or di-$C_{1-4}$ alkylamino group (for example, methylamino, ethylamino, propylamino, dimethylamino, diethylamino and the like); (xi) a cyclic amino group [for example, a 5- to 9-membered cyclic amino group which may contain 1 to 3 heteroatoms such as oxygen and sulfur atoms in addition to nitrogen atoms (for example, pyrrolidino, piperidino, morpholino and the like) and the like]; (xii) a $C_{1-4}$ alkyl-carbonylamino group (for example, acetylamino, propionylamino, butyrylamino and the like); (xiii) an aminocarbonyloxy group; (xiv) a mono- or di-$C_{1-4}$ alkylaminocarbonyloxy group (for example, methylaminocarbonyloxy, ethylaminocarbonyloxy, dimethylaminocarbonyloxy, diethylaminocarbonyloxy and the like); (xv) a $C_{1-4}$ alkylsulfonylamino group (for example, methylsulfonylamino, ethylsulfonylamino, propylsulfonylamino and the like); (xvi) a $C_{1-4}$ alkoxy-carbonyl group (for example, methoxycarbonyl, ethoxycarbonyl, propoxycarbonyl, isobutoxycarbonyl and the like); (xvii) a carboxyl group; (xviii) a $C_{1-6}$ alkyl-carbonyl group (for example, methylcarbonyl, ethylcarbonyl, butylcarbonyl and the like); (xix) a $C_{3-6}$ cycloalkylcarbonyl group (for example, cyclohexylcarbonyl and the like), (xx) a carbamoyl group; (xxi) a mono- or di-$C_{1-4}$ alkylcarbamoyl group (for example, methylcarbamoyl, ehtylcarbamoyl, propylcarbamoyl, butylcarbamoyl, diethylcarbamoyl, dibutylcarbamoyl and the like); (xxii) a $C_{1-6}$ alkylsulfonyl group (for example, methylsulfonyl, ethylsulfonyl, propylsulfonyl and the like); (xxiii) a $C_{3-6}$ cycloalkylsulfonyl (for example, cyclopentylsulfonyl, cyclohexylsulfonyl and the like), (xxiv) a $C_{6-10}$ aryl group (for example, phenyl, naphthyl and the like); (xxv) phenoxy, benzoyl, phenoxycarbonyl, phenyl-$C_{1-4}$ alkylcarbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsulfonylamino group [each phenyl group or naphtyl group may have in its any substitutable positions 1 to 3 substituents such as $C_{1-4}$ alkyl group (for example, methyl, ethyl, propyl, butyl, isopropyl and the like), $C_{1-4}$ alkoxy group (for example, methoxy, ethoxy, n-propyloxy, i-propyloxy, n-butyloxy and the like), halogen atom (for example, chloro, bromo, iodo and the like), hydroxyl group, benzyloxy group, amino group, mono- or di-$C_{1-4}$ alkylamino group (for example, methylamino, dimethylamino, ethylamino, diethylamino, diisopropylamino and the like), nitro group, $C_{1-6}$ alkylcarbonyl group (for example, 1-oxoethyl, 1-oxopropyl, 1-oxobutyl and the like) and the like]. The same or different 1 to 5, preferably 1 to 3 of these substituents may be in any substitutable positions.

Among those listed above, preferred substituents are (i) a halogen atom (for example, fluorine, chlorine, bromine and the like), (ii) an optionally halogenated $C_{1-4}$ alkyl group (for example, methyl, chloromethyl, difluoromethyl, trifluoromethyl, ethyl, propyl, isopropyl and the like), (iii) a $C_{3-6}$ cycloalkyl group (for example, cyclopropyl, cyclobutyl and the like), (iv) a hydroxyl group, (v) an optionally halogenated $C_{1-4}$ alkoxyl group (for example, methoxy, difluoromethoxy, trifluoromethoxy, ethoxy and the like), (vi) an optionally halogenated $C_{1-4}$ alkylthio group (for example, methylthio, trifluoromethylthio, ethylthio and the like), (vii) an amino group, (viii) a mono- or di-$C_{1-4}$ alkylamino group (for example, methylamino, ethylamino, dimethylamino, diethylamino and the like), (ix) a $C_{1-4}$ alkoxy-carbonyl group (for example, methoxycarbonyl, ethoxycarbonyl and the like) and (x) a carboxyl group and the like, with (i) a halogen atom (for example, fluoro, chloro and the like), (ii) a $C_{1-4}$ alkyl (for example, methyl, ethyl and the like), (iii) a $C_{3-6}$ cycloalkyl group (for example, cyclopropyl, cyclobutyl and the like), (iv) a hydroxyl group, (v) a $C_{1-4}$ alkoxy group (for example, methoxy, ethoxy and the like) and (vi) a carboxyl group being especially preferred.

In Formula [I] shown above, a 5- or 6-membered homocyclic ring represented by ring B may, for example, be a cyclopentane ring, cyclohexane ring, cyclopentene ring, cyclohexene ring, cyclopentadiene ring, cyclohexadiene ring, benzene ring and the like. Among those listed above, a cyclohexane ring, cyclohexene ring, cyclopentadiene ring and benzene ring are preferred, with a cyclohexane ring and cyclopentadiene ring being especially preferred.

In Formula [I] shown above, a 5- or 6-membered heterocyclic ring represented by ring B may, for example, be a 5- or 6-membered heterocyclic ring which contains 1 to 3 heteroatoms such as nitrogen, oxygen and sulfur atoms instead of 1 to 3 carbon atoms in the cyclopentane ring or cyclohexane ring (e.g., pyrrolidine ring, pyrroline ring, imidazolidine ring, imidazoline ring, pyrazolidine ring, pyrazoline ring, piperidine ring, piperazine ring, morpholine ring, thiomorpholine ring, dihydrofuran ring, tetrahydrofuran ring, α-pyrane ring, γ-pyrane ring, dihydropyrane ring, tetrahydropyrane ring, 1-thiacyclohexane ring, 1-thia-5-cyclohexene ring, 1-thia-3,5-cyclohexadiene ring and the like; a 5- or 6-membered aromatic heterocyclic ring (e.g., furan ring, thiophene ring, pyrrole ring, oxazoline ring, isoxazoline ring, thiazoline ring, isothiazoline ring, imidazole ring, pyrazole ring, 1,2,3-oxadiazole ring, 1,2,4-oxadiazole ring, 1,3,4-oxadiazole ring, 1,2,5-oxadiazole ring, 1,2,3-thiadiazole ring, 1,2,4-thiadiazole ring, 1,3,4-thiadiazole ring, 1,2,3-triazole ring, 1,2,4-triazole ring, tetrazole ring, pyridine ring, pyridazine ring, pyrimidine ring, pyrazine ring, triazine ring and the like). Among those listed above, a pyrrolidine ring, pyrroline ring, piperazine ring, morpholine ring, thiomorpholine ring, dihydrofuran ring, tetrahydrofuran ring, α-pyrane ring, γ-pyrane ring, dihydropyrane ring, furan ring, thiophene ring, pyrrole ring, oxazoline ring, isoxazoline ring, thiazoline ring, isothiazoline ring, imidazole ring, pyrazole ring, 1,2,3-oxadiazole ring, 1,2,4-oxadiazole ring, 1,3,4-oxadiazole ring, 1,2,5-oxadiazole ring, 1,2,3-thiadiazole ring, 1,2,4-thiadiazole ring, 1,3,4-thiadiazole ring, 1,2,3-triazole ring, 1,2,4-triazole ring are preferred, with an α-pyrane ring and furan ring being especially preferred.

When ring B has a further substituent in addition to -D-E-G-Ar-, then said substituent may, for example, be a group derivatized from an optionally substituted cyclic hydrocarbon or an optionally substituted heterocylic ring described above in addition to an oxo group and thioxo group. Among those listed above, (i) a group derived from a substituted cyclic hydrocarbon, (ii) an oxo group, (iii) a thioxo group are preferred, with an optionally substituted phenyl group, oxo group and thioxo group being especially preferred. A substituent which may be possessed by said phenyl group has a meaning similar to the substituent in an optionally substituted cyclic hydrocarbon described above.

A hydrocarbon group in an optionally substituted hydrocarbon group represented by $R^1$, $R^2$, $R^{2a}$, $R^3$, $R^4$ and $R^5$ in Formula [I] described above may, for example, be an aliphatic linear (acyclic) hydrocarbon group, alicyclic hydrocarbon group and aryl group, with an aliphatic linear hydrocarbon group being preferred.

An aliphatic linear hydrocarbon group in said hydrocarbon group may be a straight or branched aliphatic hydrocarbon group such as an alkyl group, alkenyl group, alkynyl group and the like. One preferred especially is a straight or branched alkyl group. Such an alkyl may, for example, be a $C_{1-7}$ alkyl such as methyl, ethyl, n-propyl, isopropyl, n-butyl, isobutyl, sec-butyl, tert-butyl, n-pentyl, isopentyl, neopentyl, 1-methylpropyl, n-hexyl, isohexyl, 1,1-dimethylbutyl, 2,2-dimethylbutyl, 3,3-dimethylbutyl, 3,3-dimethylpropyl, 2-ethylbutyl, n-heptyl and the like, with a $C_{3-5}$ alkyl such as n-propyl, isopropyl, isobutyl, neopentyl being preferred and isobutyl and neopentyl being especially preferred. Said alkenyl group may, for example, be a $C_{2-6}$ alkenyl such as vinyl, allyl, isopropenyl, 2-methylallyl, 1-propenyl, 2-methyl-1-propenyl, 2-methyl-2-propenyl, 1-butenyl, 2-butenyl, 3-butenyl, 2-ethyl-1-butenyl, 2-methyl-2-butenyl, 3-methyl-2-butenyl, 1-pentenyl, 2-pentenyl, 3-pentenyl, 4-pentenyl, 4-methyl-3-pentenyl, 1-hexenyl, 2-hexenyl, 3-hexenyl, 4-hexenyl, 5-hexenyl and the like, with vinyl, allyl, isopropenyl, 2-methylalllyl, 2-methyl-1-propenyl, 2-methyl-2-propenyl and 3-methyl-2-butenyl being especially preferred. Said alkynyl group may, for example, be a $C_{2-6}$ alkynyl such as ethynyl, 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the like, with ethynyl, 1-propynyl and 2-propynyl being especially preferred.

An alicyclc hydrocarbon group in said hydrocarbon group may, for example, be a saturated or unsaturated alicyclic hydrocarbon group such as a cycloalkyl group, cycloalkenyl group, cycloalkadienyl group and the like. Such a cycloalkyl group is preferably a cycloalkyl group having 3 to 9 carbon atoms such as cyclopropyl, cyclobutyl, cyclopentyl, cyclohexyl, cycloheptyl, cyclooctyl, cyclononyl and the like, with a $C_{3-6}$ cycloalkyl group such as cyclopropyl, cyclobutyl, cyclopentyl and cyclohexyl being especially preferred. Said cycloalkenyl group may, for example, be a $C_{5-6}$ cycloalkenyl group such as 2-cyclopenten-1-yl, 3-cyclopenten-1-yl, 2-cyclohexen-1-yl, 3-cyclohexen-1-yl, 1-cyclobuten-1-yl, 1-cyclopenten-1-yl and the like. Said cycloalkadienyl group may, for example, be a $C_{5-6}$ cycloalkadienyl group such as 2,4-cyclopentadien-1-yl, 2,4-cyclohexadien-1-yl, 2,5-cyclohexadien-1-yl.

An aryl group in said hydrocarbon group may, for example, be a monocyclic or fused polycyclic aromatic hydrocarbon group having 6 to 16 carbon atoms, such as phenyl, naphthyl, anthryl, phenanthryl, acenaphthylenyl and the like, with a $C_{6-10}$ aryl group such as phenyl, 1-naphtnyl and 2-naphtyl being especially preferred.

When a hydrocarbon group described above has a substituent, the substituent may, for example, be an optionally substituted aryl group, optionally substituted cycloalkyl group or cycloalkenyl group, optionally substituted heterocyclic group, optionally substituted amino group, optionally substituted hydroxyl group, optionally substituted thiol group, acyl group, halogen atom (e.g., fluorine, chlorine, bromine, iodine and the like), oxo group, carboxyl group, nitro group, cyano group, optionally substituted alkyl group and the like, and said hydrocarbon group may be substituted by 1 to 5 (preferably 1 to 3) of these optional substituents in any substitutable positions.

An aryl group in said optionally substituted aryl group may, for example, be a $C_{6-16}$ aryl group such as phenyl, naphthyl, anthryl, phenanthryl, acenaphthylenyl and the like, with a $C_{6-10}$ aryl group such as phenyl, 1-naphthyl and 2-naphthyl being especially preferred. A substituent on said aryl group may, for example, be (i) an optionally halogenated $C_{1-6}$ alkoxy group (e.g., methoxy, ethoxy, propoxy, trifluoromethoxy and the like), (ii) a halogen atom (e.g., fluorine, chlorine, bromine, iodine), (iii) an optionally halogenated $C_{1-6}$ alkyl group (e.g., methyl, ethyl, propyl, trifluoromethyl and the like), and said aryl group may be substituted by 1 or 2 of these optional substituents.

A cycloalkyl group in said optionally substituted cycloalkyl group may, for example, be a $C_{3-7}$ cycloalkyl group such as cyclopropyl, cyclobutyl, cyclopentyl, cyclohexyl, cycloheptyl and the like. The substituents on said cycloalkyl group and the number of the substitutions may be similar to those in the optionally substituted aryl group described above.

A cycloalkenyl group in said optionally substituted cycloalkenyl group may, for example, be a $C_{3-6}$ cycloalkenyl group such as cyclpropenyl, cyclobutenyl, cyclopentenyl, cyclohexenyl and the like. The substituents on said cycloalkenyl group and the number of the substitutions may be similar to those in the optionally substituted aryl group described above.

A heterocyclic group in said optionally substituted heterocyclic group may, for example, be an aromatic heterocyclic group or a saturated or unsaturated non-aromatic heterocyclic group (aliphatic heterocyclic group), which contains at least 1, preferably 1 to 4 heteroatoms of oxygen, sulfur and nitrogen as atoms forming the ring system (ring atoms), preferably an aromatic heterocyclic group. Said aromatic heterocyclic group may, for example, be a 5- to 6-membered aromatic monocyclic heterocyclic group (e.g., furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like) and an aromatic fused heterocyclic group formed by condensation of two or three 5- to 6-membered rings (5- to 6-membered aromatic monocyclic heterocyclic ring described above, benzene ring) (e.g., benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnnolinyl, quinazolyl, quinoxalinyl, phtharazinyl, naphthylidinyl, purinyl, puteririnyl, carbazolyl, α-carbolinyl, β-carbolinyl, γ-carbolinyl, acridinyl, phenoxazinyl, phenothiazinyl, phenazinyl, phenoxathiinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like), with a 5- to 6-membered aromatic monocyclic heterocyclic group such as furyl, thienyl, indolyl, isoindolyl, pyrazinyl, pyridyl and pyrimidinyl being preferred. Said non-aromatic heterocyclic group may, for example, be a 4- to 9-membered non-aromatic heterocyclic group such as oxylanyl, azethidinyl, oxetanyl, thietanyl, pyrrolidinyl, tetrahydrofuryl, thioranyl, piperidinyl, tetrahydropyranyl, morpholinyl, thiomorpholinyl, piperazinyl and the like (especially, a 5- to 9-membered cyclic amino group which may contain 1 to 3 heteroatoms such as oxygen and sulfur atoms in addition to nitrogen atoms, specifically, pyrrolidinyl, piperidinyl, piperazinyl, morpholinyl, 3,6-dihydropyridyl-1(2H)-yl and the like). Said heterocyclic group may have 1 to 4, preferably 1 to 2 substituents, and such substituents may, for example, be a $C_{1-6}$ alkyl group (e.g., methyl, ethyl, propyl, n-butyl, n-hexyl and the like), $C_{6-12}$ aryl group (e.g., phenyl), hydroxy-$C_{6-12}$ aryl group (e.g., 4-hydrpxyphenyl), $C_{1-4}$ alkylsulfonyl group (e.g., methylsulfonyl), $C_{7-15}$ aralkyl group (e.g., benzyl), $C_{1-4}$ alkoxy-$C_{1-4}$ alkyl group (for example, propoxyethyl and the like), a 5- to 9-membered heterocyclic group which contains 1 to 3 heteroatoms such as nitrogen, oxygen and sulfur atoms in addition to carbon atoms (for example, piperidinyl, piperazinyl, morpholinyl, thienyl, furyl, pyridyl, pyrimidinyl, thiazolyl, benzothiazolyl, benzoisothiazolyl, benzoxazolyl, benzoisoxazolyl and the like), hyroxyl group, oxo group, thioxo group and the like.

A substituent on said optionally substituted amino group (including amino group, mono- or di-substituted amino group) may, for example, be a lower ($C_{1-4}$) alkyl (e.g., methyl, ethyl, propyl and the like), a 5- to 9-membered heterocyclic group which contains 1 to 3 heteroatoms such as nitrogen, oxygen and sulfur atoms in addition to carbon atoms (for example, thienyl, furyl, pyridyl, pyrimidinyl, thiazolyl, benzothiazolyl, benzoisothiazolyl, benzoxazolyl, benzoisoxazolyl and the like), $C_{1-4}$ alkyl-carbonyl group (e.g., methylcarbonyl, ethylcarbonyl and the like), $C_{6-12}$ aryl-carbonyl group (e.g., benzoyl and the like), $C_{1-4}$ alkylsulfonyl group, $C_{1-4}$ alkoxy-$C_{1-4}$ alkyl group and the like. When the hydrocarbon group in an optionally substituted hydrocarbon group represented by $R^1$ is an alicyclic hydrocarbon group or aryl group, then the substituent may further be a $C_{1-6}$ alkyl group (e.g., methyl, ethyl, propyl, n-butyl, n-hexyl and the like).

Said optionally substituted hydroxyl group may, for example, be a hydroxyl group, an optionally halogenated $C_{1-16}$ alkoxy group, preferably an optionally halogenated $C_{1-4}$ alkoxy group, more preferably a $C_{1-4}$ alkoxy group (for example, methoxy, ethoxy, propoxy, butoxy, t-butoxy and the like), $C_{1-6}$ alkyl-carbonyloxy group (for example, methylcarbonyloxy, ethylcarbonyloxy, butylcarbonyloxy and the like), aminocarbonyloxy group, mono- or di-$C_{1-4}$ alkylaminocarbonyloxy group and the like.

Said optionally substituted thiol group may, for example, be a thiol group, an optionally halogenated $C_{1-16}$ alkylthio group, preferably an optionally halogenated $C_{1-4}$ alkylthio group, more preferably a $C_{1-4}$ alkylthio group (for example, methylthio, ethylthio and the like), a 5- to 9-membered heterocyclic group which contains 1 to 3 heteroatoms such as nitrogen, oxygen and sulfur atoms in addition to carbon atoms (for example, thienyl, furyl, pyridyl, pyrimidinyl, thiazolyl, benzothiazolyl, benzoisothiazolyl, benzoxazolyl, benzoisoxazolyl and the like)-thio group (e.g., 2-pyridylthio) and the like.

Said acyl group may, for example, be a formyl group, $C_{1-6}$ alkyl-carbonyl group, preferably $C_{1-4}$ alkyl-carbonyl group (e.g., methylcarbonyl, ethylcarbonyl), $C_{1-4}$ alkoxy-carbonyl group (e.g., mehtoxycarbonyl), $C_{1-6}$ alkyl-sulfonyl group, preferably a $C_{1-4}$ alkyl-sulfonyl group (e.g., methylsulfonyl, ethylsulfonyl), $C_{1-4}$ alkoxy-sulfonyl group (e.g., methoxysulfonyl), benzyloxycarbonyl group, $C_{3-6}$ cycloalkyl-carbonyl, carbamoyl group, mono- or di-$C_{1-4}$ alkylcarbamoyl group and the like.

More specifically, substituents on said hydrocarbon group are 1 to 4 substituents selected from halogen atoms; amino group; mono- or di-$C_{1-4}$ alkylamino group; carboxyl group; $C_{1-4}$ alkoxycarbonyl group; hydroxyl group; optionally halogenated $C_{1-4}$ alkoxy group; $C_{3-6}$ cycloalkyl group; nitro group; cyano group; optionally halogenated $C_{1-4}$ alkylthio group; cyclic amino group (for example, a 5- to 9-membered cyclic amino group which may contain 1 to 3 heteroatoms such as oxygen and sulfur atoms in addition to nitrogen atoms, specifically, pyrrolidinyl, piperidinyl, piperazinyl, morpholinyl and the like); $C_{1-4}$ alkyl-carbonylamino group; aminocarbonyloxy group; mono- or di-$C_{1-4}$ alkylaminocarbonyloxy group; $C_{1-4}$ alkylsulfonylamino group; $C_{1-4}$ alkoxy-carbonyl group; benzyloxycarbonyl group; carboxyl group; $C_{1-6}$ alkyl-carbonyl group; $C_{3-6}$ cycloalkyl-carbonyl; carbamoyl group; mono- or di-$C_{1-4}$ alkylcarbamoyl group; $C_{1-6}$ alkylsulfonyl group; $C_{1-6}$ alkyl group substituted by a cyclic amino group which is substituted by 1 to 2 groups selected from [1] $C_{1-4}$ alkyl, [2] $C_{1-4}$ alkylsulfonyl, [3] $C_{6-12}$ aryl group which may have a hydroxyl group, [4] $C_{7-15}$ aralkyl group, [5] $C_{1-4}$ alkoxy-$C_{1-4}$ alkyl, [6] 5- to 9-membered heterocyclic group which contains 1 to 3 heteroatoms such as nitrogen, oxygen and sulfur atoms in addition to carbon atoms, [7] hydroxyl group (for example, a 5- to 9-membered cyclic amino group which may contain 1 to 3 heteroatoms such as oxygen and sulfur atoms in addition to nitrogen atoms, specifically, pyrrolidinyl, piperidinyl, piperazinyl, morpholinyl and the like); $C_{1-6}$ alkyl-carbonyloxy group; amino group substituted by a $C_{1-4}$ alkyl and a 5- to 9-membered heterocyclic group which contains 1 to 3 heteroatoms such as nitrogen, oxygen and sulfur atoms in addition to carbon atoms; amino group substituted by a $C_{1-4}$ alkyl and a $C_{1-4}$ alkyl-carbonyl; amino group substituted by a $C_{1-4}$ alkyl and a $C_{6-12}$ aryl-carbonyl; $C_{1-6}$ alkyl-carbonyloxy group; mono- or di-$C_{1-4}$ alkoxy-$C_{1-4}$ alkyl-amino group; 5- to 9-membered heterocyclic group which contains 1 to 3 heteroatoms such as nitrogen, oxygen and sulfur atoms in addition to carbon atoms-thio group; oxo group and the like.

An optionally substituted hydroxyl group represented by $R^1$, $R^2$, $R^{2a}$ and $R^3$ in Formula [I] described above may, for example, be (i) a hydroxyl group, (ii) a $C_{1-4}$ alkoxy group (for example, methoxy, ethoxy, propoxy, isopropoxy, butoxy, t-butoxy and the like), (iii) a $C_{6-10}$ aryloxy group (for example, phenyloxy, naphthyloxy and the like), (iv) $C_{1-4}$ alkyl-carbonyloxy group (for example, formyloxy, acetoxy, propionyloxy and the like), (v) a $C_{2-6}$ alkanoyloxy group (for example, acetyloxy, propionyloxy, valeryloxy and the like) and (vi) a $C_{6-10}$ aryl-carbonyloxy group (for example, benzyloxy, naphthyloxy and the like), with hydroxyl group and $C_{1-4}$ alkoxy group (for example, methoxy, ethoxy, propoxy, isopropoxy and the like) being preferred.

In Formula [I] shown above, an optionally substituted amino group represented by $R^1$ may, for example, be an amino group which may be substituted by 1 to 3 substituents selected from (i) a $C_{1-4}$ alkyl group (for example, methyl, ethyl, propyl, isopropyl and the like), (ii) a $C_{1-4}$ alkyl-carbonyl group (for example, acetyl, propionyl, butyryl and the like), (iii) a $C_{1-4}$ alkoxy-carbonyl group (for exmaple, methoxycarbonyl, ethoxycarbonyl, propoxycarbonyl and the like), (iv) a halogen atom (for example, fluorine, chlorine and the like), (v) a phenyl group, (vi) a $C_{1-4}$ alkyl-phenyl group (for example, 4-methylphenyl, 3-methylphenyl, 2-methylphenyl and the like), (vii) a halogenated phenyl group (for example, 4-chlorophenyl, 3-chlorophenyl, 2-chlorophenyl and the like), and (viii) a $C_{1-4}$ alkoxy-phenyl group (for example, 4-methoxyphenyl, 3-methoxyphenyl, 2-methoxyphenyl and the like), with an amino group and a mono- or di-$C_{1-4}$ alkylamino group (for example, methylamino, ethylamino, propylamino, dimethylamino, diethylamino and the like) being especially preferred.

In Formula [I] shown above, a mercapto group which may be substituted by an optionally substituted hydrocarbon group represented by $R^3$ may, for example, be a mercapto group which may be substituted by an optionally substituted hydrocarbon group similar to the optionally substituted hydrocarbon group described above, and among these a $C_{1-4}$ alkylthio group (for example, methylthio, ethylthio, propylthio and the like) is especially preferred.

In Formula [I] shown above, a $C_{1-3}$ alkylene group in a $C_{1-3}$ alkylene group which may be substituted by an oxo group or thioxo group represented by D may, for example, be —CH$_2$—, —CH$_2$CH$_2$—, —CH$_2$CH$_2$CH$_2$— and —CH(CH$_3$)—CH$_2$— and the like, with —CH$_2$— and —CH$_2$CH$_2$— being preferred.

Said $C_{1-3}$ alkylene group substituted by an oxo group or thioxo group may, for example, be —CO—, —CS—, —CH$_2$CO—, —CH$_2$CS—, —CH$_2$CH$_2$CO—, —CH$_2$CH$_2$CS— and the like.

D is preferably (i) a $C_{1-3}$ alkylene group which may be substituted by an oxo group, (ii) —NH—, (iii) —CH$_2$NH—, and those preferred especially are —CH$_2$—, —CH$_2$CO—, —CH$_2$CH$_2$CO—, —NH—.

In Formula [I] shown above, when D is taken together with a constituent atom of the ring B to form a 5- to 7-membered ring which may be substituted by an oxo group or thioxo group, then a preferred example of said 5- to 7-membered ring is a 5- to 7-membered saturated heterocyclic ring containing 1 to 3 nitrogen atoms which may be substituted by an oxo group or thioxo group where a constituent atom of the ring B adjacent to the constituent atom of the ring B to which D is attached is taken together, with a 5- or 6-membered saturated heterocyclic ring containing one nitrogen atom being especially preferred.

A typical preferred example when D is taken together with a constituent atom of the ring B to form a 5- to 7-membered ring which may be substituted by an oxo group or thioxo group is represented by Formula:

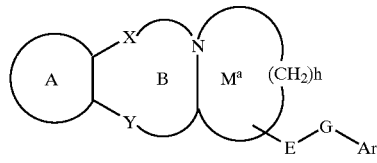

wherein ring $M^a$ may be substituted by an oxo group or thioxo group; h is an integer of 3 to 5; other symbols are as defined above, preferably represented by Formula:

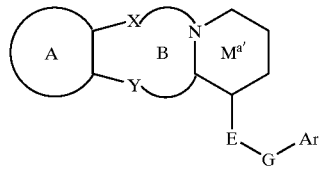

wherein ring $M^{a'}$ may be substituted by an oxo group; other symbols are as defined above.

A preferred example of E in Formula [I] shown above is —NR$^{4'}$— (in which R$^{4'}$ is a hydrogen atom or a $C_{1-6}$ alkyl such as methyl, ethyl, n-propyl, n-butyl, isopropyl, hexyl and the like, which may be substituted), —CONR$^{5'}$— (in which R$^{5'}$ is a hydrogen atom or a $C_{1-6}$ alkyl such as methyl, ethyl, n-propyl, n-butyl, isopropyl, hexyl and the like, which may be substituted). The substituent which may be possessed by said R$^{4'}$ and R$^{5'}$ may be similar to the substituent which may be possessed by an optionally substituted hydrocarbon group described above. More preferably, E is —CONR$^{5'}$— (in which R$^{5'}$ is a hydrogen atom or a $C_{1-6}$ alkyl such as methyl, ethyl, n-propyl, n-butyl, isopropyl, hexyl and the like, which may be substituted).

In Formula [I] shown above, when $R^4$ is taken together with a constituent atom of the ring B to form a 5- to 7-membered ring which may be substituted by an oxo group or thioxo group, then a preferred example of said 5- to 7-membered ring is a 5- to 7-membered saturated heterocyclic ring containing 2 to 4 nitrogen atoms which may be substituted by an oxo group or thioxo group where a constituent atom of the ring B adjacent to the constituent atom of the ring B to which $R^4$ is attached is taken together, with a 5- or 6-membered saturated heterocyclic ring containing two nitrogen atoms being especially preferred.

A typical preferred example when $R^4$ is taken together with a constituent atom of the ring B to form a 5- to 7-membered ring which may be substituted by an oxo group or thioxo group is represented by Formula:

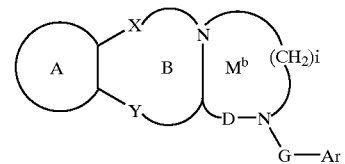

wherein ring $M^b$ may be substituted by an oxo group or thioxo group; i is an integer of 1 to 3; provided that the total number of carbon atoms in the constituent atoms of D and —(CH$_2$)i- is 2 to 4; and other symbols are as defined above, preferably represented by Formula:

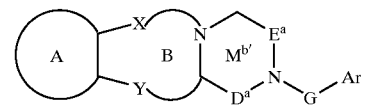

wherein $D^a$ and $E^a$ are —CH$_2$— or —CO—; and other symbols are as defined above.

In Formula [I] shown above, a $C_{1-3}$ alkylene group represented by G may, for example, be methylene, ethylene, propylene and the like.

Preferred examples of D, E and G are the combinations in which (i) D is —CO—, E is —NR$^4$— (in which R$^4$ is as defined above), G is —CH$_2$— or —CH$_2$CH$_2$—; (ii) D is —CO—, E is —NR$^4$— (in which R$^4$ is as defined above), G is a bond; (iii) D is —CH$_2$CO— or —CH$_2$CH$_2$CO—, E is —NR$^4$— (in which R$^4$ is as defined above), G is a bond; (iv) D is —CH$_2$CO— or —CH$_2$CH$_2$CO—, E is —NR$^4$— (in which R$^4$ is as defined above), G is —CH$_2$— or —CH$_2$CH$_2$—; (v) D is —CH$_2$— or —CH$_2$CH$_2$—, E is —O—, G is —CH$_2$— or —CH$_2$CH$_2$—; (vi) D is —CH$_2$— or —CH$_2$CH$_2$—, E is —NR$^4$— (in which R$^4$ is as defined above), G is —CH$_2$— or —CH$_2$CH$_2$—; (vii) D is —NH—, E is —COR$^5$— (in which R$^5$ is as defined above), G is a bond and (viii) D is —CH$_2$— or —CH$_2$CH$_2$—, E is —S— or —SO—, G is —CH$_2$— or —CH$_2$CH$_2$—.

In Formula [I] shown above, Ar represents an optionally substituted aryl group or optionally substituted heterocyclic group. An aryl group in an optionally substituted aryl group represented by Ar is preferably a $C_{6-10}$ aryl group such as phenyl and naphthyl, with a phenyl group being especially preferred. Such an aryl group represented by Ar may contain 1 to 5, preferably 1 to 3 same or different substituents. The substitution may occur in any position in the ring. Such a substituent may, for example, be (i) an optionally halogenated $C_{1-4}$ alkyl group (for example, methyl, chloromethyl, difluoromethyl, trichloromethyl, trifluoromethyl, ethyl, 2-bromoethyl, 2,2,2-trifluoroethyl, propyl, isopropyl, 3,3,3-trifluoropropyl, butyl and the like), (ii) a $C_{1-4}$ alkyl substituted by an amino group (for example, aminomethyl, 2-aminoethyl and the like), (iii) a $C_{1-4}$ alkyl group substituted by a mono- or di-$C_{1-4}$ alkylamino group (for example, methylaminomethyl, dimethylaminomethyl, 2-methylaminoethyl, 2-dimethylaminoethyl and the like), (iv) a $C_{1-4}$ alkyl group substituted by a carboxyl group (for example, carboxymethyl, carboxyethyl and the like), (v) a $C_{1-4}$ alkyl group substituted by a $C_{1-4}$ alkoxycarbonyl group (for example, methoxycarbonylethyl, ethoxycarbonylethyl and the like), (vi) a $C_{1-4}$ alkyl group substituted by a hydroxy group (for example, hydroxymethyl, hydroxyethyl and the like), (vii) a $C_{1-4}$ alkyl group substituted by a $C_{1-4}$ alkoxycarbonyl group (for example, methoxymethyl, methoxyethyl, ethoxyethyl and the like), (viii) a $C_{3-6}$ cycloalkyl group (for example, cyclopropyl, cyclobutyl, cyclopentyl, cyclohexyl and the like), (ix) a halogen atom (for example, fluorine, chlorine, bromine, iodine and the like), (x) a nitro group, (xi) a cyano group, (xii) a hydroxyl group, (xiii) an optionally halogenated $C_{1-4}$ alkoxy group (for example, methoxy, difluoromethoxy, trifluoromethoxy, ethoxy, 2,2,2-trifluoroethoxy, propyloxy, butoxy, isopropyloxy and the like), (xiv) an optionally halogenated $C_{1-4}$ alkylthio group (for example, methylthio, difluoromethylthio, trifluoromethylthio, ethylthio, propylthio, isopropylthio, butylthio and the like), (xv) an amino group, (xvi) a mono- or di-$C_{1-4}$ alkylamino group (for example, methylamino, ethylamino, propylamino, dimethylamino, diethylamino and the like), (xvii) a cyclic amino group (for example, 5- to 9-membered cyclic amino group which may contain 1 to 3 heteroatoms such as oxygen and sulfur atoms in addition to nitrogen atoms, specifically, pyrrolidino, pyperidino, morpholino and the like); (xviii) a $C_{1-4}$ alkyl-carbonylamino group (for example, acetylamino, propionylamino, butyrylamino and the like), (xix) an aminocarbonyloxy group, (xx) a mono- or di-$C_{1-4}$ alkylaminocarbonyloxy group (for example, methylaminocarbonyloxy, ethylaminocarbonyloxy, dimethylaminocarbonyloxy, diethylaminocarbonyloxy and the like), (xxi) a $C_{1-4}$ alkylsulfonylamino group (for example, methylsulfonylamino, ethylsulfonylamino, propylsulfomylamino and the like), (xxii) a $C_{1-4}$ alkoxycarbonyl group (for example, methoxycarbonyl, ethoxycarbonyl, propoxycarbonyl, isobutoxycarbonyl and the like), (xxiii) a benzyloxycarbonyl group, (xxiv) a carboxyl group, (xxv) a $C_{1-6}$ alkyl-carbonyl group (for example, methylcarbonyl, ethylcarbonyl, butylcarbonyl and the like), (xxvi) a $C_{3-6}$ cycloalkyl-carbonyl (for example, cyclohexylcarbonyl and the like), (xxvii) a carbamoyl group, (xxviii) a mono- or di-$C_{1-4}$ alkylcarbamoyl group (for example, methylcarbamoyl, ethylcarbamoyl, propylcarbamoyl, butylcarbamoyl, diethylcarbamoyl, dibutylcarbamoyl and the like) and (xxix) a $C_{1-6}$ alkylsulfonyl group (for example, methylsulfonyl, ethylsulfonyl, propylsulfonyl and the like), as well as an optionally substituted heterocyclic group represented by Ar described below which may itself be employed as a substituent on the aryl group. Such an optionally substituted heterocyclic group may, for example, be a 5- or 6-membered aromatic monocyclic heterocyclic group (for example, furyl, thienyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like) which may be substituted by 1 to 3 substituents selected from (i) an optionally halogenated $C_{1-4}$ alkyl group (for example, methyl, chloromethyl, difluoromethyl, trichloromethyl, trifluoromethyl, ethyl, 2-buromoethyl, 2,2, 2-trifluoroethyl, propyl, isopropyl, 3,3,3-trifluoropropyl, butyl and the like), (ii) a $C_{3-6}$ cycloalkyl group (for example, cyclopropyl, cyclobutyl, cyclopentyl, cyclohexyl and the like), (iii) a halogen atom (e.g., fluorine, chlorine, bromine, iodine and the like), (iv) a hydroxyl group, (v) an optionally halogenated $C_{1-4}$ alkoxy group (for example, methoxy, difluoromethoxy, trifluoromethoxy, ethoxy, 2,2,2-trifluoroethoxy, propyloxy, butyloxy, isopropyloxy and the like, (vi) an optionally halogenated $C_{1-4}$ alkylthio group (for example, methylthio, difluoromethylthio, trifluoromethylthio, ethylthio, propylthio, isopropylthio, butylthio and the like), (vii) an amino group, (viii) a mono- or di-$C_{1-4}$ alkylamino group (for example, methylamino, ethylamino, propylamino, dimethylamino, diethylamino and the like), (ix) a $C_{1-4}$ alkoxy-carbonyl group (for example, methoxycarbonyl, ethoxycarbonyl, propoxycarbonyl, isobutoxycarbonyl and the like), (x) a carboxyl group and a $C_{1-6}$ alkyl-carbonyl group (for example, methylcarbonyl, ethylcarbonyl, butylcarbonyl and the like).

Preferred among the substituents listed above are (i) an optionally halogenated $C_{1-4}$ alkyl group (for example, methyl, chloromethyl, difluoromethyl, trichloromethyl, trifluoromethyl, ethyl, 2-bromoethyl, 2,2,2-trifluoroethyl, propyl, isopropyl, 3,3,3-trifluoropropyl and the like), (ii) a halogen atom (for example, fluorine, chlorine, bromine and the like), (iii) a nitro group, (iv) a hydroxyl group, (v) an optionally halogenated $C_{1-4}$ alkoxy group (for example, methoxy, difluoromethoxy, trifluoromethoxy, ethoxy, 2,2,2-trifluoroethoxy and the like), (vi) an amino group, (vii) a $C_{1-4}$ alkyl group substituted by a mono- or di-$C_{1-4}$ alkylamino group (for example, methylaminomethyl, dimethylaminomethyl, 2-methylaminoethyl, 2-dimethylaminoethyl and the like), (viii) a mono- or di-$C_{1-4}$ alkylamino group (for example, methylamino, ethylamino, dimethylamino, diethylamino and the like), (ix) a $C_{1-4}$ alkoxy-carbonyl group (for example, methoxycarbonyl, ethoxycarbonyl and the like), (x) a carboxyl group and (xi) a carbamoyl group, with an optionally halogenated $C_{1-4}$ alkyl group (for example, methyl, chloromethyl, difluoromethyl, trichloromethyl, trifluoromethyl, ethyl, 2-bromoethyl, propyl, isopropyl and the like), a halogen atom (for example, fluorine, chlorine, bromine and the like) and an optionally halogenated $C_{1-4}$ alkoxy group (for example, methoxy, trifluoromethoxy, ethoxy, propoxy and the like) being especially preferred.

In Formula [I] shown above, a heterocyclic group in an optionally substituted heterocyclic group represented by Ar may, for example, be a 5- to 9-membered, preferably 5- or 6-membered aromatic heterocyclic group having 1 to 4, preferably 1 to 2 heteroatoms such as nitrogen, oxygen and sulfur atoms in addition to carbon atoms.

Such an aromatic heterocyclic group may, for example, be an aromatic monocyclic heterocyclic group such as furyl, thienyl, pyrrolyl, oxazolyl, isoxazolyl, thiazolyl, isothiazolyl, imidazolyl, pyrazolyl, 1,2,3-oxadiazolyl, 1,2,4-oxadiazolyl, 1,3,4-oxadiazolyl, furazanyl, 1,2,3-thiadiazolyl, 1,2,4-thiadiazolyl, 1,3,4-thiadiazolyl, 1,2,3-triazolyl, 1,2,4-triazolyl, tetrazolyl, pyridyl, pyridazinyl, pyrimidinyl, pyrazinyl, triazinyl and the like, or an aromatic fused heterocyclic group such as benzofuranyl, isobenzofuranyl, benzo[b]thienyl, indolyl, isoindolyl, 1H-indazolyl, benzimidazolyl, benzoxazolyl, 1,2-benzoisoxazolyl, benzothiazolyl, 1,2-benzoisothiazolyl, 1H-benzotriazolyl, quinolyl, isoquinolyl, cinnnolinyl, quinazolyl, quinoxalinyl, phtharazinyl, naphthylidinyl, purinyl, puteririnyl, α-carbazolyl, β-carbolinyl, carbolinyl, γ-carbolinyl, acridinyl, phenoxazinyl, phenothiazinyl, phenazinyl, phenoxathiinyl, thianthrenyl, phenanthridinyl, phenanthrolinyl, indolidinyl, pyrrolo[1,2-b]pyridazinyl, pyrazolo[1,5-a]pyridyl, imidazo[1,2-a]pyridyl, imidazo[1,5-a]pyridyl, imidazo[1,2-b]pyridazinyl, imidazo[1,2-a]pyrimidinyl, 1,2,4-triazolo[4,3-a]pyridyl, 1,2,4-triazolo[4,3-b]pyridazinyl and the like.

Among the heterocyclic groups described above, a 5- or 6-membered heterocyclic group is preferred, and those employed preferably are furyl, thienyl, pyrrolyl, oxazolyl, isoxazolyl, imidazolyl, pyrazolyl, pyridyl, pyrimidinyl, pyridazinyl, quinolyl, isoquinolyl, thiazolyl, thiadiazolyl, thiophenyl and the like. Furyl, thienyl and pyridyl are especially preferred.

A substituent which may be possessed by an optionally substituted heterocyclic group represented by Ar may, for example, be (i) an optionally halogenated $C_{1-4}$ alkyl group (for example, methyl, chloromethyl, difluoromethyl, trichloromethyl, trifluoromethyl, ethyl, 2,2-dibromoethyl, 2,2,2-trifluoroethyl, propyl, isopropyl, 3,3,3-trifluoropropyl, butyl and the like), (ii) a $C_{3-6}$ cycloalkyl group (for example, cyclopropyl, cyclobutyl, cyclopentyl, cyclohexyl and the like), (iii) a halogen atom (for example, fluorine, chlorine, bromine, iodine and the like), (iv) a nitro group, (v) a cyano group, (vi) a hydroxyl group, (vii) an optionally halogenated $C_{1-4}$ alkoxy group (for example, methoxy, fluoromethoxy, difluoromethoxy, trifluoromethoxy, ethoxy, 2,2,2-trifluoroethoxy, propyloxy, butyloxy, isopropyloxy and the like), (viii) an optionally halogenated $C_{1-4}$ alkylthio group (for example, methylthio, difluoromethylthio, trifluoromethylthio, ethylthio, propylthio, isopropylthio, butylthio and the like), (ix) an amino group, (x) a mono- or di-$C_{1-4}$ alkylamino group (for example, methylamino, ethylamino, propylamino, dimethylamino, diethylamino and the like), (xi) a cyclic amino group (for example, a 5- to 9-membered cyclic amino group which may contain 1 to 3 heteroatoms such as oxygen and sulfur atoms in addition to nitrogen atoms, specifically, pyrrolidino, piperidino, morpholino and the like), (xii) a $C_{1-4}$ alkyl-carbonylamino group (for example, acetylamino, propionylamino, butyrylamino and the like), (xiii) an aminocarbonyloxy group, a mono- or di-$C_{1-4}$ alkylaminocarbonyloxy group (for example, methylaminocarbonyloxy, ethylaminocarbonyloxy, dimethylaminocarbonyloxy, diethylaminocarbonyloxy and the like), (xiv) a $C_{1-4}$ alkylsulfonylamino group (for example, methylsulfonylamino, ethylsulfonylamino, propylsulfonylamino and the like), (xv) a $C_{1-4}$ alkoxy-carbonyl group (for example, methoxycarbonyl, ethoxycarbonyl, propoxycarbonyl, isobutoxycarbonyl and the like), (xvi) a carboxyl group, (xvii) a $C_{1-6}$ alkyl-carbonyl group (for example, methylcarbonyl, ethylcarbonyl, butylcarbonyl and the like), (xviii) a $C_{3-6}$ cycloalkylcarbonyl group (for example, cyclohexylcarbonyl and the like), (xix) a carbamoyl group, a mono- or di-$C_{1-4}$ alkylcarbamoyl group (for example, methylcarbamoyl, ehtylcarbamoyl, propylcarbamoyl, butylcarbamoyl, diethylcarbamoyl, dibutylcarbamoyl and the like), (xx) a $C_{1-6}$ alkylsulfonyl group (for example, methylsulfonyl, ethylsulfonyl, propylsulfonyl and the like), (xxi) a $C_{3-6}$ cycloalkylsulfonyl (for example, cyclopentylsulfonyl, cyclohexylsulfonyl and the like), (xxii) a phenyl, naphthyl, phenoxy, benzoyl, phenoxycarbonyl, phenyl-$C_{1-4}$ alkylcarbamoyl, phenylcarbamoyl, phenyl-$C_{1-4}$ alkyl-carbonylamino, benzoylamino, phenyl-$C_{1-4}$ alkylsulfonyl, phenylsulfonyl, phenyl-$C_{1-4}$ alkylsulfinyl, phenyl-$C_{1-4}$ alkylsulfonylamino or phenylsuofonylamino and the like, whose phenyl or naphthyl group may be substituted by 1 to 3 substituents selected from $C_{1-4}$ alkyl group such as methyl, ethyl, propyl, butyl and isopropyl, $C_{1-4}$ alkoxy group such as methoxy, ethoxy, n-propyloxy, i-propyloxy and n-butyloxy, halogen atom such as chloro, bromo and iodo, hydroxyl group, benzyloxy group, amino group, mono- or di-$C_{1-4}$ alkylamino group, nitro group, $C_{1-6}$ alkylcarbonyl group and the like.

Among those listed above, preferred substituents may, for example, be (i) a halogen atom (for example, fluorine, chlorine, bromine and the like), (ii) an optionally halogenated $C_{1-4}$ alkyl group (for example, methyl, chloromethyl, difluoromethyl, trifluoromethyl, ethyl, propyl, isopropyl and the like), (iii) a $C_{3-6}$ cycloalkyl group (for example, cyclopropyl, cyclobutyl and the like), (iv) a hydroxyl group, (v) an optionally halogenated $C_{1-4}$ alkoxyl group (for example, methoxy, difluoromethoxy, trifluoromethoxy, ethoxy and the like), (vi) an optionally halogenated $C_{1-4}$ alkylthio group (for example, methylthio, trifluorothio, ethylthio and the like), (vii) an amino group, (viii) a mono- or di-$C_{1-4}$ alkylamino group (for example, methylamino, ethylamino, dimethylamino, diethylamino and the like), (ix) a $C_{1-4}$ alkoxy-carbonyl group (for example, methoxycarbonyl, ethoxycarbonyl and the like) and (x) a carboxyl group and the like, with a halogen atom (for example, fluoro, chloro and the like), $C_{1-4}$ alkyl (for example, methyl, ethyl and the like), $C_{3-6}$ cycloalkyl group (for example, cyclopropyl, cyclobutyl and the like), hydroxyl group, $C_{1-4}$ alkoxy group (for example, methoxy, ethoxy and the like) and carboxyl group being especially preferred.

Ar is preferably a phenyl group which may be substituted by 1 to 3 substituents selected from halogen atoms (for example, fluorine, chlorine and the like), an optionally halogenated $C_{1-4}$ alkyl group (for example, methyl, difluoromethyl, trifluoromethyl, ethyl, 2,2,2-trifluoroethyl, propyl, isopropyl and the like) and an optionally halogenated $C_{1-4}$ alkoxy group (for example, methoxy, difluoromethoxy, trifluoromethoxy, ethoxy, 2,2,2-trifluoroethoxy, propoxy, isopropoxy and the like). A 5- to 6-membered heterocyclic group containing 1 to 3 heteroatoms (for example, nitrogen atoms, oxygen atoms, sulfur atoms and the like) other than carbon atoms (for example, furyl, pyridyl, pyrimidinyl, thienyl, thiazolyl, thiadiazolyl and the like) which may be substituted by a substituent selected from an optionally halogenated $C_{1-4}$ alkyl group (for example, methyl, trifluoromethyl, ethyl and the like), $C_{1-4}$ alkoxy group (for example, methoxy, ethoxy, propoxy and the like) and $C_{3-6}$ cycloalkyl (for example, cyclopropyl and the like) is also preferred.

One especially preferred as Ar may, for example, be a phenyl group or pyridyl group which may be substituted by 1 to 4 substituents selected from halogen atoms (for example, chlorine, fluorine and the like), optionally halogenated $C_{1-4}$ alkyl group (for example, methyl, trifluoromethyl, ethyl, isopropyl and the like), optionally halogenated $C_{1-4}$ alkoxy group (for example, methoxy, trifluoromethoxy, ethoxy and the like), di-$C_{1-4}$ alkylamino group (for example, dimethylamino and the like), $C_{1-3}$ acyloxy group (for example, acetoxy and the like) and hydroxyl group.

A preferred compound represented by Formula [I] or a salt thereof may, for example, be a compound represented by Formula [II]:

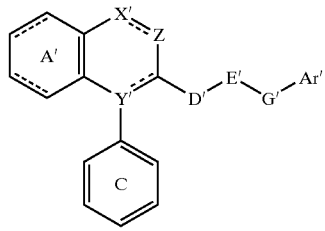

in which ring A' is an optionally substituted 6-membered hydrocarbon group; ring C is an optionally substituted benzene group; one of X' and Z is —NR$^{1'}$— (in which R$^{1'}$ is a hydrogen atom, optionally substituted hydrocarbon group or optionally substituted amino group), —O— or —S— and the other is —CO—, —CS— or —C(R$^{2'}$)R$^{2a'}$— (in which each of R$^{2'}$ and R$^{2a'}$ is a hydrogen atom or optionally substituted hydrocarbon group), or one of them is —N= and the other is =CR$^{3'}$— (in which R$^{3'}$ is a hydrogen atom, halogen atom, optionally substituted hydrocarbon group, optionally substituted amino group, optionally substituted hydroxyl group or a mercapto group which may be substituted by an optionally substituted hydrocarbon group); === is a single bond or double bond; Y', when === adjacent to Y' is a single bond, is

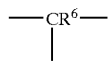

(in which R$^6$ is a hydrogen atom, hydroxyl group or optionally substituted hydrocarbon group) or a nitrogen atom, Y', when === adjacent to Y' is a double bond, is a carbon atom; D' is a C$_{1-3}$ alkylene group which may be substituted by an oxo group or thioxo group; E' is —NR$^7$— (in which R$^7$ is a hydrogen atom or optionally substituted hydrocarbon group), —O— or —S(O)n- (in which n is 0, 1 or 2); G' is a bond or C$_{1-3}$ alkylene group; Ar' is an optionally substituted aryl group or optionally substituted heterocyclic group, D' may be taken together with Z' to form a 5- to 7-membered ring which may be substituted by an oxo group or thioxo group, R$^7$ may be taken together with Z to form a 5- to 7-membered ring which may be substituted by an oxo group or thioxo group, or a salt thereof.

In Formula [II] shown above, a substituent which may be possessed by ring A' and ring C has a meaning similar to the substituent which may be possessed by an optionally substituted cyclic hydrocarbon represented by ring A in Formula [I] shown above.

In Formula [II] shown above, "an optionally substituted hydrocarbon group", "an optionally substituted amino group", "an optionally substituted hydroxyl group", "mercapto group which may be substituted by an optionally substituted hydrocarbon group", "C$_{1-3}$ alkylene group which may be substituted by an oxo group or thioxo group", "C$_{1-3}$ alkylene group", "an optionally substituted aryl group or optionally substituted heterocyclic group" have the meanings similar to those described above.

"A 5- to 7-membered ring which may be substituted by an oxo group or thioxo group" formed by D' taken together with Z has the meaning similar to "a 5- to 7-membered ring which may be substituted by an oxo group or thioxo group" formed by D taken together with a constituent atom of the ring B.

"A 5- to 7-membered ring which may be substituted by an oxo group or thioxo group" formed by R$^7$ taken together with Z has the meaning similar to "a 5- to 7-membered ring which may be substituted by an oxo group or thioxo group" formed by R$^4$ taken together with a constituent atom of the ring B.

Another preferred example of a compound represented by Formula [I] or a salt thereof may, for example, be a compound represented by Formula [III]:

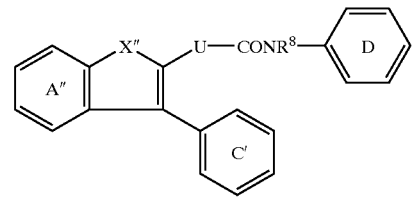

in which each of ring A", ring C' and ring D is an optionally substituted benzene ring, X" is —NR$^8$— (in which R$^8$ is a hydrogen atom or optionally substituted hydrocarbon group), —O— or —S—, U is —(CH$_2$)m- (in which m is 1 or 2) or —NH—, R$^a$ is a hydrogen atom or optionally substituted hydrocarbon group), or a salt thereof.

In Formula [III] shown above, a substituent which may be possessed by rings A", C' or D has a meaning similar to the substituent which may be possessed by an optionally substituted cyclic hydrocarbon represented by ring A in Formula [I] shown above.

In Formula [III] shown above, "an optionally substituted hydrocarbon group" has the meaning similar to that described above.

A further preferred example of a compound represented by Formula [I] or a salt thereof may, for example, be a compound represented by Formula [IV]:

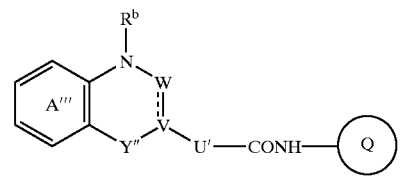

in which ring A'" is an optionally substituted benzene ring, Q is an optionally substituted aromatic ring, W is —CH$_2$—, —CO— or —CS—, V is

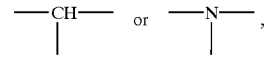

or W and V are taken together to form

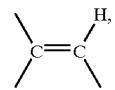

Y" is —CH$_2$—, —O—, —S—, —CO—, —CS— or —NR$^9$ (in which R$^9$ is a hydrogen atom or hydrocarbon group), U' is —NH—, —CH$_2$— or —CH$_2$NH—, R$^b$ is a hydrogen atom or optionally substituted hydrocarbon group, === is a single bond or double bond, or a salt thereof.

Ring A'" represents an optionally substituted benzene ring, and ring Q represents an optionally substituted aromatic ring. A substituent on such a benzene ring and aromatic ring may, for example, be (i) a halogen atom (for example, fluorine, chlorine, bromine, iodine and the like, preferably chlorine and fluorine), (ii) an alkyl group which may be substituted by a halogen, (iii) an alkoxy group which may be substituted by a halogen, (iv) an alkylthio group which may be substituted by a halogen, (v) a $C_{1-7}$ acylamino group (for example, a $C_{1-6}$ alkanoylamino group such as formylamino, acetylamino, propionylamino and butyrylamino, as well as benzoylamino group and the like), (vi) an amino group which may be substituted by a $C_{1-4}$ alkylamino group (for example, a mono- or di-$C_{1-4}$ alkylamino group such as methylamino, ethylamino, propylamino, dimethylamino, methylethylamino and methylpropylamino), (vii) a $C_{1-3}$ acyloxy group (for example, formyloxy, acetoxy, propionyloxy group and the like), (viii) a hydroxyl group, (ix) a cyano group, (x) a carboxyl group and the like.

An alkyl group which may be substituted by a halogen described above may, for example, be a straight or branched alkyl group having 1 of 6 carbon atoms unsubstituted or substituted by 1 to 5 halogen atoms (for example, fluorine, chlorine, bromine, iodine and the like, preferably, chlorine and bromine), and those employed widely are methyl, chloromethyl, difluoromethyl, trichloromethyl, trifluoromethyl, ethyl, 2-buromoethyl, 2,2,2-trifluoroethyl, pentafluoroethyl, propyl, 3,3,3-trifluoropropyl, isopropyl, 2-trifluoromethylethyl, butyl, 4,4,4-trifluorobutyl, isobutyl, sec-butyl, tert-butyl, pentyl, isopentyl, neopentyl, 5,5,5-trifluoropentyl, 4-trifluoromethylbutyl, hexyl, 6,6,6-trifluorohexyl, 5-trifluoromethylpentyl and the like, with a straight or branched alkyl group having 1 to 4 carbon atoms unsubstituted or substituted by 1 to 3 halogen atoms described above being employed preferably, including methyl, chloromethyl, difluoromethyl, trichloromethyl, trifluoromethyl, ethyl, 2-bromoethyl, 2,2,2-trifluoroethyl, propyl, 3,3,3-trifluoropropyl, isopropyl, 2-trifluoromethylethyl, butyl, 4,4,4-trifluorobutyl, isobutyl, sec-butyl, tert-butyl and the like.

An alkoxy group which may be substituted by a halogen and an alkylthio group which may be substituted by a halogen are an alkoxy group which may be substituted by a halogen and an alkylthio group which may be substituted by a halogen formed by binding an alkyl group or a halogen-substituted alkyl group described above with an oxygen atom and a sulfur atom, respectively.

An alkoxy group which may be substituted by a halogen may, for example, be a straight or branched alkoxy group having 1 to 6 carbon atoms unsubstituted or substituted by 1 to 5 halogen atoms as described above, and those employed widely are methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy, pentoxy, hexyloxy and the like, with a straight or branched alkoxy group having 1 to 4 carbon atoms unsubstituted or substituted by 1 to 3 halogen atoms as described above being employed preferably, including methoxy, difluoromethoxy, trifluoromethoxy, ethoxy, 2,2,2-trifluoroethoxy, propoxy, isopropoxy, butoxy, 4,4,4-trifluorobutoxy, isobutoxy, sec-butoxy and the like.

An alkylthio group which may be substituted by a halogen may, for example, be a straight or branched alkylthio group having 1 to 6 carbon atoms unsubstituted or substituted by 1 to 5 halogen atoms as described above, and those employed widely are methylthio, difluoromethylthio, trifluoromethylthio, ethylthio, propylthio, isopropylthio, butylthio, 4,4,4-trifluorobutylthio, pentylthio, hexylthio and the like, with a straight or branched alkylthio group having 1 to 4 carbon atoms unsubstituted or substituted by 1 to 3 halogen atoms as described above being employed preferably, including methylthio, difluoromethylthio, trifluoromethylthio, ethylthio, propylthio, isopropylthio, butylthio, 4,4,4-trifluorobutylthio and the like.

The expression "which may be substituted by a halogen" hereinafter means that 1 to 3 halogens may be possessed as described above.

A preferred substituent on a benzene ring represented by ring A''' and on an aromatic ring represented by ring Q is (i) a halogen atom, (ii) a $C_{1-6}$ alkyl group which may be substituted by a halogen, (iii) a $C_{1-6}$ alkoxy group, (iv) a hydroxy group, (v) an amino group which may be substituted by a $C_{1-4}$ alkyl group and (vi) a $C_{1-3}$ acyloxy group. Each of the terms (i) to (vi) has the meaning described above.

A substituent on a benzene ring represented by ring A''' and on an aromatic ring represented by ring Q may be present in any substitutable position on the benzene ring and the aromatic ring, and when the substitution occurs twice or more, then the substituents may be same or different, and the number of the substituents may be 1 to 4, preferably 2 or 3. It is also possible that adjacent carbon atoms on the ring A or the ring Q are taken together with —(CH$_2$)$_q$— (q is an integer of 3 to 5) to form a 5- to 7-membered ring, and such a case is also encompassed in the compound represented by Formula [III].

As ring A, a benzene ring substituted by 1 to 4 substituents selected from a halogen (for example, chlorine), $C_{1-4}$ alkyl group which may be substituted by 1 to 3 halogens (for example, methyl, ethyl, isopropyl, trifluoromethyl and the like) and $C_{1-4}$ alkoxy group (for example, methoxy and the like) is employed, with a benzene ring substituted by a single halogen (having the meaning described above) or a single $C_{1-4}$ alkyl group (for example, methyl, ethyl, isopropyl and the like) being preferred.

An aromatic ring represented by ring Q may, for example, be a 5- or 6-membered aromatic ring which may have 1 to 4, preferably 1 to 2 oxygen, sulfur or nitrogen atoms in addition to carbon atoms, preferably a 5- or 6-membered aromatic ring which may have 1 or 2 nitrogen atoms in addition to carbon atoms, more preferably, (1) a benzene ring, (2) a pyridine ring, (3) a pyrazine ring, (4) a pyrimidine ring, (5) a pyridazine ring and the like, still preferably a benzene ring or pyrimidine ring, especially a benzene ring.

Ring Q may have same or different 1 to 4 substituents, and such substituents are preferably (i) halogens (for example, fluorine, chlorine and the like), (ii) a $C_{1-4}$ alkyl group which may be substituted by a halogen (for example, methyl, ethyl, isopropyl, trifluoromethyl and the like), (iii) a $C_{1-4}$ alkoxy group which may be substituted by a halogen (for example, methoxy, ethoxy, isopropoxy, trifluoromethoxy and the like), (iv) a di-$C_{1-4}$ alkylamino group (for example, dimethylamino group and the like), (v) a $C_{1-3}$ acyloxy group (for example, acetoxy group) or (vi) a hydroxyl group, especially halogens (having the meaning described above), a $C_{1-4}$ alkyl group (having the meaning described above) which may be substituted by a halogen, a $C_{1-4}$ alkoxy group (having the meaning described above) which may be substituted by a halogen.

In Formula [III] described above, an optionally substituted hydrocarbon group represented by $R^b$ has the meaning described above.

A hydrocarbon group represented by $R^9$ has the meaning described above.

In Formula [IV] shown above, W is —CH$_2$—, —CO— or —CS—, preferably —CH$_2$—, —CO—.

In Formula [IV] shown above, V is

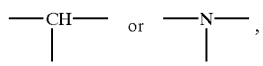

or W and V are taken together to form

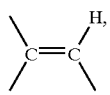

preferably, V is

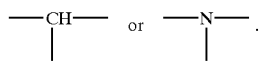

In Formula [IV] shown above, Y" is —CH$_2$—, —O—, —S—, —CO—, —CS— or —NR$^9$— (in which R$^9$ has the meaning described above), preferably, —CH$_2$—, —O—, —CO—, —NR$^{9a}$— (in which R$^{9a}$ is a C$_{1-6}$ alkyl group such as methyl, ethyl, propyl, isopropyl and the like), with —CH$_2$—, —O— being especially preferred.

In Formula [IV] shown above, U' is —NH—, —CH$_2$—, —CH$_2$NH—, preferably —NH—, —CH$_2$—.

Another preferred example of a compound represented by Formula [I] may, for example, be a compound represented by Formula [V]:

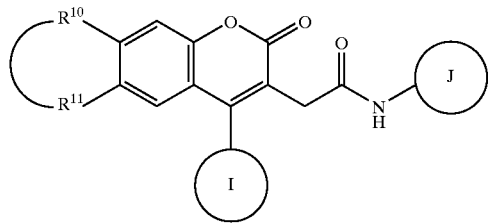

in which each of R$^{10}$ and R$^{11}$ is a hydrogen atom, halogen atom, optionally substituted linear hydrocarbon group or the both may be taken together with the adjacent carbon atoms to form an optionally substituted cyclic hydrocarbon group or a dihydrofuran ring which may be substituted by an oxo group, ring I is an optionally substituted benzene ring or optionally substituted pyridine ring, ring J is an optionally substituted benzene ring or optionally substituted pyridine ring (preferably, when R$^{10}$ is a hydrogen atom, then R$^{11}$ is a substituted linear hydrocarbon group), or a salt thereof, and each of R$^{10}$ and R$^{11}$ is preferably a hydrogen atom, halogen atom or optionally substituted linear hydrocarbon group or the both may be taken together with the adjacent carbon atoms to form an optionally substituted cyclic hydrocarbon group or a dihydrofuran ring which may be substituted by an oxo group.

"Linear hydrocarbon group" in "an optionally substituted linear hydrocarbon group" and "hydroxyl group which may be substituted by an optionally substituted linear hydrocarbon group" represented by R$^{10}$ and R$^{11}$ in Formula [V] shown above may, for example, be an alkyl group, alkenyl group and alkynyl group.

An alkyl group is a straight or branched group having 1 to 7 carbon atoms, preferably a straight or branched group having 1 to 4 carbon atoms, such as methyl, ethyl, propyl, isopropyl, butyl, isobutyl, sec-butyl, tert-butyl and the like.

An alkenyl group is an alkenyl group having 2 to 6 carbon atoms, such as ethenyl, propenyl, isopropenyl, butenyl, isobutenyl, sec-butenyl and the like, preferably an alkenyl group having 2 to 4 carbon atoms, such as ethenyl, propenyl, isopropenyl and the like.

An alkynyl group is an alkynyl group having 2 to 6 carbon atoms, such as ethynyl, propynyl, isopropynyl, butynyl, isobutynyl, sec-butynyl and the like, preferably an alkynyl group having 2 to 4 carbon atoms, such as ethynyl, propynyl, isopropynyl and the like.

A linear hydrocarbon group described above is preferably a straight or branched alkyl group having 1 to 6 carbon atoms, especially a straight or branched alkyl group having 1 to 4 carbon atoms such as methyl, ethyl, propyl, isopropyl, butyl, isobutyl, sec-butyl, tert-butyl and the like.

A substituent on "an optionally substituted linear hydrocarbon group" and "hydroxyl group which may be substituted by an optionally substituted linear hydrocarbon group" represented by R$^{10}$ and R$^{11}$ may be a substituent in "an optionally substituted linear hydrocarbon group" described above.

Each of R$^{10}$ and R$^{11}$-may, for example, be a halogen atom (e.g., fluorine atom, chlorine atom, bromine atom), optionally substituted C$_{1-7}$ alkyl group (preferably a C$_{1-4}$ alkyl group, such as methyl, ethyl and propyl, especially methyl), optionally substituted C$_{2-6}$ alkenyl group (for example, ethenyl) or hydroxyl group which may be substituted by an optionally substituted C$_{1-7}$ alkyl group (preferably, hydroxyl group, C$_{1-4}$ alkoxy group such as methoxy), with a halogen atom or an optionally substituted C$_{1-7}$ alkyl being preferred. "A C$_{1-7}$ alkyl group" in "an optionally substituted C$_{1-7}$ alkyl group" has an oxo group as a substituent, and when said oxo group is present in an α-position, then a C$_{1-7}$ alkanoyl group such as formyl and acetyl may be formed.

A preferred substituent on a C$_{1-7}$ alkyl group described above may for example be:
(i) a hydroxyl group,
(ii) a mono- or di-C$_{1-4}$ alkylamino group (e.g., dimethylamino, diethylamino),
(iii) an amino group substituted by a C$_{1-4}$ alkyl and a 5- to 9-membered heterocyclic group which contains 1 to 3 heteroatoms such as nitrogen, oxygen and sulfur atoms in addition to carbon atoms (for example, thienyl, furyl, pyridyl, pyrimidinyl, thiazolyl, benzothiazolyl, benzoisothiazolyl, benzoxazolyl, benzoisoxazolyl and the like) (e.g., methyl(2-pyridyl)amino),
(iv) an amino group substituted by a C$_{1-4}$ alkyl and a C$_{1-4}$ alkyl-carbonyl (e.g., methyl(methylcarbonyl)amino),
(v) an amino group substituted by a C$_{1-4}$ alkyl and a C$_{6-12}$ aryl-carbonyl (e.g., methyl(benzoyl)amino),
(vi) a mono- or di-C$_{1-4}$ alkoxy-C$_{1-4}$ alkyl-amino group (e.g., butoxypropylamino),
(vii) 5- to 9-membered cyclic amino group which may contain 1 to 3 heteroatoms such as oxygen and sulfur atoms in addition to nitrogen atoms (e.g., pyrrolidinyl, piperidinyl, piperazinyl, morpholinyl, 3,6-dihydropyridin-1(2H)-yl), optionally substituted by a C$_{6-12}$ aryl which may have 1 to 4 substituents selected from a C$_{1-4}$ alkyl (e.g., methyl), halogen atoms, hydroxy group and optionally halogenated C$_{1-4}$ alkyl (e.g., phenyl, 4-hydroxyphenyl, 4-chlorophenyl, 3-methylphenyl), C$_{1-4}$ alkylsulfonyl (e.g., methylsulfonyl), C$_{7-15}$ aralkyl (e.g., benzyl) which may have 1 to 4 substituents selected from, halogen atoms, hydroxy group and optionally halogenated C$_{1-4}$ alkyl, C$_{1-4}$ alkoxy-C$_{1-4}$ alkyl (for example, propoxyethyl and the like), 5- to 9-membered heterocyclic group which contains 1 to 3 heteroatoms such as nitrogen, oxygen and sulfur atoms in addition to carbon atoms (for example, piperidinyl, piperazinyl, morpholinyl, thienyl, furyl, pyridyl, pyrimidinyl, thiazolyl, benzothiazolyl, benzoisothiazolyl, benzoxazolyl, benzoisoxazolyl and the like), hydroxyl group and the like, (viii) a $C_{1-6}$ alkyl-carbonyloxy group (for example, methylcarbonyloxy, ethylcarbonyloxy, butylcarbonyloxy and the like), (ix) a 5- to 9-membered heterocyclic group which contains 1 to 3 heteroatoms such as nitrogen, oxygen and sulfur atoms in addition to carbon atoms (for example, thienyl, furyl, pyridyl, pyrimidinyl, thiazolyl, benzothiazolyl, benzoisothiazolyl, benzoxazolyl, benzoisoxazolyl and the like)-thio group (e.g., 2-pyridylthio) and the like.

A preferred substituent on said $C_{2-6}$ alkenyl group may, for example, be a $C_{1-4}$ alkoxy-carbonyl (e.g., methoxycarbonyl) and the like.

A cyclic hydrocarbon when $R^{10}$ and $R^{11}$ in Formula [V] shown above are taken together with the adjacent carbon atoms to form an optionally substituted cyclic hydrocarbon may, for example, be a saturated or unsaturated cyclic aliphatic hydrocarbon (for example, cycloalkane, cycloalkene, cycloalkadiene and the like) and aryl. Such a cycloalkane may, for example, be cyclopropane, cyclobutane, cyclopentane, cyclohexane, cycloheptane, cyclooctane, cyclononane and the like, preferably a $C_{3-7}$ cycloalkane such as cyclopropane, cyclobutane, cyclopentane, cyclohexane and the like. Said cycloalkene may, for example, be a $C_{5-6}$ cycloalkene such as cyclopentene, cyclohexene, cyclobutene, cyclopentene and the like. Said cycloalkadiene may, for example, be a $C_{5-6}$ cycloalkadiene such as 2,4-cyclopentadiene, 2,4-cyclohexadiene, 2,5-cyclohexadiene and the like.

An aryl described above may, for example, be a monocyclic or fused polycyclic aromatic hydrocarbon having 6 to 16 carbon atoms, such as benzene ring, naphthalene ring, anthracene ring, phenanthrene ring, acenaphthalene ring and the like, with a $C_{6-10}$ aryl such as benzene ring and naphthalene ring being especially preferred.

Preferred examples of a cyclic hydrocarbon which may be formed when $R^{10}$ and $R^{11}$ are taken together with the adjacent carbon atoms are a $C_{5-7}$ cyclic hydrocarbon, as well as a saturated or unsaturated cyclic aliphatic hydrocarbon (for example, cycloalkane, cycloalkene, cycloalkadiene and the like), especially, cyclopropane, cyclobutane, cyclopentane, cyclohexane, cycloheptane, cyclooctane, cyclononane and the like, with a $C_{3-7}$ cycloalkane such as cyclopropane, cyclobutane, cyclopentane and cyclohexane being particularly preferred.

A substituent which may be possessed by said cyclic hydrocarbon has the meaning similar to the substituent in "an optionally substituted hydrocarbon group" described above. A substituent on an unsaturated cyclic aliphatic hydrocarbon described above is preferably an oxo group or hydroxyl group.

A substituent on an optionally substituted benzene ring and optionally substituted pyridine ring represented by ring I and an optionally substituted benzene ring and optionally substituted pyridine ring represented by ring J in Formula [V] shown above has the meaning similar to the substituent in "an optionally substituted hydrocarbon group" represented by ring A described above.

Ring I is preferably a benzene ring which may be substituted by an alkyl group, halogenated alkyl group or a halogen atom, with a benzene ring which may be substituted by a $C_{1-6}$ alkyl group, halogenated $C_{1-4}$ alkyl group or halogen atom being especially preferred.

Ring J is preferably a benzene ring which may be substituted by a halogenated alkyl group or a halogen atom, with a benzene ring which may be substituted by a halogenated $C_{1-4}$ alkyl group or halogen atom being especially preferred.

A preferred example of a compound represented by Formula [I] or a salt thereof is a compound represented by Formula [VI]:

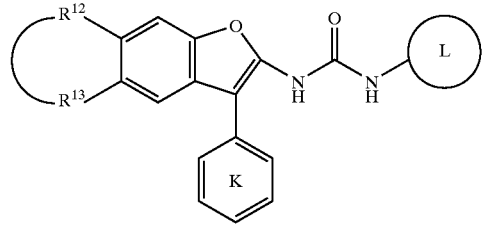

in which each of $R^{12}$ and $R^{13}$ is a hydrogen atom, halogen atom or optionally substituted linear hydrocarbon group, or the both may be taken together with the adjacent carbon atoms to form an optionally substituted cyclic hydrocarbon group,

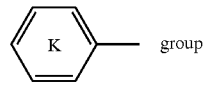 group is an optionally substituted phenyl group (preferably, except for 2-chlorophenyl ring and 2-fluorophenyl ring), ring L is an optionally substituted benzene ring or optionally substituted pyridine ring (preferably, when

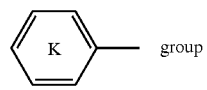 group is a phenyl group, then $R^{13}$ is not a methyl group, and

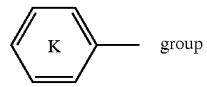 group is a 2-methylphenyl group, then $R^{13}$ is not a chlorine atom) or a salt thereof.

In Formula [VI] shown above, "an optionally substituted linear hydrocarbon group" represented by $R^{12}$ and $R^{13}$ is similar to "an optionally substituted linear hydrocarbon group" represented by $R^{10}$ and $R^{11}$ described above.

An optionally substituted cyclic hydrocarbon which may be formed when $R^{12}$ and $R^{13}$ are taken together with the adjacent carbon atoms has the meaning similar to "an optionally substituted cyclic hydrocarbon" which may be formed when $R^{10}$ and $R^{11}$ are taken together with the adjacent carbon atoms described above.

Preferred examples of a cyclic hydrocarbon in a cyclic hydrocarbon which may be formed when $R^{12}$ and $R^{13}$ are taken together with the adjacent carbon atoms are a $C_{5-7}$ cyclic hydrocarbon, as well as a saturated or unsaturated cyclic aliphatic hydrocarbon (for example, cycloalkane, cycloalkene, cycloalkadiene and the like), especially, cyclopropane, cyclobutane, cyclopentane, cyclohexane, cycloheptane, cyclooctane, cyclononane and the like, with a $C_{3-7}$ cycloalkane such as cyclopropane, cyclobutane, cyclopentane and cyclohexane being particularly preferred.

Each of $R^{12}$ and $R^{13}$ is preferably a halogen atom or a $C_{1-3}$ alkyl group.

In Formula [VI] shown above, "a substituent" on an optionally substituted phenyl group represented by Formula:

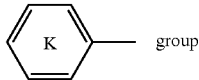

has the meaning similar to "a substituent" on an optionally substituted benzene ring represented by ring I shown above.

A preferred example of

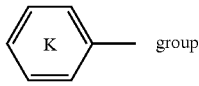

may, for example, be a phenyl group which may be substituted by a $C_{1-3}$ alkyl group.

In Formula [VI] shown above, "an optionally substituted benzene ring and optionally substituted pyridine ring" represented by ring L has the meaning similar to "an optionally substituted benzene ring and optionally substituted pyridine ring" represented by ring J shown above.

A preferred example of ring L may, for example, be a substituted benzene ring. Such a substituent has the meaning similar to the substituent which may be possessed by ring L described above.

A compound represented by Formula [I], [II], [III], [IV], [V] or [VI] in a free form and a pharmacologically acceptable salt thereof are encompassed in the present invention. When a compound represented by Formula [I], [II], [III], [IV], [V] or [VI] has an acidic group such as a carboxyl group, such a salt may be a salt with an inorganic base (e.g., alkaline metals such as sodium and potassium, alkaline earth metals such as calcium and magnesium, transition metals such as zinc, iron and copper) or an organic base (e.g., organic amines such as trimethylamine, triethylamine, pyridine, picoline, ethanolamine, diethanolamine, triethanolamine, dicyclohexylamine and N,N'-dibenzylethylenediamine, basic amino acids such as arginine, lysine and ornithine).

When a compound represented by Formula [I], [II], [III], [IV], [V] or [VI] has a basic group such as an amino group, it may form a salt with an inorganic or organic acid (e.g., hydrochloric acid, nitric acid, sulfuric acid, phosphoric acid, carbonic acid, bicarbonic acid, formic acid, acetic acid, propionic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like) as well as acidic amino acids such as aspartic acid, glutamic acid and the like.

A compound represented by Formula [I], [II], [III], [IV], [V] or [VI] or a salt thereof can be employed also as a prodrug. Said prodrug is a compound which is converted into a compound represented by Formula [I], [II], [III], [IV], [V] or [VI] or a salt thereof under a physiological condition in a living body as a result of a reaction with an enzyme or gastric acid, and thus a compound which undergoes an enzymatic oxidation, reduction or hydrolysis to form a compound represented by Formula [I], [II], [III], [IV], [V] or [VI] or a salt thereof and a compound which is hydrolyzed by gastric acid to form a compound represented by Formula [I], [II], [III], [IV], [V] or [VI] or a salt thereof. A prodrug for a compound represented by Formula [I], [II], [III], [IV], [V] or [VI] or a salt thereof may, for example, be a compound obtained by subjecting an amino group in a compound represented by Formula [I], [II], [III], [IV], [V] or [VI] or a salt thereof to an acylation, alkylation or phosphorylation when said compound has an amino group (e.g., a compound obtained by subjecting an amino group in a compound represented by Formula [I], [II], [III], [IV], [V] or [VI] or a salt thereof to an eicosanoylation, alanylation, pentylaminocarbonylation, (5-methyl-2-oxo-1,3-dioxolen-4-yl)methoxycarbonylation, tetrahydrofuranylation, pyrrolidylmethylation, pivaloyloxymethylation and t-butylation); a compound obtained by subjecting a hydroxyl group in a compound represented by Formula [I], [II], [III], [IV], [V] or [VI] or a salt thereof to an acylation, alkylation, phosphorylation or boration when said compound has a hydroxy group (e.g., a compound obtained by subjecting the hydroxyl group to an acetylation, palmitoylation, propanoylation, pivaloylation, succinylation, fumarylation, alanylation, dimethylaminomethylcarbonylation); a compound obtained by subjecting a carboxyl group in a compound represented by Formula [I], [II], [III], [IV], [V] or [VI] or a salt thereof to an esterification or amidation when said compound has a carboxyl group (e.g., a compound obtained by subjecting the carboxyl group to an ethylesterification, phenylesterification, carboxymethylesterification, dimethylaminoesterification, pivaloyloxymethylesterification, ethoxycarbonyloxyethylesterification, phthalidylesterification, (5-methyl-2-oxo-1,3-dioxolen-4-yl) methylesterification, cyclohexyloxycarbonylethylesterification and methylamidation) and the like. These prodrugs can be produced from a compound represented by Formula [I], [II], [III], [IV], [V] or [VI] or a salt thereof by a method known per se.

A prodrug for a compound represented by Formula [I], [II], [III], [IV], [V] or [VI] or a salt thereof may also be one which is converted into a compound represented by Formula [I], [II], [III], [IV], [V] or [VI] or a salt thereof under a physiological condition, such as those described in "IYAKUHIN no KAIHATSU (Development of Pharmaceuticals)", Vol.7, Design of Molecules, p.163–198, Published by HIROKAWA SHOTEN (1990).

A compound represented by Formulae [I], [II], [III], [IV], [V] or [VI] or a salt may be present as a hydrate or anhydride thereof.

A compound represented by Formulae [I], [II], [III], [IV], [V] or [VI] or a salt may be labeled with an isotope (e.g., $^3$H, $^{14}$C, $^{35}$S, $^{125}$I and the like).

Preferred examples of a compound represented by Formula [I] other than those represented by Formulae [II] to [VI] are those disclosed in EPA585913, EPA602598, JP-A-6-263736, JP-A-6-340647, JP-A-8-295667 and WO99-33825.

Among those compounds represented by Formula [I], the following compounds:

2-[7-Chloro-4-(3-chlorophenyl)-6-methyl-2-oxo-2H-chromen-3-yl]-N-[4-chloro-2-(trifluoromethyl)phenyl] acetamide;

2-[7-chloro-4-(3-chlorophenyl)-6-methyl-2-oxo-2H-chromen-3-yl]-N-[4-fluoro-2-(trifluoromethyl)phenyl] acetamide;

2-[7-chloro-4-(3-chloro-4-fluorophenyl)-6-methyl-2-oxo-2H-chromen-3-yl]-N-[4-chloro-2-(trifluoromethyl) phenyl]acetamide;

2-[7-chloro-4-(3-chloro-4-fluorophenyl)-6-methyl-2-oxo-2H-chromen-3-yl]-N-[4-fluoro-2-(trifluoromethyl) phenyl]acetamide;

2-[7-chloro-6-methyl-4-(3-methylphenyl)-2-oxo-2H-chromen-3-yl]-N-[4-chloro-2-(trifluoromethyl)phenyl] acetamide;

2-[7-chloro-6-methyl-4-(3-methylphenyl)-2-oxo-2H-chromen-3-yl]-N-[4-fluoro-2-(trifluoromethyl)phenyl]acetamide;
2-[7-chloro-2-oxo-4-phenyl-6-[(4-phenylpiperazin-1-yl)methyl]-2H-chromen-3-yl]-N-[4-chloro-2-(trifluoromethyl)phenyl]acetamide;
2-[7-chloro-2-oxo-4-phenyl-6-[(4-phenylpiperazin-1-yl)methyl]-2H-chromen-3-yl]-N-[4-fluoro-2-(trifluoromethyl)phenyl]acetamide;
2-[7-chloro-6-[[4-(4-chlorophenyl)-3,6-dihydropyridin-1(2H)-yl]methyl]-2-oxo-4-phenyl-2H-chromen-3-yl]-N-[4-chloro-2-(trifluoromethyl)phenyl]acetamide;
2-[7-chloro-6-[[4-(4-chlorophenyl)-3,6-dihydropyridin-1(2H)-yl]methyl]-2-oxo-4-phenyl-2H-chromen-3-yl]-N-[4-fluoro-2-(trifluoromethyl)phenyl]acetamide;
2-[7-chloro-6-[[4-(3-methylphenyl)piperidin-1-yl]methyl]-2-oxo-4-phenyl-2H-chromen-3-yl]-N-[4-chloro-2-(trifluoromethyl)phenyl]acetamide;
2-[7-chloro-6-[[4-(3-methylphenyl)piperidin-1-yl]methyl]-2-oxo-4-phenyl-2H-chromen-3-yl]-N-[4-fluoro-2-(trifluoromethyl)phenyl]acetamide; or a salt thereof are employed preferably.

A compound represented by Formula [I] or a salt thereof encompasses any known compounds and novel compounds. Such known compounds [II], [III] and [IV] and their salts are disclosed for example in EPA585913, EPA602598 and JP-A-6-263736 and the like, the disclosure in which are followed to produce the compounds. Said novel compounds [V] and [VI] and their salts can be produced for example by the following methods. Thus, a compound [I] or a salt thereof can be produced by known methods for producing Compounds [II], [III] and [IV] described above or by the methods for producing Compounds [V] and [VI] described below, or any analogous methods.

A compound [V] or a salt thereof can be produced, as shown below, by reacting a corresponding coumarineacetic acid derivative [VII], or a salt thereof or a derivative thereof which is reactive at its carboxyl group, with a compound represented by Formula [VIII]:

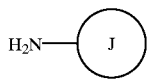

wherein each symbol is as defined above or a salt thereof. Such a reactive derivative of a carboxylic acid may, for example, be an acid halide (for example, chloride, bromide and the like), acid anhydride, mixed acid anhydride (for example, anhydride with methyl carbonate, anhydride with ethyl carbonate, anhydride with isobutyl carbonate and the like), activated ester (for example, ester with hydroxysuccinimide, ester with 1-hydroxybenzotriazole, ester with N-hydroxy-5-norbornene-2,3-dicarboxyimide, ester with p-nitrophenol, ester with 8-oxyquinloine and the like), with an acid halide being especially preferred.

A compound [V] or a salt thereof can be produced also by reacting a coumarineacetic acid derivative [VII] or a salt thereof with a compound represented by Formula [VIII] or a salt thereof in the presence of a coupling reagent. Such a coupling reagent may, for example, be a carbodiimide (for example, dicyclohexylcarbodiimide, N-[3-(dimethylamino)propyl]-N'-ethylcarbodiimide, N-cyclohexyl-N'-(2-morpholin-4-ylethyl)carbodiimide, N-cyclohexyl-N'-[4-(diethylamimo)cyclohexyl]carbodiimide), carbonyldiimidazole, N-ethyl-5-phenylisoxazolium-3'-sulfonate, N-ethyl-2'-hydroxybenzisoxazolium trifluoroborate, 2-ethoxy-1-ethoxycarbonyl-1,2-dihydroquinoline, 2-isobutyloxy-1-isobutyloxycarbonyl-1,2-dihydroquinoline, (benzotriazolyl-N-hydroxytrisdiethylaminophosphonium hexafluorophosphide salt, diphenylphosphoryl azide and the like. In some cases, a carbodiimide can affect the reaction advantageously when combined with additives. Such additives are N-hydroxysuccinimide, 1-hydroxybenzotriazole, 3-hydroxy-4-oxo-3,4-dihydro-1,2,3-benzotriazine, N-hydrpxy-5-norbornene-2,3-dicarboxylic acid imide, ethyl 2-hydroxyimino-2-cyanoacetate, 2-hydroxyimino-2-cyanoacetamide and the like.

A salt of a compound [VII] is similar to the salt of a compound [I] described above.

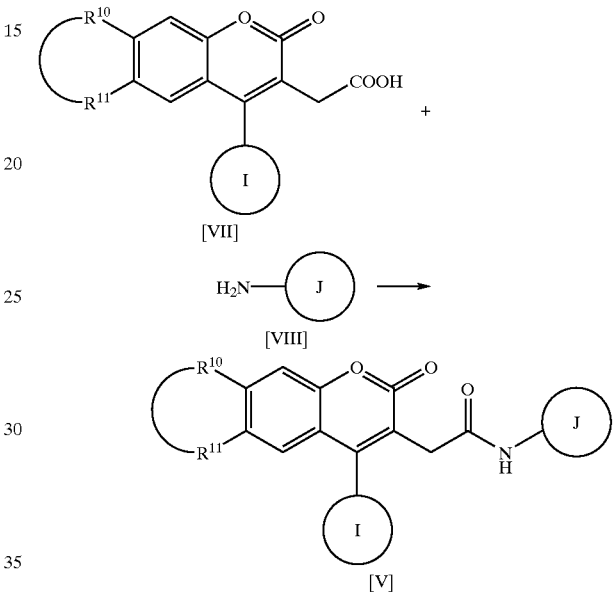

This reaction is conducted usually in a solvent by which the reaction is not affected adversely (for example, a halogenated hydrocarbon such as chloroform, dichloromethane, ethyl ether, tetrahydrofuran, dioxane, dimethoxyethane, ethyl acetate, benzene, toluene, pyridine, N,N-dimethylformamide and the like, ether, ester, hydrocarbon, aromatic amine, amide and the like). This reaction can be conducted in the presence or absence of a base. The reaction temperature is usually about −10° C. to 120° C., preferably about 0° C. to 100° C. The reaction time is usually about 5 minutes to 48 hours, preferably about 0.5 to 24 hours. The amount of a compound [VIII] or a salt thereof is about 1 to 5 molar equivalents, preferably about 1 to 3 molar equivalents, per 1 mole of a compound [VII] or a salt thereof or a reactive derivative thereof. The base may, for example, be an alkylamine such as triethylamine, a cyclic amine such as N-methylmorpholine and pyridine, an aromatic amine such as N,N-dimethylaniline and N,N-diethylaniline, an alkaline metal carbonate such as sodium carbonate and potassium carbonate, an alkaline metal hydrogen carbonate such as sodium hydrogen carbonate and potassium hydrogen carbonate and the like, and the amount of which is about 1 to 5 molar equivalents, preferably about 1 to 3 molar equivalents per 1 mole of a compound [VIII] or a salt thereof. When using a solvent which is immiscible with water, then a suitable amount of water may be added to the reaction system to conduct the reaction in a biphasic system. When using a coupling reagent, it is preferable usually to conduct the reaction under an anhydrous condition. The amount of said coupling reagent is about 1 to 10 molar equivalents, preferably about 1 to 3 molar equivalents per 1 mole of a compound [VII] or a salt thereof. When an additive is employed, the amount is about 1 to 5 molar equivalents, preferably about 1 to 2 molar equivalents per 1 mole of the coupling regent.

A starting compound [VII] or a salt thereof employed in the reaction described above can be obtained for example by the method described in EPA585913 or an analogous method.

A starting compound [VII] or a salt thereof employed in the reaction described above can be obtained also by the methods described below.

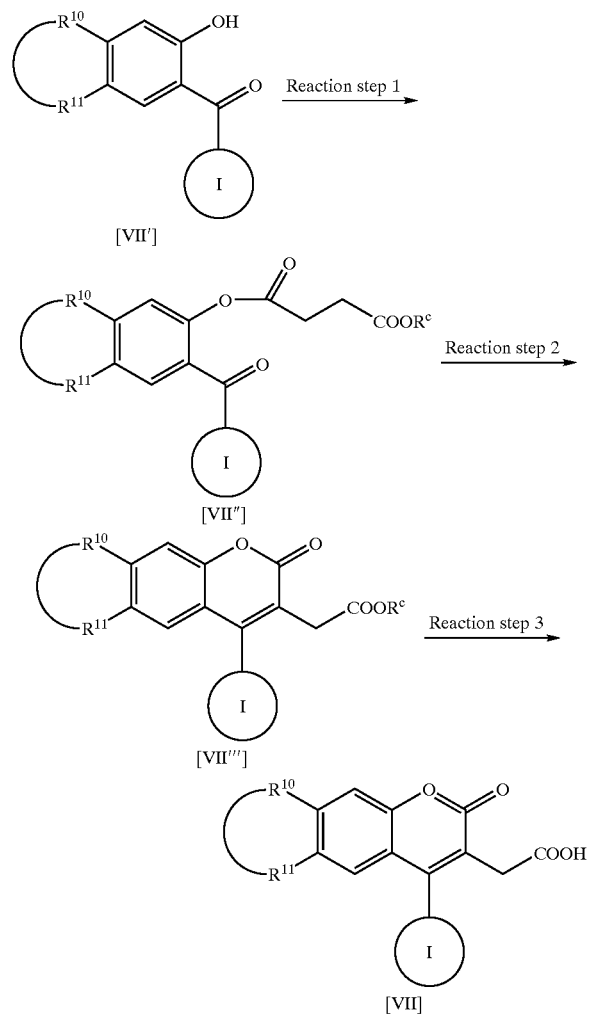

wherein $R^c$ is an alkyl group (methyl, ethyl, propyl, t-butyl and the like and other symbols are as defined above.

Reaction step 1 is accomplished by condensing a compound [VII'] or a salt thereof with a reactive derivative of a succinic acid monoester.

A reactive derivative of a succinic acid monoester may, for example, be an acid halide (for example, an acid chloride) of a succinic acid monoalkylester (e.g., methyl ester, ethyl ester, propyl ester), with ethylsuccinicyl chloride being employed preferably. The amount of a reactive derivative of a succinic acid monoester employed is usually an equimolar amount to about 10-fold molar amount, preferably an equimolar amount to about 3-fold molar amount, based on a compound [VII'] or a salt thereof. Usually, said reaction is conducted advantageously in the presence of a base, and such a base is an organic or inorganic base. Such an organic base may, for example, be a tertiary amine (for example, triethylamine, diisopropylethylamine, diazabicycloundecene and the like). An inorganic base may, for example, be an alkaline metal hydroxide such as lithium hydroxide, sodium hydroxide, potassium hydroxide and the like; an alkaline metal carbonate such as sodium carbonate, potassium carbonate, cesium carbonate and the like; an alkaline metal hydrogen carbonate such as sodium hydrogen carbonate, potassium hydrogen carbonate; an alkaline metal hydride such as sodium hydride and potassium hydride. The amount of a base employed is an equimolar amount to about 10-fold molar amount, preferably an equimolar amount to about 3-fold molar amount, based on a compound [VII'] or a salt thereof.

Said reaction is conducted advantageously in a solvent. Such a solvent is a solvent by which the reaction is not affected adversely, including a hydrocarbon (for example, pentane, hexane, cyclohexane, benzene, toluene and the like), a halogenated hydrocarbon (for example, dichloromethane, chloroform and the like), an ether (for example, diethyl ether, tetrahydrofuran, dioxane and the like), an amide (for example, N,N-dimethylformamide, hexamethyl phosphoryl triamide and the like), an urea (for example, 1,3-dimethyl-3,4,5,6-tetrahydro-2(1H)-pyrimidine and the like), a nitrile (for example, acetonitrile, propionitrile and the like). Any of these solvents can be employed alone or in combination with each other in a suitable ratio. The amount of a solvent employed is usually about 1 to 100 ml, preferably about 10 to 50 ml per 1 g of a compound [VII'] or a salt thereof. The reaction temperature is usually about −20° C. to the boiling temperature of the solvent employed for the reaction, preferably about 25° C. to 100° C.

The reaction time may vary depending on the types of the base and the reaction solvent employed and the reaction temperature, it is about 10 minutes to 24 hours, preferably about 20 minutes to 12 hours.

Reaction step 2 is accomplished by treating a compound [VII"] with a base. Said base may, for example, be those exemplified in Reaction step 1, and the amount of a base employed is usually about 0.1-fold molar amount to 10-fold molar amount, preferably about 0.1-fold molar amount to 1-fold molar amount based on a compound [VII"] or a salt thereof.

Said reaction is conducted advantageously in a solvent. Such a solvent is a solvent by which the reaction is not affected adversely, including a hydrocarbon (for example, pentane, hexane, cyclohexane, benzene, toluene and the like), a halogenated hydrocarbon (for example, dichloromethane, chloroform and the like), an ether (for example, diethyl ether, tetrahydrofuran, dioxane and the like), an amide (for example, N,N-dimethylformamide, hexamethyl phosphoryl triamide and the like), an urea (for example, 1,3-dimethyl-3,4,5,6-tetrahydro-2(1H)-pyrimidine and the like), a nitrile (for example, acetonitrile, propionitrile and the like). Any of these solvent can be employed alone or in combination with each other in a suitable ratio. The amount of a solvent employed is usually about 1 to 100 ml, preferably about 10 to 50 ml per 1 g of a compound [VII'] or a salt thereof. The reaction temperature is usually about 20° C. to the boiling temperature of the solvent employed for the reaction, preferably about 25° C. to 120° C.

The reaction time may vary depending on the types of the base and the reaction solvent employed and the reaction temperature, it is about 30 minutes to 24 hours, preferably about 1 hour to 12 hours.

Said reaction may sometimes be accomplished advantageously by removing water generated during the reaction for example by using a Dien-Stark azeotropic dehydration device.

It is also possible that the reaction step 1 and the reaction step 2 can be accomplished in one pot. For example, by using as a reactive derivative of a succinic acid monoester an acid halide (e.g., acid chloride and the like) of a succinic acid monoalkyl ester (e.g., methyl ester, ethyl ester, propyl ester) and as a base a tertiary amine (for example, triethylamine, diisopropylethylamine, diazabicycloundecene and the like) in excess, a compound [VII'''] or a salt can be produced all at once from a compound [VII''] or a salt thereof. The amount of an acid halide employed in such a case is usually about 1.5-fold molar amount to 10-fold molar amount, preferably about 1.5-fold molar amount to 3-fold amount based on a compound [VII''] or a salt thereof. The amount of a base employed is usually about 2-fold molar amount to 10-fold molar amount, preferably about 2-fold molar amount to 5-fold amount based on a compound [VII''] or a salt thereof.

Said reaction is conducted advantageously in a solvent. Such a solvent is a solvent by which the reaction is not affected adversely, and the type and the amount of a solvent employed are similar to those the reaction step 1. The reaction temperature is usually about 20° C. to the boiling temperature of the solvent employed for the reaction, preferably about 25° C. to 60° C. The reaction time may vary depending on the types of the acid halide and the base, the type of the reaction solvent and the reaction temperature, it is about 30 minutes to 24 hours, preferably about 30 minutes to 4 hours.

Reaction step 3 is accomplished by treating a compound [VII'''] with an acid or base.

Such an acid may, for example, be an organic acid (for example, formic acid, acetic acid, trichloroacetic acid, trifluoroacetic acid, benzensulfonic acid, p-toluensulfonic acid and the like), or an inorganic acid (for example, hydrochloric acid, hydrobromic acid, sulfuric acid, nitric acid, phosphoric acid and the like), any of which may be employed alone or in combination with each other in a suitable ratio. Said base may, for example, be an alkaline metal hydroxide (for example, lithium hydroxide, sodium hydroxide, potassium hydroxide and the like), an alkaline metal carbonate (For example, sodium carbonate, potassium carbonate, cesium carbonate and the like), an alkaline metal hydrogen carbonate (for example, sodium hydrogen carbonate, potassium hydrogen carbonate and the like). The amount of an acid or base employed is usually about 1 molar amount to 100-fold molar amount, preferably about 1 molar amount to 10-fold molar amount based on a compound [VII'''].

Said reaction is conducted advantageously in a solvent. Such a solvent is a solvent by which the reaction is not affected adversely, including a hydrocarbon (for example, pentane, hexane, cyclohexane, benzene and the like), a lower alcohol (for example, methanol, ethanol, propanol and the like), an ether (for example, diethyl ether, tetrahydrofuran, dioxane and the like), an amide (for example, N,N-dimethylformamide, hexamethyl phosphoryl triamide and the like), an urea (for example, 1,3-dimethyl-3,4,5,6-tetrahydro-2(1H)-pyrimidine and the like). In a reaction using an acid, an acid described above can be employed as a solvent. Any of these solvent can be employed alone or in combination with each other in a suitable ratio, or in combination with water. The amount of a solvent employed is usually about 1 to 100 ml, preferably about 10 to 50 ml per 1 g of a compound [VII'''] or a salt thereof. The reaction temperature is usually about −20° C. to the boiling temperature of the solvent employed for the reaction, preferably about 15° C. to 120° C. The reaction time may vary depending on the types of the acid and the reaction solvent employed and the reaction temperature, it is about 10 minutes to 24 hours, preferably about 30 minutes to 12 hours.

Furthermore, a coumarinamide condensed with a cycloalkane which has oxo group can be synthesized also by subjecting a coumarinamide condensed with a cycloalkane to an oxidation reaction at an appropriate stage of the synthesis. Such an oxidation reaction can be accomplished using an oxidant (for example, permanganate, chromate and the like) by a method known per se [for example, A. B. Smith, III, et. al., The Journal of Organic Chemistry, Vol.50, p3239–3241, 1985).

Salts of the compounds [VII'], [VII''] and [VII'''] employed in the reactions described above are similar to those salts of a compound [I] described above.

A compound [VI] or a salt thereof can be produced by, for example, the following method [1] or [2] shown below.

Method [1]

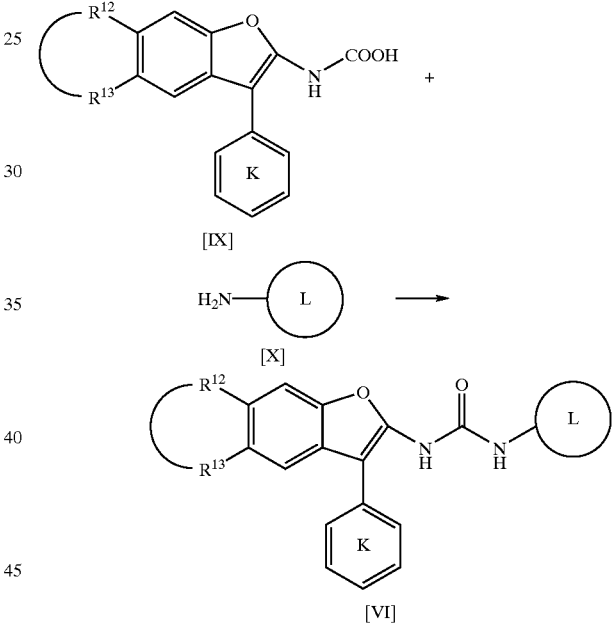

wherein each symbol is as defined above.

The reaction of a carboxylic acid represented by Formula [IX] or a salt thereof or a reactive derivative thereof with a compound represented by Formula [X] or a salt thereof is an amide bond- or urea bond-forming reaction, which can be accomplished by various known method. For example, when reacting a compound [IX] or a salt thereof (for example, a salt with an alkaline metal such as sodium, potassium, magnesium and the like, alkaline earth metal and the like) with a compound [X] or a salt thereof (for example, a salt with an inorganic acid such as hydrochloric acid, sulfuric acid and the like, a salt with an organic acid such as methanesulfonic acid, benzenesulfonic acid, toluenesulfonic acid, oxalic acid, fumaric acid, maleic acid and the like), it is preferable usually that an appropriate condensing agent is employed or that such a compound [IX] or a salt thereof is once derivatized to its reactive derivative and subsequently reacted with a compound [X] or a salt thereof. Such a condensing agent may, for example, be dicyclohexylcarbodiimide, 1-(3-dimethylaminopropyl)-3-ethylcarbodiimide hydrochloride, diethyl cyanophosphate, diphenylphosphoryl azide and the like. When using such a condensing agent, the reaction can be conducted advantageously in a solvent by which the reaction is not affected adversely (for example, ethers, esters, halogenated hydrocarbons, hydrocarbons, amides, sulfoxides such as tetrahydofuran, dioxane, dimethoxyethane, ethyl acetate, dichloromethane, 1,2-dichloroethane, benzene, toluene, N,N-dimethylformamide, dimethylsulfoxide and the like). This reaction can be promoted in the presence of a base, and the reaction is conducted at a temperature of about −10° C. to 100° C., preferably about 0° C. to 60° C. The reaction time is usually about 1 to 96 hours, preferably about 1 to 72 hours. The amounts of a compound [IX] or a salt thereof and a condensing agent employed are about 1 to 5 molar equivalents, preferably about 1 to 3 molar equivalents per 1 mole of a compound [X] or a salt thereof. A base employed may, for example, be an alkylamine such as triethylamine, cyclic amine such as N-methylmorpholine and pyridine, and the amount employed is about 1 to 5 molar equivalents, preferably about 1 to 3 molar equivalents per 1 mole of a compound [IX] or a salt thereof.

A reactive derivative of a compound [IX] may, for example, be an acid halide (for example, chloride, bromide and the like), acid anhydride, mixed acid anhydride (for example, anhydride with methyl carbonate, anhydride with ethyl carbonate, anhydride with isobutyl carbonate and the like), activated ester (for example, ester with hydroxysuccinimide, ester with 1-hydroxybenzotriazole, ester with N-hydroxy-5-norbornene-2,3-dicarboxyimide, ester with p-nitrophenol, ester with 8-oxyquinloine and the like). The reaction between a compound [IX] or a salt thereof and a reactive derivative of a compound [X] is conducted usually in a solvent (for example, halogenated hydrocarbons, ethers, esters, hydrocarbons and amides such as chloroform, dichloromethane, 1,2-dichloroethane, ethyl ether, tetrahydrofuran, dioxane, dimethoxyethane, ethyl acetate, benzene, toluene, pyridine, N,N-dimethylformamide and the like). This reaction can be promoted in the presence of a base. The reaction is conducted at a temperature of about −10° C. to 120° C., preferably about 0° C. to 100° C. The reaction time is usually about 0.5 to 48 hours, preferably about 1 to 24 hours. The amount of a compound [X] or a salt thereof employed is about 1 to 5 molar equivalents, preferably about 1 to 3 molar equivalents per 1 mole of a reactive derivative of a compound [IX]. A base employed may, for example, be an alkylamine such as triethylamine, a cyclic amine such as N-methylmorpholine and pyridine, an aromatic amine such as N,N-dimethylaniline and N,N-diethylaniline, an alkaline metal carbonate such as sodium carbonate and potassium carbonate, an alkaline metal hydrogen carbonate such as sodium hydrogen carbonate and potassium hydrogen carbonate, and the amount employed is about 1 to 5 molar equivalents, preferably about 1 to 3 molar equivalents per 1 mole of a compound [IX] or a reactive derivative thereof. When using a solvent which is immiscible with water in this reaction, water may be added in a suitable ratio to the reaction system to perform the reaction in a biphasic system.

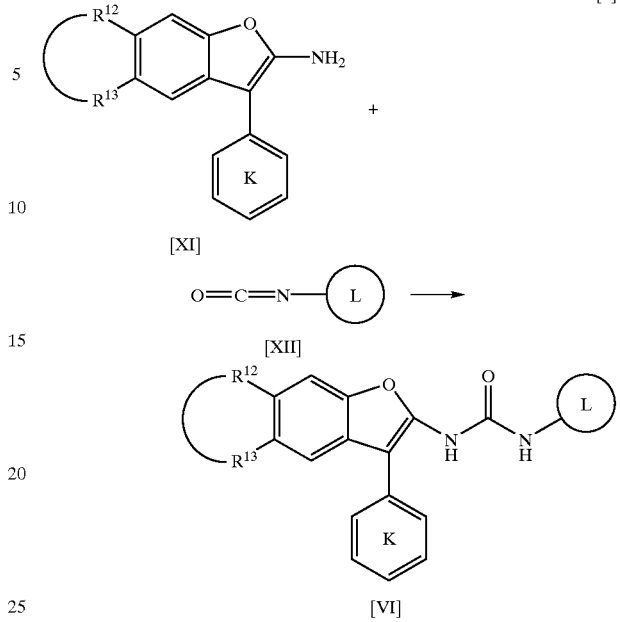

Method [2]

wherein each symbol is as defined above.

This method is a method for forming a urea derivative by reacting an amine derivative compound [XI] or a salt thereof (e.g., salt with a mineral acid such as hydrochloric acid, sulfuric acid and the like, a salt with an organic acid such as methanesulfonic acid, benzenesulfonic acid, toluenesulfonic acid, oxalic acid, fumaric acid, maleic acid and the like) with an isocyanate derivative compound [XII]. In this method, a reaction using such an isocyanate form [XII] and a compound [XI] or a salt thereof yields an urea derivative. While this reaction can be conducted without using any solvent, it is effective to conduct the reaction in a solvent. Such a solvent may be any solvent provided that it does not interfere with the reaction, and is preferably an ether (e.g., diethyl ether, diisopropyl ether, tetrahydrofuran, dioxane, dimethoxyethane and the like), an aromatic hydrocarbon (e.g., benzene, toluene, xylene and the like), an ester (e.g., methyl acetate, ethyl acetate and the like), an amide (e.g., N,N-dimethylformamide and the like), a sulfoxide (e.g., dimethyl sulfoxide and the like). When using a compound [XII] in a form of a salt, the reaction can be accomplished advantageously by adding a desalting agent if desired. Such a desalting agent may, for example, be a tertiary amine such as trimethylamine, triethylamine, N-methylmorpholine and the like, and an aromatic amine such as pyridine, picoline and N,N-dimethylaniline. The amount of such a desalting agent employed is about 1 to 5 molar equivalents, preferably about 1 to 3 molar equivalents per 1 mole of a salt of a compound [XII]. The reaction temperature is usually about −10° C. to 180° C., preferably about 0° C. to 120° C. The reaction time is usually about 15 minutes to 40 hours, preferably about 30 minutes to 20 hours. The amount of a compound [XII] or a salt thereof employed is about 1 to 5 molar equivalents, preferably about 1 to 3 molar equivalents per 1 mole of a compound [XI] or a salt thereof.

A starting compound [IX], [XI] or a salt thereof employed in the reaction described above can be obtained for example by the method described in EPA602598 or an analogous method.

In each reaction for producing a compound [V], [VI] or a salt thereof described above and each reaction for synthesizing a starting compound, a starting compound having an amino group, carboxy group or hydroxy group as its substituent may be present as a compound in which a protective group employed ordinarily in a peptide chemistry has been introduced into such a substituent, and an intended compound can be obtained by deprotection if necessary after the reaction.

A protective group for an amino group may, for example, be a formyl or each optionally substituted $C_{1-6}$ alkyl-carbonyl (for example, acetyl, ethylcarbonyl and the like), phenylcarbonyl, $C_{1-6}$ alkyl-oxycarbonyl (for example, methoxycarbonyl, ethoxycarbonyl and the like), phenyloxycarbonyl, $C_{7-10}$ aralkyl-carbonyl (for example, benzylcarbonyl), trityl, phthaloyl, N,N-dimethylaminomethylene and the like. Its substituent may, for example, be a halogen atom (for example, fluorine, chlorine, bromine, iodine), $C_{1-6}$ alkyl-carbonyl (for example, methylcarbonyl, ethylcarbonyl, butylcarbonyl and the like), nitro and the like, and the number of the substituents may be 1 to 3.

A protective group for a carboxy may, for example, be each optionally substituted $C_{1-6}$ alkyl (for example, methyl, ethyl, n-propyl, i-propyl, n-butyl, tert-butyl and the like), phenyl, trityl, silyl and the like. Its substituent -may, for example, be a halogen atom (for example, fluorine, chlorine, bromine, iodine), formyl, $C_{1-6}$ alkyl-carbonyl (for example, acetyl, ethylcarbonyl, butylcarbonyl and the like), nitro group and the like, and the number of the substituents may be 1 to 3.

A protective group for a hydroxy may, for example, be each optionally substituted $C_{1-6}$ alkyl (for example, methyl, ethyl, n-propyl, i-propyl, n-butyl, tert-butyl and the like), phenyl, $C_{7-10}$ aralkyl (for example, benzyl and the like), formyl, $C_{1-6}$ alkyl-carbonyl (for example, acetyl, ethylcarbonyl and the like), phenyloxycarbonyl, benzoyl, $C_{7-10}$ aralkyl-carbonyl (for example, benzylcarbonyl), pyranyl, furanyl, silyl and the like. Its substituent may, for example, be a halogen atom (for example, fluorine, chlorine, bromine, iodine and the like), $C_{1-6}$ alkyl (for example, methyl, ethyl, n-propyl), phenyl, $C_{7-10}$ aralkyl (for example, benzyl and the like), nitro and the like, and the number of the substituents may be 1 to 4.

A deprotection method may be a method known per se on an analogous method, for example, a treatment with an acid, base, reduction, UV, hydrazine, phenylhydrazine, sodium N-methyldichiocarbamate, tetrabutylammonium fluoride, palladium acetate and the like.

A compound [V], [VI] or a salt thereof obtained by a method described above can be isolated and purified by an ordinary separation means such as recrystallization, distillation and chromatography. When an inventive compound [V] or [VI] thus obtained is in a free form, it can be converted into a salt by a method known per se or an analogous method (for example, neutralization), while a compound [V] or [VI] which is obtained in the form of a salt can be converted into a free form or another salt by a method known per se or an analogous method.

Since each of inventive compounds [I], [II], [III], [IV], [V], [VI] and their salts and prodrug (hereinafter abbreviated as inventive compounds) has a low toxicity and also is safe while having a lipid-rich plaque regressing effect, it can be employed as a prophylactic or therapeutic agent in mammals (for example, mouse, rat, rabbit, dog, cat, cattle, pig, monkey, human and the like) against acute coronary artery syndrome such as acute myocardial infarction, unstable angina and the like, peripheral artery occlusion, restenosis after percutaneous transluminal coronary angioplasty (PTCA), ischemic heart disease such as myocardial infarction and angina pectoris, arteriosclerosis, intermittent claudication, apoplexy (cerebral infarction, cerebral embolism, cerebral hemorrhage and the like), lacunar infarction, cerebrovascular dementia, and is useful as a plaque regressing agent.

Each of novel compounds [V], [VI] and their salts has an ACAT inhibiting effect (preferably macrophage ACAT inhibiting effect, ACAT of subtype 1 inhibiting effect) similarly to known compounds [I], [II], [III], [IV] and their salts, and has a low toxicity similarly to [I], [II], [III], [IV] and their salt, and each of the novel compounds [V], [VI] and their salts and prodrug can be employed as a safe prophylactic or therapeutic agent in mammals (for example, mouse, rat, rabbit, dog, cat, cattle, pig, monkey, human and the like) against hypercholesteremia, atherosclerosis and diseases caused thereby (for example, ischemic heart disease such as myocardial infarction, cerebrovascular impairment such as cerebral infarction and apoplexy) similarly to known compounds [I], [II], [III], [IV] and their salts and prodrug.

Also according to the invention, an arteriosclerotic focus progression inhibitor comprising a compound having a lipid-rich plaque regressing effect or a salt thereof (preferably a compound of the present invention) is provided, and such an progression inhibitor is employed preferably in combination with an HMG-CoA reductase inhibitor.

In the treatment of each of the diseases listed above, a compound of the present invention may be employed alone in the treatment, or may be combined with other pharmaceutical components such as other hypolipidemic agent or hypocholesteremic agent, myocardial protecting agent, coronary artery disease treating agent, diabetes treating agent, thyroid dysfunction treating agent, nephrotic syndrome treating agent, osteoporosis treating agent or chronic renal failure treating agent, and in such a case it is preferable that each of these compounds is administered in an oral formulation, or in a suppository as a rectal formulation if desired. In such a case, a possible compound to be combined may, for example, be a fibrate [for example, clofibrate, bezafibrate, gemfibrosil and the like], nicotinic acid, derivatives and analogues thereof [e.g., acipimox and probcol], bile acid-binding resin [e.g., cholestylamine, cholestipol and the like], cholesterol absorption inhibiting compound [e.g., sitosterol, neomycin and the like], cholesterol biosynthesis inhibiting compound [e.g., an HMG-COA reductase inhibitor such as lovastatin, simvastatin, pravastatin and the like], squalene epoxidase inhibiting agent [e.g., NB-598 and analogues and the like].

Still other components to be combined are oxidesqualene-lanosterol cyclase, such as a decalin derivative, azadecalin derivative and indane derivative.

Also when combining with:

Diabetes treating agent [actos, lodiglitazon, kinedak, penfill, humalin, euglucon, glimicron, daonil, novolin, monotard, insulins, glucobay, dimelin, rastinon, bacilcon, deamelin S, Iszilins]; hypothyroidism treating agent [dried thyroid gland (thyreoid), levothyroxine sodium (thyradin S), liothyronidin sodium (thyronine, thyromin);

Nephrotic syndrome treating agent: prednisolone (Predonine), prednisolone succinate sodium (Predonine), methylprednisolone succinate sodium (Solu medrol), betamethasone (rinderon)]; anticoagulating agent [dipyridamole (Persantin), dilazep hydrochloride (comelian), ticlopidine, clopidogrel, Xa inhibitor]; chronic renal failure treating agent [diuretics [e.g., furosemide (lasix), bumetamide (lunetron), azosemide (diart)], hypotensive agent (e.g., ACE inhibitor, (enalapril maleate (renivase)) and Ca antagonist (manidipine), α-receptor blocker, AII antagonist (candesartan)]; an oral administraiton is preferred.

In view of the lipid-rich plaque regressing effect, the compound of the present invention is suitable for preventing and treating a thrombus formation. For this purpose, it is employed alone or in combinaiton with a known therapeutic agent listed below and administred preferably via an oral route.

Thrombus formation preventing agent: anticoagulating agent [e.g., heparin sodium, heparin potassium, warfarin potassium (warfarin), Xa inhibitor], thrombolytic agent [e.g., tPA, urokinase], antiplatelet agent [e.g., asprin, sulfinpyrazone (anturan), dipyridamole (persantin), ticlopidine (panaldine), cilostazol (pletal), GPIIb/IIIa antagonist (ReoPro)]; Coronary vasodilating agent: nifedipine, diltiazem, nicorandil, nitrous acid agent; Myocardial protecting agent: Cardiac ATP-K antagonist, endoserine antagonist, urotensin antagonist and the like. An inventive compound can be given orally or parenterally, by injection, infusion, inhalation, rectal administration, or topical administration, and can be used as it is or in a pharmaceutical formulation (for example, powder, granule, tablet, pill, capsule, injection, syrup, emulsion, elixir, suspension, solution and the like). Thus, at least one inventive compound can be employed alone or in a mixture with a pharmaceutically acceptable carrier (adjuvant, excipient, auxiliary agent and/ or diluent and the like).

A pharmaceutical composition can be formulated in accordance with an ordinary method. Such a formulation can be produced usually by mixing/kneading an active component with additives such as an excipient, diluent and carrier. In this specification, a parenteral administration means to include subcutaneous injection, intravenous injection, intramuscular injection, intraperitoneal injection or dripping infusion and the like. A formulation for injection such as aseptic aqueous suspension or oily suspension for injection can be produced using a suitable dispersing agent or wetting agent and a suspending agent by a method known in the art. Such an aseptic formulation for injection may be an aseptic injectable solution or suspension in a diluent or solvent which can be non-toxic and administered parenterally, including an aqueous solution. An acceptable vehicle or solvent which can be employed may, for example, be water, Ringer's solution, isotonic saline and the like. An aseptic non-volatile oil can also be used usually as a solvent or suspending medium. For such purpose, any non-volatile oil or fatty acid can be employed, including naturally occurring or synthetic or semi-synthetic fatty oil or fatty acid, as well as naturally occurring or synthetic or semi-synthetic mono- or di- or tri-glycerides.

A suppository for rectal administration can be produced by mixing an active ingredient with a suitable non-irritating excipient which is solid at ambient temperature but becomes liquid at the temperature in an intestinal tract to melt in rectum whereby releasing the active ingredient, such as cocoa butter and polyethylene glycols.

A suitable base (e.g. polymer of butyric acid, polymer of glycolic acid, copolymer of butyric acid and glycolic acid, mixture of a polymer of butyric acid and a polymer of glycolic acid, polyglycerol fatty acid ester and the like) may be combined to form a sustained release formulation.

A solid dosage form for oral administration may, for example, be a powder, granule, tablet, pill, capsule and the like, as described above. The formulation of such a dosage form can be produced by mixing and/or kneading an active compound with at least one of the additives, such as sucrose, milk sugar (lactose), cellulosic saccharide, mannitol (D-mannitol), maltitol, dextran, starches (e.g., corn starch), microcrystalline cellulose, agar, alginates, chitins, chitosans, pectins, tragacanth gums, gum arabic, gelatins, collagens, casein, albumin, synthetic or semi-synthetic polymers or glycerides. Such a dosage form can further contain additives as usual, including inert diluents, lubricants such as magnesium stearate, preservatives such as parabens and sorbic acid, antioxidants such as ascorbic acid, α-tocopherol and cysteine, disintegrants (e.g., croscarmellose sodium), binder (e.g., hydroxypropyl cellulose), thickening agents, buffering agents, sweeteners, flavoring agents, perfumes and the like. A tablet and pill may further be enteric-coated. An oral liquid formulation may, for example, be a pharmaceutically acceptable emulsion, syrup, elixir, suspension, solution and the like, which may contain a pharmaceutically customary inert diluent such as water and if desired, additives. Such an oral liquid formulation can be produced by mixing an active ingredient, inert diluent and other additives if necessary in accordance with a customary method. An oral formulation usually contain about 0.01 to 99% by weight, preferably about 0.1 to 90% by weight, usually about 0.5 to 50% by weight of an inventive active compound, although the amount may vary depending on the dosage form.

The dose in a certain patient is determined considering the age, body weight, general condition, sex, diet, administraiton time, administraiton mode, excretion rate, drug combination, degree of the disease treated currently as well as other factors.

A lipid-rich plaque regressing agent containing a compound of the present invention has a low toxicity and can be used safely, and its daily dose varies depending on the condition and body weight of the patient, the type of the compound and the administration route and, for example, when used as a prophylactic and therapeutic agent against hyperlipidemia, it may be about 1 to 500 mg, preferably about 10 to 200 mg as an active ingredient [I] in an oral formulation, and about 0.1 to 100 mg, preferably about 1 to 50 mg, usually about 1 to 20 mg as an active ingredient [I] in a parenteral formulation for an adult (60 kg), a dose within which exhibited no toxicity.

The present invention also provides:
(1) a pharmaceutical composition comprising a compound of the present invention with a concomitant drug (hereinafter referred to as a concomitant formulation),
(2) a method for regressing a lipid-rich plaque which comprises administering a combination of an effective amount of a compound of the present invention and an effective amount of a concomitant drug to a mammal, and,
(3) a method for preventing and treating acute coronary artery syndrome such as acute myocardial infarction and unstable angina, peripheral artery occlusion, restenosis after percutaneous transluminal coronary angioplasty (PTCA), hypercholesteremia, atherosclerosis, ischemic heart disease such as myocardial infarction, cerebrovascular impairment such as cerebral infarction and apoplexy by administering a combination of an effective amount of a compound of the present invention and an effective amount of a concomitant drug to a mammal.

A concomitant drug which can be used in combination with a compound of the present invention may, for example, be the pharmaceutical components other than the inventive compounds described above and other hyperlipidemia treating agents, diuretics, hypertension treating agents, cardiac failure treating agents, arrhythmia treating agents, anticoagulants, antiplatelet agents, diabetes treating agents, HDL increasing agents, unstable plaque stabilizing agents, vasodilators, vasoconstrictors, hypertensive agents, antibacterial agents, antifungal agents, non-steroidal antiinflammatory agents, steroidal agents, immunoregulating agents, antiprotozoal agents, anti-ulcer agents, bronchospasmolytic expectorants, sedatives, narcotics, anxiolytic agents, antipsychotic agents, muscle relaxants, antiepileptic agents, antidepressants, narcotic antagonists, anti-tumor agents, anti-allergic agents, vitamins, vitamin derivatives, bone-calcium metabolizing agents, osteoporosis treating agents, arthritis treating agents, antirheumatic agents, anti-asthmatic agents, pollakiuria/incontinence treating agents, renal failure/nephrosis treating agents, atopic dermatitis treating agents, allergic rhinitis treating agents, endotoxin antagonists or antibodies, signal transmission inhibitors, inflammatory mediating effect inhibitors, inflammatory mediating effect inhibiting antibodies, anti-inflammatory mediating effect inhibitors, anti-inflammatory mediating effect inhibiting antibodies and the like, with hyperlipidemia treating agents, diuretics, hypertension treating agents, cardiac failure treating agents, arrhythmia treating agents, anticoagulants, antiplatelet agents, diabetes treating agents, HDL increasing agents, unstable plaque stabilizing agents being preferred. Concomitant drugs other than those described above are specifically those listed below.

(1) Hyperlipidemia Treating Agents

HMG-CoA reductase inhibitors (e.g., fluvastatin, cerivastatin, atorvastatin and the like), fibrates (e.g., simfibrate, clofibrate aluminium, clinofibrate, fenofibrate and the like), anion exchange resins (e.g., cholestyramine and the like), nicotinic acid formulations (e.g., nicomol, niceritrol, tocopherol nicotinate and the like), polyvalent unsaturated fatty acid derivatives (e.g., ethyl icosapentate, polyene phosphatidylcholine, melinamide and the like), vegetable sterols (e.g., γ-oryzanol, soysterol and the like), elastases, sodium dextran sulfate, squalene synthetase inhibitor, CETP inhibitor, ethyl 2-chloro-3-[4-(2-methyl-2-phenylpropoxy)phenyl]propionate [Chem. Pharm. Bull., 38, 2792, 2796 (1990)] and the like.

(2) Diuretics

Thiazide diuretics (benzylhydro-chlorothiazide, cyclopenthiazide, ethiazide, hydrochlorothiazide, hydroflumethiazide, methyclothiazide, penfluthiazide, polythiazide, trichloromethiazide and the like), loop diuretics (clortharidone, clofenamide, indapamide, mefruside, meticrane, sotolazone, tripamide, quinethazone, metolazone, furosemide, mefruside and the like), potassium retaining diuretics (spironolacton, triamterene and the like).

(3) Hypertension Treating Agents

[1] Sympathetic Nerve Suppressants $\alpha_2$ stimulants (e.g., clonidine, guanabenz, guanfacine, methyldopa and the like), ganglionic blocking agents (e.g., hexamethonium, trimethaphan and the like), presynaptic blockers (e.g., alseroxylon, dimethylaminoreserpinate, rescinamine, reserpine, syrosingopine and the like), neuron blockers (e.g., betanidine, guanethidine and the like), $\alpha_1$ blockers (e.g., bunazosin, doxazocin, prazosin, terazosin, urapidil and the like), β blockers (e.g., propranolol, nadolol, timolol, nipradilol, bunitrolol, indenolol, penbutolol, carteolol, carvedilol, pindolol, acebutolol, atenolol, bisoprolol, metoprolol, labetalol, amosulalol, arotinolol and the like).

[2] Vasodilators

Calcium channel antagonists (e.g., manidipine, nicardipine, nilvadipine, nisoldipine, nitrendipine, benidipine, amlodipine, aranidipine and the like), phthalazine derivatives (e.g., budralazine, cadralazine, ecarazine, hydralazine, todralazine and the like) and the like.

[3] ACE Inhibitors

Alacepril, captopril, cilazapril, delapril, enalapril, lisinopril, temocapril, trandolapril, quinapril, imidapril, benazepril, perindopril and the like.

[4] AII Antagonists

Losartan, candesartan, valsartan, telimisartan, irbesartan, forasartan and the like.

[5] Diuretics (for Example, Diuretics Described Above)

(4) Cardiac Failure Treating Agents

Cardiotonic agents (e.g., digitoxin, digoxin, methyldigoxin, lanatoside C, proscillaridine and the like), α,β-stimulants (e.g., epinephrine, norepinephrine, isoproterenol, dopamine, docarpamine, dobutamine, denopamine and the like), phosphodiesterase inhibitors (e.g., aminone, milrinone, olprinone hydrochloride and the like), calcium channel sensitivity promoters (e.g., pimobendan and the like), nitrate agents (e.g., nitroglycerin, isosorbide nitrate and the like), ACE inhibitors (for example, ACE inhibitors described above), diuretics (for example, diuretics described above), carperitide, ubidecarenone, vesnarinone, aminophylline and the like.

(5) Arrhythmia Treating Agents

Sodium channel blockers (e.g., quinidine, procainamide, disopyramide, ajimaline, cibenzoline, lidocaine, diphenyl hydantoin, mexiletine, propafenone, flecainide, pilsicainide, phenytoin and the like), β-blockers (e.g., propranolol, alprenolol, bufetolol, oxprenolol, atenolol, acebutolol, metoprolol, bisoprolol, pindolol, carteolol, arotinolol and the like), potassium channel blockers (e.g., amiodarone and the like), calcium channel blockers (e.g., verapamil, diltiazem and the like) and the like.

(6) Anticoagulants and Antiplatelet Agents

Sodium citrate, activated protein C, tissue factor pathway inhibitors, anti-thrombin III, dalteparin sodium, argatroban, gabexate, sodium ozagrel, ethyl icosapentate, beraprost sodium, alprostadil, pentoxifylline, tisokinase, streptokinase and the like.

(7) Diabetes Treating Agents

Sulfonyl ureas (e.g., tolbutamide, chlorpropamide, glyclopyramide, acetohexamid, tolazamide, glibenclamide, glybuzole and the like), biguamides (e.g., metformin hydrochloride, buformin hydrochloride and the like), α-glucosidaseinhibitor (e.g., voglibose, acarbose and the like), insulin sensitizer (e.g., pioglitazone, troglitazone and the like), insulin, glucagon, diabetic complication treating agent (e.g., epalrestat and the like) and the like.

(8) HDL Increasing Agents

Squalene synthetase inhibitors, CETP inhibitors, LPL activators and the like.

(9) Unstable Plaque Stabilizing Agents

MMP inhibitors, kinase inhibitors.

(10) Vasodilators

Oxyphedrine, diltiazem, tolazoline, hexobendine, bamethan, clonidine, methyldopa, guanabenz and the like.

(11) Vasoconstrictors

Dopamine, dobutamine denopamine and the like.

(12) Hypertensive Agents

Dopamine, dobutamine, denopamine, digitoxin, digoxin, methyldigoxin, lanatoside C, G-Strophantin and the like.

(13) Antibacterial Agents

[1] Sufonamides

Sulfamethizole, sulfisoxazole, sulfamonomethoxin, sulfamethizole, salazosulfapyridine, silver sulfadiazine and the like.

[2] Quinolones

Nalidixic acid, pipemidic acid trihydrate, enoxacin, norfloxacin, ofloxacin, tosufloxacin tosilate, ciprofloxacin hydrochloride, lomefloxacin hydrochloride, sparfloxacin, fleroxacin and the like.

[3] Anti-Tuberculous Agents

Isoniazid, ethambutol(ethambutol hydrochloride), p-aminosalicylic acid (calcium p-aminosalicylate), pyrazinamide, ethionamide, prothionamide, rifampicin, streptomycin sulfate, kanamycin sulfate, cycloserine and the like.

[4] Anti Acid-Fast Bacteria Agents

Diaphenylsulfone, rifampicin and the like.

[5] Anti-Viral Agents

Idoxuridine, acyclovir, vidarabine, ganciclovir and the like.

[6] Anti-HIV Agent

Zidovudine, didanosine, zalcitabine, indinavir sulfate ethanol adduct, ritonavir and the like.

[7] Anti-Spirochete Agents

[8] Antibiotics

Tetracyclin hydrochloride, ampicillin, piperacillin, gentamycin, dibekacin, kanendomycin, lividomycin, tobramycin, amikacin, fradiomycin, sisomicin, tetracyclin, oxytetracyclin, rolitetracyclin, doxycyclin, ampicillin, piperacillin, ticarcillin, cefalotin, cefapirin, cefaloridine, cefaclor, cefalexin, cefroxadine, cefadroxil, cefamandole, cefotoam, cefroxime, cefotiam, cefotiam hexetil, cefuroxime axetil, cefdinir, cefditoren pivoxil, ceftazidime, cefpiramide, cefsulodin, cefinenoxime, cefpodoxime proxetil, cefpirome, cefozopran, cefepime, cefsulodin, cefinenoxime, cefinetazole, cefminox, cefoxitin, cefbuperazone, latamoxef, flomoxef, cefazolin, cefotaxime, cefoperazon, ceftizoxime, moxalactam, thienamycin, sulfazecin, azthreonam and their salts, griseofulvin, lankacidin [J. Antibiotics, 38, 877–885 (1985)] and the like.

(14) Antifungal Agents

[1] Polyene-based antibiotics (e.g., amphotericin B, nystatin, trichomycin).

[2] Griseofulvin, pyrrolnitrin and the like.

[3] Cytosine metabilism antagonists (e.g., flucytosine).

[4] Imidazole derivatives (e.g., econazole, clotrimazole, miconazole nitrate, bifonazole, croconazole).

[5] Triazole derivatives (e.g., fluconazole, itraconazole, azole-based compound [2-[(1R, 2R)-2-(2,4-difluorophenyl)-2-hydroxy-1-methyl-3-(1H-1,2,4-triazol-1-yl)propyl]-4-[4-(2,2,3,3-tetrafluoropropoxy)phenyl-3-(2H,4H)-1,2,4-triazolone).

[6] Thiocarbamic acid derivatives (e.g., trinaphthol).

[7] Echinocandin-based derivatives (e.g., caspofamgine, FK-463, V-Echinocadin) and the like.

(15) Non-steroidal antiinflammatory agents

Acetaminophen, fenasetin, ethenzamide, sulpyrine, antipyrine, migrenin, aspirin, mefenamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, epirizol, tiaramide hydrochloride, zaltoprofen, gabexate mesilate, camostat mesilate, ulinastatin, colchicine, probenecid, sulfinpyrazone, benzbromarone, allopurinol, sodium gold thiomalate, sodium hyaluronate, sodium salicylate, morphine hydrochloride, salicylic acid, atropine, scopolamine, morphine, pethidine, levorphanol, ketoprofen, naproxen, oxymorphone and their salts.

(16) Steroidal Agents

Dexamethasone, hexestrol, methimazole, betamethasone, triamcinolone, triamcinolone acetonide, fluorocinonide, fluorocinolone acetonide, prednisolone, methylprednisolone, cortisone acetate, hydrocortisone, fluorometholone, beclometasone dipropionate, estriol and the like.

(17) Immunoregulating Agents

Cyclosporin, tacrolimus, gusperimus, azathioprine, anti-lymph serum, dried sulfonated immunogloburin, erythropoietin, colony stimulating factor, interleukin, interferon and the like.

(18) Antiprotozoal Agents

Metronidazole, timidazole, diethylcarbamadine citrate, quinine hydrochloride, quinine sulfate and the like.

(19) Anti-ulcer Agents

Metoclopramide, histidine hydrochloride, lansoprazole, metoclopramide, pirenzepine, cimetidine, ranitidine, famotidine, urogastrine, oxethazaine, proglumide, omeprazole, sucralfate, sulpiride, cetraxate, gefarnate, aldioxa, teprenone, prostaglandin and the like.

(20) Bronchospasmolytic Expectorants

Ephedrine hydrochloride, noscapine hydrochloride, codeine phosphate, dihydrocodeine phosphate, isoproterenol hydrochloride, ephedrine hydrochloride, methylephedrine hydrochloride, noscapine hydrochloride, aroclamide, chlorfesianol, picoperidamine, cloperastine, protokylol, isoproterenol, sulbutamol, terbutaline, oxymetebanol, morphine hydrochloride, dextromethorphan hydrobromide, oxycodone hydrochloride, dimemorfan phosphate, tipepidine hibenzate, pentoxyverine citrate, clofedanol hydrochloride, benzonatate, guaifenesin, bromhexine hydrochloride, ambroxol hydrochloride, acetylcysteine, ethylcysteine hydrochloride, carbocysteine and the like.

(21) Sedatives

Chlorpromazine hydrochloride, atropine sulfate, phenobarbital, barbital, amobarbital, pentobarbital, thiopental sodium, thiamylal sodium, nitrazepam, estazolam, flunitrazepam, haloxazolam, triazolam, flunitrazepam, bromovalerylurea, chloral hydrate, triclofos sodium and the like.

(22) Anesthetics (22-1) Local Anesthetics

Cocaine hydrochloride, procaine hydrochlodie, lidocaine, dibucaine hydrochloride, tetracaine hydrochloride, mepivacaine hydrochloride, bupivacaine hydrochloride, oxybuprocaine hydrochloride, ethyl aminobenzoate, oxethazaine and the like.

(22-2) Systemic Anesthetics

[1] Inhalation anesthetics (e.g., ether, halothane, nitrous oxide, enflurane, enflurane),

[2] Intravenous anesthetics (e.g., ketamine, droperidol, thiopental sodium, thiamylal sodium, pentobarbital) and the like.

(23) Anxiolytic Agents

Diazepam, lorazepam, oxazepam, chlordiazepoxide, medazepam, oxazolam, cloxazolam, clotiazepam, prazepam, etizolam, fludiazepam, hydroxyzine and the like.

(24) Antipsychotic Agents

Chlorpromazine hydrochloride, prochloroperazine, trifluoperazine, thioridazine hydrochloride, perphenazine hydrochloride, perphenazine maleate, fluphenazine enanthate, prochloperazine maleate, levomepromazine maleate, promethazine hydrochloride, haloperidol, bromperidol, spiperone, reserpine, clomipramine hydrochloride, sulpiride, zotepine and the like.

(25) Muscle Relaxants

Pridinol, tubocurarine, pancuronium, tolperisone hydrochloride, chlorphenesin carbamate, baclofen, chlormezanone, mephenesin, chlozoxazone, eperisone, tizanidine and the like.

(26) Antiepileptic Agents

Phenytoin, ethosuximide, acetazolamide, chlordiazepoxide, trimethadione, carbamazepine, phenobarbital, primidone, sulthiam, sodium valproate, clonazepam, diazepam, nitrazepam and the like.

(27) Antidepressants

Imipramine, clomipramine, noxiptiline, pheneridine, amitriptyline hydrochloride, nortriptyline hydrochloride, amoxapine, mianserin hydrochloride, maprotiline hydrochloride, sulpiride, fluvoxamine maleate, trazodone hydrochloride and the like.

(28) Anesthetic Antagonists

Levallorphan, nalorphine, naloxone and their salts and the like.

(29) Antitumor Agents

6-O-(N-Chloroacetylcarbamoyl), fumagilol, bleomycin, methotrexate, actinomycin D, mitomycin C, daunorubicin, adriamycin, neocarcinostatin, cytosine arabinoside, fluorouracil, tetrahydrofuryl-5-fluorouracil, picibanil, lentinan, levamisole, bestatin, azimexon, glycyrrhizin, doxorubicin hydrochloride, aclarubicin hydrochloride, bleomycin hydrochloride, peplomycin sulfate, vincristine sulfate, vinblastine sulfate, irinotecan hydrochloride, cyclophosphamide, melphalan, zisulphan, thiotepa, procarbazine hydrochloride, cisplatin, azathioprine, mercaptoprine, tegafur, carmofur, cytarabine, methyltestosterone, testosterone propionate, testosterone enanthate, mepitiostane, fosfestrol, chlormadinone acetate, leuproline acetate, buserelin acetate and the lile.

(30) Anti-allergic Agents

Diphenhydramine, chlorphenyramine, tripelennamine, methodiramine, clemizole, diphenylpyraline, methoxyphenamine, sodium cromoglicate, tranilast, repirinast, amlexanox, ibudilast, ketotifen, terfenadine, mequitazine, azelastine, epinastine, ozagrel hydrochloride, pranlukast hydrate, seratrodast and the like.

(31) Lipid-soluble Vitamins

[1] Vitamin As: Vitamin $A_1$, Vitamin $A_2$ and retinol palmitate.

[2] Vitamin Ds: Vitamin $D_1$, $D_2$, $D_3$, $D_4$ and $D_5$.

[3] Vitamin Es: α-tocopherol, β-tocopherol, γ-tocopherol, δ-tocopherol, dl-α-tocopherol nicotinate.

[4] Vitamin Ks: Vitamin $K_1$, $K_2$, $K_3$ and $K_4$.

[5] Folic acid (vitamin M) and the like.

(32) Vitamin Derivatives

Various vitamin derivatives such as vitamine $D_3$ derivarives including 5,6-trans-cholecalciferol, 2,5-hydroxycholecalciferol, 1-α-hydroxycholecalciferol and the like, vitamin $D_2$ derivatives including 5,6-trans-ergocalciferol and the like.

(33) Anti-asthmatic Agents

Isoprenaline hydrochloride, salbutamol sulfate, procaterol hydrochloride, terbutaline sulfate, trimetoquinol hydrochloride, tubobuterol hydrochloride, orciprenaline sulfate, fenoterol hydrobromide, ephedrine hydrochloride, ipratropium bromide, oxitropium bromide, flutropium bromide, theophylline, aminophylline, sodium cromoglicate, tranilast, repirinast, amlexanox, ibudilast, ketotifen, terfenadine, mequitazine, pranlukast hydrate, seratrodast, dexamethasone, prednisolone, hydrocortisone, beclometaason dipropionate and the like,

(34) Pollakiuria/incontinence Treating Agents

Flavoxate hydrochloride and the like.

(35) Atopic Dermatitis Treating Agents

Sodium cromoglicate and the like.

(36) Allergic Rhinitis Treating Agents

Sodium cromoglicate, chlorphenyramine maleate, alimemazine tartrate, clemastine fumarate, homochlorcyclizine hydrochloride, terfenadine, mequitazine and the like.

(37) Others

Hydroxycam, diaserine, megestrol acetate, nicergoline, plostaglandins and the like.

By means of a combination of a compound of the present invention with a concomitant drug, for example, the following effects are experienced.

(1) The dose or the side effect of a compound of the present invention or a salt thereof or a prodrug thereof and a concomitant drug can be lower than those when given alone.

(2) A synergistic therapeutic effect can be obtained against acute coronary artery syndrome such as acute myocardial infarction and unstable angina, peripheral artery occlusion, restenosis after percutaneous transluminal coronary angioplasty (PTCA), hypercholesteremia, atherosclerosis, ischemic heart disease such as myocardial infarction and angina pectoris, cerebrovascular impairment such as cerebral infarction and apoplexy as well as thrombus formation.

(3) A wide therapeutic effect can be obtained against various diseases accompanied with diseases developed in association with acute coronary artery syndrome such as acute myocardial infarction and unstable angina, peripheral artery occlusion, restenosis after percutaneous transluminal coronary angioplasty (PTCA), hypercholesteremia, atherosclerosis, ischemic heart disease such as myocardial infarction and angina pectoris, cerebrovascular impairment such as cerebral infarction and apoplexy as well as thrombus formation.

When using a compound of the present invention in combination with a concomitant drug, the timings of the administrations of the compound of the present invention and the concomitant drug are not particularly limited, and the compound of the present invention or its pharmaceutical composition and the concomitant drug or its pharmaceutical composition can be given to a subject simultaneously or at a certain time interval. The dose of a concomitant drug may be in accordance with a dose employed clinically, and selected appropriately depending on the target, route, disease, combination and the like.

The administration mode of the concomitant formulation of the present invention is not particularly limited, provided that the compound of the present invention and the concomitant drug are combined upon administration. Such an administration mode may, for example, be (1) an administration of a single formulation obtained by formulating a compound of the present invention and a concomitant drug simultaneously, (2) a simultaneous administration via an identical route of two formulations obtained by formulating a compound of the present invention and a concomitant drug separately, (3) a sequential and intermittent administration via an identical route of two formulations obtained by formulating a compound of the present invention and a concomitant drug separately, (4) a simultaneous administration via different routes of two formulations obtained by formulating a compound of the present invention and a concomitant drug separately, (5) a sequential and intermittent administration via different routes of two formulations obtained by formulating a compound of the present invention and a concomitant drug separately (for example, inventive compound or its pharmaceutical composition followed by concomitant drug or its pharmaceutical composition, or inverse order) and the like.

A concomitant formulation of the present invention has a low toxicity, and thus a compound of the present invention and/or a concomitant drug described above are mixed with a pharmacologically acceptable carrier in accordance with a method known per se to form a pharmaceutical composition, for example, a tablet (including sugar-coated and film-coated tablets), powder, granule, capsule (including soft capsule), solution, injection formulation, suppository, sustained release formulation and the like, which can safely be given orally or parenterally (e.g., topically, rectally, intravenously). An injection formulation may be given intravenously, intramuscularly, subcutaneously, into an organ, or directly into a lesion.

A pharmacologically acceptable carrier which may be employed for producing a concomitant formulation of the present invention may, for example, be various organic and inorganic carrier materials employed customarily as pharmaceutical materials such as excipients, lubricants, binders and disintegrants in a solid formulation, solvents, dissolution aids, suspending agents, isotonicity imparting agents, bufferring agents and analgesic agents in a liquid formulation. Furthermore, other additives such as ordinary preservatives, antioxidants, colorants, sweeteners, adsorbents, wetting agents may also be added in suitable amounts.

An excipient may, for example, be lactose, sugar, D-mannitol, starch, corn starch, crystalline cellulose, light silicate anhydride and the like.

A lubricant may, for example, be magnesium stearate, calcium stearate, talc, colloidal silica and the like.

A binder may, for example, be crystalline cellulose, sugar, D-mannitol, dextrin, hydroxypropyl cellulose, hydroxypropylmethyl cellulose, polyvinyl pyrrolidone, starch, sucrose, gelatin, methyl cellulose, sodium carboxymethyl cellulose and the like.

A disintegrant may, for example, be starch, carboxymethyl cellulose, calcium carboxymethyl cellulose, sodium carboxymethyl starch, L-hydroxypropyl cellulose and the like.

A solvent may, for example, be water for injection, alcohol, propylene glycol, macrogol, sesame oil, corn oil, olive oil and the like.

A dissolution aid may, for example, be polyethylene glycol, propylene glycol, D-mannitol, benzyl benzoate, ethanol, trisaminomethane, cholesterol, triethanolamine, sodium carbonate, sodium citrate and the like.

A suspending agent may, for example, be a surfactant such as stearyl triethanolamine, sodium lauryl sulfate, laurylaminopropionic acid, lecithin, benzalkonium chloride, benzethonium chloride, glycerin monostearate and the like; hydrophilic polymer such as polyvinyl alcohol, polyvinyl pyrrolidone, sodium carboxymethyl cellulose, methyl cellulose, hydroxymethyl cellulose, hydroxyethyl cellulose, hydroxypropyl cellulose and the like.

An isotonicity imparting agent may, for example, be glucose, D-sorbitol, sodium chloride, glycerin, D-mannitol and the like.

A buffering agent may, for example, be a buffer solution of a phosphate, acetate, carbonate, citrate and the like.

An analgesic may, for example, be benzyl alcohol.

A preservative may, for example, be a p-oxybenzoate, chlorobutanol, benzyl alcohol, phenethyl alcohol, dehydroacetic acid, sorbic acid and the like.

An antioxidant may, for example, be a sulfite, ascorbic acid, α-tocopherol and the like.

The ratio between a compound of the present invention and a concomitant drug in a concomitant formulation of the present invention may be selected appropriately on the basis of the target, route and disease.

For example, the amount of a compound of the present invention contained in a concomitant formulation of the present invention is usually about 0.01 to 100% by weight, preferably about 0.1 to about 50% by weight, more preferably about 0.5 to about 20% by weight based on the entire formulation, although it may vary depending on the dosage form.

The amount of an concomitant drug contained in a concomitant formulation of the present invention is usually about 0.01 to 100% by weight, preferably about 0.1 to about 50% by weight, more preferably about 0.5 to about 20% by weight based on the entire formulation, although it may vary depending on the dosage form.

The amount of an additive such as a carrier contained in a concomitant formulation of the present inventionis usually about 1 to about 99.99% by weight, preferably about 10 to about 90% by weight based on the entire formulation, although it may vary depending on the dosage form.

Similar amounts may be employed also when a compound of the present invention and a concomitant drug are formulated separately.

Such a formulation can be produced by a method known per se which is employed usually in a pharmaceutical process.

For example, a compound of the present invention and a concomitant drug can be formulated with a dispersant (e.g., Tween 80 (ATLAS POWDER, USA), HCO60 (NIKKO CHEMICALS), polyethylene glycol, carboxymethyl cellulose, sodium alginate, hydroxypropylmethyl cellulose, dextrin), a stabilizer (e.g., ascorbic acid, sodium pyrosulfite), a surfactant (e.g., polysorbate 80, macrogol), a solubilizing agent (e.g., glycerin, ethanol), a buffering agent (phosphoric acid and its alkali metal salt, citric acid and its alkali metal salt and the like), an isotonizing agent (e.g., sodium chloride, potassium chloride, mannitol, sorbitol, glucose), a pH modifier (e.g., hydrochloric acid, sodium hydroxide), a preservative (e.g., ethyl p-oxybenzoate, benzoic acid, methylparabene, propylparabene, benzyl alcohol), a solubilizer (e.g., concentrated glycerin, meglumine), a solubilizing aid (e.g., propylene glycol, sugar), an analgesic (e.g., glucose, benzyl alcohol) into an aqueous formulation for injection, or dissolved, suspended or emulsified in a vegetable oil such as olive oil, sesame oil, cottonseed oil and corn oil and in a solubilizing aid such as propylene glycol to form an oily formulation, whereby producing an injection formulation.

In order to obtain an oral dosage form, a method known per se is employed to compact an inventive compound or a concomitant drug for example with an excipient (e.g., lactose, sugar, starch), a disintegrant (e.g., starch, calcium carbonate), a binder (e.g., starch, gum Arabic, carboxymethyl cellulose, polyvinyl pyrrolidone, hydroxypropyl cellulose) or a glidant (e.g., talc, magnesium stearate, polyethylene glycol 6000) into a desired shape, which is then, if necessary, coated for the purpose of a taste masking, an enteric property or a sustained release performance by means of a coating method known per se, whereby obtaining an oral dosage form. Such a coating may, for example, be hydroxypropylmethyl cellulose, ethyl cellulose, hydroxymethyl cellulose, hydroxypropyl cellulose, polyoxyehtylene glycol, Tween 80, Pluronic F68, cellulose acetate phthalate, hydroxypropylmethyl cellulose phthalate, hydroxymethyl cellulose acetate succinate, Eudragit (Rohm, German, methacrylic/acrylic acid copolymer) and a colorant (e.g., iron oxide red, titanium dioxide). An oral dosage form may be an instantaneous release formulation or a sustained release formulation.

For example, in order to obtain a suppository, a method known per se is employed to convert an inventive compound or concomitant drug into an oily or aqueous solid, semi-solid or liquid suppository. An oily base employed in a composition described above may, for example, be a higher fatty acid glyceride [e.g., cocoa butter, UITEPSOL (DYNAMITE NOVEL, Germany)], a medium fatty acid [e.g., MIGRIOL (DYNAMITE NOVEL, Germany)], or a vegetable oil (e.g., sesame oil, soybean oil, cottonseed oil). An aqueous base may, for example, be polyethylene glycol and propylene glycol, and an aqueous gel base may, for example, be natural gums, cellulose derivatives, vinyl polymers and acrylic acid polymers.

A sustained release formulation described above may, for example, be a sustained-release microcapsule.

While a sustained-release microcapsule can be obtained by a method known per se, a sustained release formulation shown in Section [2] described below is formed and administered in a preferred case.

An compound of the present invention is preferably formulated as an oral dosage form such as a solid formulation (e.g., powder, granule, tablet, capsule), or as a rectal formulation such as a suppository. An oral dosage form is particularly preferred.

A concomitant drug can be formulated into a dosage form described above based on the type of the drug.

The followings are the descriptions with regard to [1] an injection formulation of a compound of the present invention or a concomitant drug and a method for producing the same, [2] a sustained-release or immediate release formulation of a drug of a compound of the present invention or a concomitant drug and a method for producing the same, [3] a sublingual, buccal or oral instantaneous disintegration formulations employing of a compound of the present invention or a concomitant drug and a method for producing the same, and [4] a solid dispersion of a compound of the present invention or a concomitant drug and a method for producing the same.

[1] Injection Formulation and Method for Producing the Same

A solution obtained by dissolving a compound of the present invention or a concomitant drug in water is employed preferably. Such injection formulation may contain a benzoate and/or a salicylate.

Said injection formulation is obtained by dissolving a compound of the present invention or a concomitant drug in water together with a benzoate and/or a salicylate in water as desired.

A benzoate and/or a salicylate described above may be an alkali metal salt such as sodium and potassium salts, an alkaline earth metal salt such as calcium and magnesium salts, an ammonium salt, a meglumine salt as well as a salt of an organic acid such as trometamol.

The concentration of a compound of the present invention or a concomitant drug in a injection formulation is 0.5 to 50 w/v %, preferably about 3 to 20 w/v %. The concentration of a benzoate and/or a salicylate is 0.5 to 50 w/v %, preferably 3 to 20 w/v %.

The formulation may contain additives employed customarily in a injection formulation, such as a stabilizer (ascorbic acid, sodium pyrosulfite and the like), a surfactant (polysorbate 80, macrogol and the like), a solubilizing agent (glycerin, ethanol and the like), a buffering agent (phosphoric acid and its alkali metal salt, citric acid and its alkali metal salt and the like), an isotonizing agent (sodium chloride, potassium chloride and the like), a dispersing agent (hydroxypropylmethyl cellulose, dextrin), a pH modifier (hydrochloric acid, sodium hydroxide and the like), a preservative (ethyl p-oxybenzoate, benzoic acid and the like), a solubilizer (concentrated glycerin, meglumine and the like), a solubilizing aid (propylene glycol, sugar and the like), a painkiller (glucose, benzyl alcohol and the like) as appropriate. Any of these additives is added in an amount employed customarily in a formulation for injection.

The pH of an injection formulation is adjusted at 2 to 12, preferably 2.5 to 8.0 with a pH modifier.

An injection formulation is obtained by dissolving a compound of the present invention or a concomitant drug if desired together with a benzoate and/or salicylate in water if desired together with the additives listed above. These components may be dissolved in any order as appropriate similarly to a customary preparation of a formulation for injection.

An aqueous solution for injection is preferably warmed, and given as a formulation for injection after sterilizing by filtration or autoclave similarly to a customary formulation for injection.

An aqueous solution for injection is preferably autoclaved at 100 to 121° C. for 5 to 30 minutes.

A formulation may be present as a solution imparted with an antibacterial activity for the purpose of using several times in divided doses.

[2] Sustained-release or Immediate Release Formulation and Method for Producing the Same A sustained release formulation obtained by coating a core containing a compound of the present inventiond or a concomitant drug with a coating agent such as a water-insoluble material or a swelling polymer as desired is employed preferably. For example, a sustained-release oral formulation of a single daily dose is preferred.

A water-insoluble material employed as a coating agent may, for example, be cellulose ethers such as ethyl cellulose and butyl cellulose, cellulose esters such as cellulose acetate and cellulose propionate, polyvinyl esters such as polyvinyl acetate and polyvinyl butyrate, acrylic acid-based polymers such as an acrylic acid/methacrylic acid copolymer, a methyl methacrylate copolymer, an ethoxyethyl methacrylate/cinnamoethyl methacrylate/aminoalkyl methacrylate copolymer, polyacrylic acid, polymethacrylic acid, a metacrylic acid alkylamide copolymer, a poly(methyl methacrylate), a polymethacrylate, a polymethacrylamide, an aminoalkyl methacrylate copolymer, a poly(methacrylic anhydride), a glycidyl methacrylate copolymer, especially, a series of Eudragit (Rohm Pharma) such as Eudragit RS-100, RL-100, RS-30D, RL-30D, RL-PO, RS—PO (ethyl acrylate/methyl methacrylate/chlorotrimethyl methacrylate/ethyl ammonium copolymer) and Eudragit NE-30D (methyl methacrylate/ethyl acrylate copolymer), hydrogenated oils such as a hydrogenated castor oil (e.g., Lubri wax (FREUND), waxes such as carnauba wax, a fatty acid glycerin ester and paraffin and a polyglycerin fatty acid ester.

As a swelling polymer, a polymer having an acidic leaving group and exhibiting a pH-dependent swelling is preferred, and an acidic leaving group-bearing polymer which undergoes a less swelling at an acidic pH such as in stomach but is swollen extensively at a neutral pH such as in small and large intestines is preferred.

Such polymer having an acidic leaving group and exhibiting a pH-dependent swelling may, for example, be a crosslinked polyacrylic acid polymer such as Carbomers 934P, 940, 941, 974P, 980, 1342 and the like, Polycarbophil and Carcium Polycarbophil (BF Goodrioch), HIBIS Wakos 103, 104, 105 and 304 (Wako Pure Chemical).

A coating agent employed in a sustained release formulation may further contain a hydrophilic material.

Such hydrophilic material may, for example, be a polysaccharide which may have a sulfate group such as pullulan, dextrin and alkali metal alginates, a polysaccharide having a hydroxyalkyl group or a carboxyalkyl group such as hydroxypropyl cellulose, hydroxypropylmethyl cellulose and sodium carboxymethyl cellulose as well as methyl cellulose, polyvinyl pyrrolidone, polyvinyl alcohol and polyethylene glycol.

The water-insoluble material content in a coating agent of a sustained release formulation is about 30 to about 90% (w/w), preferably about 35 to about 80% (w/w), more preferably about 40 to about 75% (w/w), and the swelling polymer content is about 3 to about 30% (w/w), preferably about 3 to about 15% (w/w). A coating agent may further contain a hydrophilic material, the content of which in the coating is about 50% (w/w) or less, preferably about 5 to about 40% (w/w), more preferably about 5 to about 35% (w/w). A % (w/w) referred here means a % by weight based on the coating composition which is the remainder of the coating solution after deleting any solvent (e.g., water and a lower alcohol such as methanol and ethanol).

A sustained release formulation is produced, as exemplified below, by preparing a core containing a drug followed by coating a resultant core with a coating solution obtained by melting a water-insoluble material or a swelling polymer or by dissolving or dispersing such material in a solvent.

I. Drug-containing Core Preparation

While a coated drug-containing core (hereinafter sometimes referred to simply as a core) may be in any non-limiting shape, it is formed preferably as a particle such as a granule or a fine particle.

When a core is a granule or a fine particle, it has a mean particle size preferable of about 150 to 2,000 µm, more preferably about 500 to 1,400 µm.

A core can be prepared by a standard method. For example, a drug is combined with suitable excipient, binder, disintegrant, glidant, stabilizer and the like, and then subjected to a wet extrusion granulation or a fluidized bed granulation.

The drug content in a core is about 0.5 to about 95% (w/w), preferably about 5.0 to about 80% (w/w), more preferably about 30 to about 70% (w/w).

An excipient contained in a core may, for example, be a saccharide such as sucrose, lactose, mannitol and glucose, starch, crystalline cellulose, calcium phosphate and corn starch. Among these, crystalline cellulose and corn starch are preferred.

A binder may, for example, be polyvinyl alcohol, hydroxypropyl cellulose, polyethylene glycol, polyvinyl pyrrolidone, Pluronic F68, gum Arabic, gelatin and starch. A disintegrant -may, for example, be calcium carboxymethyl cellulose (ECG505), sodium croscarmellose (Ac-Di-Sol), crosslinked polyvinyl pyrrolidone (crospovidone) and a low-substituted hydroxypropyl cellulose (L-HPC). Among these, hydroxypropyl cellulose, polyvinyl pyrrolidone and a low-substituted hydroxypropyl cellulose are preferred. A glidant and an anticoagulant may, for example, be talc, magnesium stearate and its inorganic salts, and a lubricant may, for example, be polyethylene glycol. A stabilizer may, for example, be an acid such as tartaric acid, citric acid, succinic acid, fumaric acid and maleic acid.

In addition to the methods described above, other methods can be employed to form a core, such as an agitating granulation method wherein an inert carrier particle as a seed for the core is sprayed with a binder dissolved in a suitable solvent such as water and a lower alcohol (e.g., methanol and ethanol) with being supplemented portionwise with a drug or a mixture thereof with an excipient and a glidant as well as a pan coating method, a fluidized bed coating method and a melting granulation method. An inert carrier particle -may, for example, be one prepared from sugar, lactose, starch, crystalline cellulose and waxes, and has a mean particle size preferably of about 100 µm to about 1,500 µm.

In order to separate a drug contained in a core from a coating, the surface of the core may be covered with a protective material. Such protective material may, for example, be a hydrophilic material described above and a water-insoluble material. A preferred protective material is polyethylene glycol or a polysaccharide having a hydroxyalkyl group or a carboxyalkyl group, more preferably, hydroxypropylmethyl cellulose and hydroxypropyl cellulose. The protective material may contain, as a stabilizer, an acid such as tartaric acid, citric acid, succinic acid, fumaric acid and maleic acid, as well as a glidant such as talc. A protective material, when employed, is coated at a rate of about 1 to about 15% (w/w), preferably about 1 to about 10% (w/w), more preferably about 2 to about 8% (w/w) based on a core.

A protective material can be coated by a standard coating method, and specifically a core is spray-coated with the protective material by a fluidized bed coating method and a pan coating method.

II. Coating of Core with Coating Agent

A core obtained as described above in Section I is coated with a coating solution containing a water-insoluble material, a pH-dependent swelling polymer and a hydrophilic material being melted therein by heating or being dissolved or dispersed in a solvent to obtain a sustained release formulation.

A method for coating a core with a coating solution may, for example, be a spray coating.

The ratio between a water-insoluble material, a swelling polymer and a hydrophilic material in a coating solution may be selected appropriately in such a manner that respective contents in the coating become those specified above.

The rate of coating agent is about 1 to about 90% (w/w), preferably about 5 to about 50% (w/w), more preferably about 5 to about 35% (w/w) based on the core (excluding the protective material coating).

A solvent for a coating solution is water or an organic solvent, which may be employed alone or in combination with each other. The ratio between water and the organic solvent when being employed in combination (water/organic solvent: weight ratio) may vary from 1 to 100%, and is preferably 1 to about 30%. While said organic solvent is not limited particularly as long as it can dissolve a water-insoluble material, it may, for example, be a lower alcohol such as methyl alcohol, ethyl alcohol, isopropyl alcohol and n-butyl alcohol, a lower alkanone such as acetone, as well as acetonitrile, chloroform, ethylene chloride and the like. Among those listed above, a lower alcohol is preferred, with ethyl alcohol and isopropyl alcohol being especially preferred. Water and a mixture of water and an organic solvent are employed preferably as solvents for a coating. In such a case, an acid such as tartaric acid, citric acid, succinic acid, fumaric acid and maleic acid may be added to the coating solution for the purpose of stabilizing the coating solution.

When the coating is effected by a spray coating, a standard coating method can be employed, and specifically a core is sprayed with a coating by a fluidized bed coating method and a pan coating method. During this process, a lubricant such as talc, titanium oxide, magnesium stearate, calcium stearate and light silicic anhydride and a plasticizer such as glycerin fatty ester, hardened castor oil, triethyl citrate, cetyl alcohol and stearyl alcohol may also be added.

After coating with a coating agent, an antistatic agent such as a talc may also be incorporated if necessary.

An instantaneous release formulation may be a liquid (solution, suspension, emulsion) or a solid (particle, pill, tablet). While an oral formulation and a parenteral formulation such as an injection formulation may be employed, an oral formulation is preferred.

An instantaneous release formulation may usually contain, a carrier, additive and excipient (hereinafter sometimes abbreviated as excipient) which are employed customarily in the pharmaceutical field, in addition to a drug which is an active ingredient. Such a formulation excipient is not limited particularly as long as it is an excipient employed usually as a formulation excipient. For example, an excipient for an oral solid formulation may be lactose, starch, corn starch, crystalline cellulose (Asahi Kasei, Avicel PH101 and the like), powder sugar, granulated sugar, mannitol, light silicic anhydride, magnesium carbonate, calcium carbonate, L-cysteine and the like, with corn starch and mannitol being preferred. Any of these excipients may be employed alone or in combination with each other. The amount of an excipient may, for example, be about 4.5 to about 99.4 w/w %, preferably about 20 to about 98.5 w/w %, more preferably about 30 to about 97 w/w %, based on the entire amount of an instantaneous release formulation.

The drug content in an instantaneous release formulation may be selected within the range from about 0.5 to about 95%, preferably about 1 to about 60%, based on the entire amount of an instantaneous release formulation.

An oral solid instantaneous release formulation contains a disintegrant in addition to the ingredients described above. Such a disintegrant may, for example, be calcium carboxymethyl cellulose (GOTOKUYAKUHIN, ECG505), sodium croscarmellose (for example, Asahi Kasei, Ac-Di-Sol), crospovidone (for example, BASF, Coridon CL), low-substituted hydroxypropyl cellulose (Shin-Etsu Chemical K.K.), carboxymethyl starch (Matsutani Chemical Industry K.K.), sodium carboxymethyl starch (Kimura Industy K.K., EXORITAB), partial α starch (Asahi Kasei, PCS) and the like, any of which may, for example, be brought into contact with water to effect water absorption or swelling, or to make a channel between a core-forming active ingredient and an excipient, whereby disintegrating a granule. Any of these disintegrants may be employed alone or in combination with each other. While the amount of a disintegrant to be incorporated may be selected appropriately based on the type and the amount of the drug employed, it may, for example, be about 0.05 to about 30 w/w %, preferably about 0.5 to about 15 w/w % based on the entire amount of an instantaneous release formulation.

An oral solid instantaneous release formulation contains additives employed customarily in a solid formulation if desired in addition to the components described above. Such additives may, for example, be binders (for example, sucrose, gelatin, powdery gum Arabic, methyl cellulose, hydroxypropyl cellulose, hydroxypropylmethyl cellulose, carboxymethyl cellulose, polyvinylpyrrolidone, pulluran, dextrin), lubricants (for example, polyethylene glycol, magnesium stearate, talc, light silicic anhydride (for example, aerosil (NIPPON AEROSIL)), surfactants (for example, anionic surfactants such as sodium alkylsulfate, nonionic surfactants such as polyoxyethylene fatty ester and polyoxyethylene sorbitan fatty ester, polyoxyethylene castor oil derivatives), colorants (for example, tar-based colorants, caramel, red ocher, titanium oxide, ribofravin), if necessary together with seasonings (for example, sweetener and flavor), adsorbents, preservatives, wetting agents, antistatic agents and the like. As a stabilizer, an organic acid such as tartaric acid, citric acid, succinic acid and fumaric acid may also be added.

A binder described above are preferably hydroxypropyl cellulose, polyethylene glycol and polyvinylpyrrolidone.

An instantaneous formulation can be prepared based on an ordinary formulation technology by mixing the components described above and kneading if necessary and then molding. Such a mixing may be accomplished by an ordinary method, such as mixing and kneading. Typically, when an instantaneous release formulation is formed as a particle, then a method similar to that for preparing a core of a sustained release formulation described above is employed to mix the materials using a vertical granulator, multi-purpose kneader (HATAKE TEKKOSHO), fluidized bed granulator FD-5S (Powrex) and the like, after which a granulation is effected using a wet extrusion granulation or a fluidized bed granulation.

Each of an instantaneous release formulation and a sustained release formulation thus obtained may be formulated separately by a standard method as it is or in combination with an excipient as appropriate and then provided as a final formulation for simultaneous administration or intermittent sequential administration, or the both may be formulated in a single oral formulation (e.g., granule, fine powder, tablet, capsule) as they are or in combination with an excipient as appropriate. The both formulation may be formulated also as granules or fine powders, which are then filled in a single capsule for oral administration.

[3] Sublingual, Buccal or Intraoral Instantaneous Disintegration Formulations and Method for Producing the Same Any of sublingual, buccal or intraoral instantaneous disintegration formulations may be a solid formulation such as a tablet, or may be an oral mucosa plaster (film).

Each of sublingual, buccal or intraoral instantaneous disintegration formulations is preferably a formulation containing an inventive compound or a concomitant drug together with an excipient. An auxiliary agent may also be contained such as a lubricant, iotonizing agent, hydrophilic carrier, water-dispersible polymer and stabilizer. For the purpose of promoting the absorption and enhancing the bioavailability, β-cyclodextrin or β-cyclodextrin derivatives (e.g., hydroxypropyl-β-cyclodextrin) may also be contained.

Such an excipient -may, for example, be lactose, sugar, D-mannitol, starch, crystalline cellulose, light silicic anhydride and the like. A lubricant may, for example, be magnesium stearate, calcium stearate, talc, colloidal silica and the like, with magnesium stearate and colloidal silica being preferred. An iotonizing agent may, for example, be sodium chloride, glucose, fructose, mannitol, sorbitol, lactose, saccharose, glycerin and urea, with mannitol being preferred especially. A hydrophilic carrier may, for example, be a swelling hydrophilic carrier such as a crystalline cellulose, ethyl cellulose, crosslinked polyvinyl pyrrolidone, light silicic anhydride, silicic acid, dicalcium phosphate, calcium carbonate and the like, with a crystalline cellulose (e.g., microcrystalline cellulose) being preferred. A water-dispersible polymer -may, for example, be a gum (e.g., tragacanth gum, acacia gum, guar gum), alginate (e.g., sodium alginate), cellulose derivative (e.g., methyl cellulose, carboxymethyl cellulose, hydroxymethyl cellulose, hydroxypropyl cellulose, hydroxypropylmethyl cellulose), gelatin, water-soluble starch, polyacrylic acid (e.g., carbomer), polymethacrylic acid, polyvinyl alcohol, polyethylene glycol, polyvinylpyrrolidone, polycarbophil, ascorbate palmitate ester and the like, with hydroxypropylmethyl cellulose, polyacrylic acid, alginate, gelatin, carboxymethyl cellulose, polyvinylpyrrolidone and polyethylene glycol being preferred. Hydroxypropylmethyl cellulose is especially preferred. A stabilizer may, for example, be cysteine, thiosorbitol, tartatic acid, citric acid, sodium carbonate, ascrobic acid, glycine and sodium sulfite, with citric acid and ascorbic acid being preferred especially.

Each of sublingual, buccal or intraoral instantaneous disintegration formulations can be produced by mixing an inventive compound or concomitant drug with an excipient by a method known per se. If desired, an auxiliary agent described above, such as lubricant, iotonizing agent, hydrophilic carrier, water-dispersible polymer, stabilizer, colorant, sweetener and preservative, may also be incorporated. After mixing the components described above simultaneously or at a certain time interval, the mixture is compacted and molded into each of sublingual, buccal or intraoral instantaneous disintegration formulations. For the purpose of obtaining a suitable hardness, a solvent such as water and alcohol may be employed to wet the mixture before or after the tablet impaction, and then dried finally.

When a oral mucosa plaster (film) is to be molded, an inventive compound or concomitant drug and a water-dispersible polymer (preferably, hydroxypropyl cellulose, hydroxypropylmethyl cellulose) and excipient described above are dissolved in a solvent such as water, and then the resultant solution is casted into a film. Additives may also be added such as plasticizers, stabilizers, antioxidants, preservatives, colorants, buffering agents and sweeteners. A glycol such as polyethylene glycol or propylene glycol may be added for the purpose of imparting a film with an appropriate elasticity, and a bioadhesive polymer (e.g., polycarbophile, carbopol) may be added for the purpose of enhancing the adhesion of the film to the oral mucosal lining. The casting may be accomplished by pouring a solution onto a non-adhesive surface, spreading the solution using a coater such as a doctor blade into a uniform thickness (preferably about 10 to 1000 microns), and then drying the solution to form a film. The film thus formed is dried at room temperature or with warming, and then cut into pieces each having a desired surface area.

A preferred intraoral instantaneous disintegration formulation may, for example, be a rapid diffusion formulation in the form of a solid network consisting of an inventive compound or concomitant drug together with a water-soluble or water-diffusable carrier which is inert to the inventive compound or concomitant drug. Said network is obtained by sublimating a solvent from a solid composition consisting of a solution of an inventive compound or concomitant drug in a suitable solvent.

In addition to an inventive compound or concomitant drug, a matrix-forming agent and a secondary component are contained preferably in the composition of said intraoral instantaneous disintegration formulation.

Said matrix-forming agents may, for example, be an animal or vegetable protein such as a gelatin, dextrin and soybean, wheat and psyllium seed proteins; a gummy material such as gum Arabic, guar gum, agar and xanthane gum; polysaccharide; alginate; carboxymethyl cellulose; carrageenan; dextran; pectin; synthetic polymer such as polyvinylpyrrolidone; a material derived from a gelatin-gum Arabic complex. Those which are also included are saccharides such as mannitol, dextrose, lactose, galactose and trehalose; cyclic saccharides such as cyclodextrin; inorganic salts such as sodium phosphate, sodium chloride and aluminium silicate; amino acids having 2 to 12 carbon atoms such as glycine, L-alanine, L-aspartic acid, L-glutamic acid, L-hydroxyproline, L-isoleucine, L-leucine and L-phenylalanine.

One or more matrix-forming agents may be introduced into a solution or suspension before solidification. Such a matrix-forming agent may be present in addition to a surfactant, or may be present in the absence of the surfactant. The matrix-forming agent serves not only to form a matrix itself, but also to aid in maintaining an inventive compound or concomitant drug as being diffused in the solution or suspension.

A secondary agent may be contained in a composition such as a preservative, antioxidant, surfactant, thickening agent, colorant, pH modifier, flavor, sweetener or taste masking agent. A suitable colorant may, for example, be iron oxide red, black and yellow, FD&C dyes available from ERIS AND EVERALD such as FD&C Blue No.2 and FD&C Red No.40. A suitable flavor may, for example, be mint, raspberry, licorice, orange, lemon, grape fruit, caramel, vanilla, cherry and grape flavor as well as a combination thereof. A suitable pH modifier may, for example, be citric acid, tartaric acid, phosphoric acid, hydrochloric acid and maleic acid. A suitable sweetener may, for example, be aspartame, acesulfame K and thaumatine. A suitable taste masking agent may, for example, be sodium bicarbonate, ion exchange resin, cyclodextrin inclusion compound, adsorbent and microencapsulated apomorphine.

A formulation contains an inventive compound or concomitant drug in an amount usually of about 0.1 to about 50% by weight, preferably about 0.1 to about 30% by weight, and is preferably a formulation (sublingual or buccal formulation described above) which allows 90% or more of the inventive compound or concomitant drug to be dissolved (in water) within a time period of about 1 to about 60 minutes, preferably about 1 minutes to about 15 minutes, more preferably about 2 minutes to about 5 minutes, or a intraoral instantaneous disintegration formulation which disintegrates within about 1 to about 60 seconds, preferably about 1 to about 30 seconds, more preferably about 1 to about 10 seconds after being placed in the oral cavity.

The amount of an excipient described above based on the entire formulation is about 10 to about 99% by weight, preferably about 30 to about 90% by weight. The amount of β-cyclodextrin or β-Cyclodextrin derivative based on the entire formulation is about 0 to about 30% by weight. The amount of a lubricant based on the entire formulation is about 0.01 to about 10% by weight, preferably about 1 to about 5% by weight. The amount of an isotonizing agent based on the entire formulation is about 0.1 to about 90% by weight, preferably about 10 to about 70% by weight. The amount of a hydrophilic carrier based on the entire formulation is about 0.1 to about 50% by weight, preferably about 10 to about 30% by weight. The amount of a water-dispersible polymer based on the entire formulation is about 0.1 to about 30% by weight, preferably about 10 to about 25% by weight. The amount of a stabilizer based on the entire formulation is about 0.1 to about 10% by weight, preferably about 1 to about 5% by weight. The formulation described above may further contain additives if desired such as colorants, sweeteners and preservatives.

[4] A Solid Dispersion of an Inventive Compound or a Concomitant Drug and a Method for Producing the Same When a compound of the invention [hereinafter sometimes referred to as lipid-rich plaque regressing substance] or a concomitant drug is hardly soluble or insoluble in water, then it may be formulated into a solid dispersion (e.g., a solid dispersion containing a hardly water-soluble or water-insoluble lipid-rich plaque regressing substance and a hydrophilic polymer).

"A solid dispersion" mentioned here means a dispersion in which one more active ingredients (preferably, amorphous active ingredients) is dispersed in a carrier or a matrix thereof which is inert in the form of a solid (e.g., a hydrophilic polymer), which can be prepared for example by a fusion method, solvent method or fusion-solvent method (J. Pharm. Sci., Vol. 60, 1281–1301, 1971).

While the mean particle size of a solid dispersion is not limited particularly, the lower limit is usually about 0.05 $\mu$m or more, preferably about 0.1 $\mu$m or more, more preferably about 1 $\mu$m or more, further preferably 3 $\mu$m or more, while the upper limit is about 30 mm or less, preferably about 100 $\mu$m or less, more preferably about 50 $\mu$m or less, further preferably about 10 $\mu$m or less.

A hydrophilic polymer employed in said solid dispersion may, for example, be a water-soluble polymer, enteric coating polymer, gastric coating polymer and the like, with an enteric coating polymer being employed preferably.

A water-soluble polymer may, for example, be [1] a cellulose derivative including a hydroxyalkyl cellulose such as hydroxypropyl cellulose and hydroxypropylmethyl cellulose and an alkyl cellulose such as methyl cellulose and ethyl cellulose; [2] a polyalkenyl pyrrolidone such as polyvinyl pyrrolidone; [3] a polyalkylene glycol such as polyethylene glycol and the like.

An enteric coating polymer may, for example, be a hydroxyalkyl cellulose phthalate such as hydroxypropylmethyl cellulose phthalate; a hydroxyalkyl cellulose acetate succinate such as hydroxypropylmethyl cellulose acetate succinate; a carboxyalkyl cellulose such as carboxymethylethyl cellulose; cellulose acetate phthalate; a copolymer of ethyl acrylate and methacrylic acid such as methacrylic acid copolymer L-100-55; a copolymer of methyl methacrylate and methacrylic acid such as methacrylic acid copolymer L, methacrylic acid copolymer S and the like.

A gastric coating polymer may, for example, be an aminoalkylmethacrylate copolymer E; polyvinyl acetal amino acetate and the like.

In addition, a copolymer of ethyl acrylate and methyl methacrylate containing a small amount of a quaternary ammonium group such as methacrylic acid copolymer RL and methacrylic copolymer RS, a hydrophilic polymer capable of dispersing a hardly water-soluble or water-insoluble lipid-rich plaque regressing substance such as carboxymethyl cellulose, carboxyvinyl polymer, polyvinyl alcohol, gum arabic, sodium alginate, alginic acid propylene glycol ester, agar, gelatin, chitosan and the like may be employed. Any of these hydrophilic polymers can be employed in combination with each other.

Among those listed above, preferred hydrophilic polymers are a hydroxyalkyl cellulose, alkyl cellulose, polyalkenyl pyrrolidone, polyalkylene glycol, methacrylic acid copolymer and carboxymethyl cellulose and the like, and those preferred especially are hydroxypropylmethyl cellulose phthalate, polyvinyl pyrrolidone, hydroxypropylmethyl cellulose, carboxymethylethyl cellulose, methacrylic acid copolymer L and the like.

Any of the solid dispersions described above may contain additives employed generally in the field of the pharmaceutical formulations.

Such additives are pharmaceutically acceptable carriers such as various organic and inorganic carrier materials employed customarily as pharmaceutical materials, and are incorporated as excipients, lubricants, binders, disintegrants and surfactants. If desired, pharmaceutical additives such as preservatives, antioxidants, colorants and sweeteners may also be added.

Preferred examples of excipients are lactose, sugar, D-mannitol, starch, crystalline cellulose, sucrose, porous starch, mannitol, calcium silicate (trade name: Fluorite RE), magnesium methasilicate aluminate (trade name: NEUSILIN), light silicic anhydride (trade name: CYSILIA), sugar/starch spherical granule (trade name: nonpareil), crystalline cellulose/carboxymethyl cellulose (trade name: Avicel RC), hydroxypropyl starch and the like.

Preferred examples of lubricants are magnesium stearate, calcium stearate, talc, colloidal silica and the like.

Preferred examples of binders are crystalline cellulose, sugar, D-mannitol, dextrin, hydroxypropyl cellulose, hydroxypropylmethyl cellulose, polyvinyl pyrrolidone and the like.

Preferred examples of disintegrants are starch, carboxymethyl cellulose, calcium carboxymethyl cellulose, croscarmellose sodium, sodium carboxymethyl starch, methyl cellulose (trade name: METHOLOSE SM), croscarmellose sodium, carmellose calcium, low-substituted hydroxypropyl cellulose, sodium starch glycolate, partially alpha-derivatized starch and the like.

Lubricants employed are, for example, talc, crystalline cellulose, magnesium stearate, corn starch, magnesium oxide and the like.

Surfactants employed are, for example, polyoxyethylene polyoxypropylene glycol (trade name: Pluronic), glycerin fatty acid ester, sucrose fatty acid ester, polyoxyethylene hydrogenated castor oil, polysorbate 80, cetanol and the like.

Preferred examples of preservatives are p-oxybenzoates, chlorobutanol, benzyl alcohol, phenethyl alcohol, dehydroacetic acid, sorbic acid and the like.

Preferred examples of antioxidants are sulfites, ascorbic acid and the like.

Any of these additives may be used alone or in combination with each other.

While a solid dispersion described above can be produced by a method known per se, it can specifically be produced for example by a spray dry method, solvent method such as a rotary evaporation method; a fusion method such as twin-screw extruder method; mixing pulverization method; ultrasonic method using an ultrasonic molding machine and the like.

More specifically, a solid dispersion described above can be produced by a solvent method shown below:

(1) dissolvong a lipid-rich plaque regressing substance in a suitable organic solvent;
(2) to this solution, adding a hydrophilic polymer to prepare a suspension;
(3) to this suspension or solution, adding additives such as excipients, disintegrants, lubricants and surfactants if necessary; and then,
(4) distilling off the organic solvent from this homogenous suspension under reduced pressure or atmospheric pressure by a conventional method, for example, a spray dry method, rotary evaporation method and the like.

For obtaining a further homogenous solid dispersion, the homogenous suspension is prepared in Step (2) described above and then subjected sequentially to the following steps:

(5) dissolving a suspension prepared in Step (2) described above in a suitable organic solvent;
(6) adding additives such as excipients, disintegrants, lubricants and surfactants if necessary; and then,
(7) distilling off the organic solvent under reduced pressure or atmospheric pressure by a conventional method, for example, a spray dry method, rotary evaporation method and the like.

An organic solvent employed in Step (1) described above is not limited specifically provided that it can dissolve a hardly water-soluble or water-insoluble lipid-rich plaque regressing substance and a hydrophilic polymer, and may, for example, be an alcohol such as methanol, ethanol, propanol, isopropyl alcohol, butanol, monomethoxyethanol, ethylene glycol monomethyl ether and the like; an ether such as diethyl ether, dibutyl ether, diisopropyl ether, dioxane, tetrahydrofuran, ethylene glycol and the like; an aliphatic hydrocarbon such as n-hexane, cyclohexane, n-heptane and the like; an aromatic hydocarbon such as benzene, toluene, xylene and the like; a nitrite such as acetonitrile; an organic acid such as acetic acid, propionic acid and the like; an ester such as ethyl acetate; an aliphatic halogenated hydrocarbon such as dichloromethane, dichloroethane, chloroform and the like; a ketone such as acetone and methylethyl ketone; an amide such as dimethylformamide, dimethylacetamide and the like; or a mixture thereof in a suitable ratio. Among those listed above, a low-boiling solvent such as a ketone or alcohol is preferred, with acetone and ethanol being especially preferred.

While the operating conditions such as the treatment temperature and the treatment time period may vary depending on the starting compounds and organic solvent employed, the treatment temperature is usually 200° C. or below.

In a fusion method, a hardly water-soluble or water-insoluble lipid-rich plaque regressing substance is heated at a temperature higher than the melting point to fuse it, and then a hydrophilic polymer, and additives such as excipients, disintegrants, lubricants and surfactants, if necessary, are dissolved in it, and then it is cooled rapidly to accomplish the production. For example, in a twin-screw extruder method, a hardly water-soluble or water-insoluble lipid-rich plaque regressing substance and a hydrophilic polymer, if necessary together with additives such as excipients, disintegrants, lubricants and surfactants, are mixed mechanically and then heated under a high pressure to fuse the hardly water-soluble or water-insoluble lipid-rich plaque regressing substance at a temperature lower than the melting point, and then the mixture is cooled rapidly to accomplish the production.

In a mixing pulverization method, a hardly water-soluble or water-insoluble lipid-rich plaque regressing substance and a hydrophilic polymer, if necessary together with additives such as excipients, disintegrants, lubricants and surfactants, are mixed mechanically and then pulverized with mixing to accomplish the production.

In an ultrasonic method, a hardly water-soluble or water-insoluble lipid-rich plaque regressing substance and a hydrophilic polymer, if necessary together with additives such as excipients, disintegrants, lubricants and surfactants, are mixed mechanically and then charged into a mortar to pre-mold the mixture, and then irradiated with an ultrasonic wave for example by using a ultrasonic molding machine to accomplish the production.

The amount of a hydrophilic polymer is not limited particularly, and may be any level as long as it can disperse a hardly water-soluble or water-insoluble lipid-rich plaque regressing substance. For example, a preferable weight ratio of a hydrophilic polymer and a hardly water-soluble or water-insoluble lipid-rich plaque regressing substance is 0.01:1 to 100:1, preferably 0.02:1 to 50:1, more preferably 0.1:2 to 20:1, further preferably 0.3:1 to 10:1, still further preferably 1:1 to 10:1, especially 3 to 5 (especially 4):1.

While the amount of an additive is not limited particularly, a preferable weight ratio of an additive such a an excipient, disintegrant, lubricant or surfactant and a hardly water-soluble or water-insoluble lipid-rich plaque regressing substance is usually 0.1:1 to 20:1, preferably 0.3:1 to 10:1, more preferably 1:1 to 3:1.

An organic solvent employed in Step (5) described above is not limited particularly, and may be any solvent as long as it is capable of dissolving the suspension in Step (2) described above such as chloroform and dichloromethane.

A solid dispersion described above can itself be used as an oral pharmaceutical formulation, and may also be formulated as a powder, fine powder, granule, tablet, capsule, injection formulation and the like by an ordinary method.

A pharmaceutical formulation containing a solid dispersion described above may contain the additives described above, namely, colorants, sweeteners, flavors, such as sucrose, lactose, starch, crystalline cellulose, synthetic ammonium silicate, magnesium stearate, talc and other diluents and lubricants in an oral pharmaceutical formulation. The surface of the formulation can be coated to obtain a sustained-release formulation.

Since a lipid-rich plaque regressing substance is usually hardly water-soluble or water-insoluble, the ratio at which it is absorbed actually into blood based on the dose given orally is low, resulting in a problematically low bioavailability.

Nevertheless, various formulations obtained by converting a solid dispersion described above into various dosage forms have markedly improved performances of dissolution, oral absorption or(and) absorption into blood, when compared with a crystal of a hardly water-soluble or water-insoluble lipid-rich plaque regressing substance itself.

Thus, a solid dispersion described above enables the solubilization of a hardly water-soluble or water-insoluble lipid-rich plaque regressing substance, whereby allowing the bioavailability of the hardly water-soluble or water-insoluble lipid-rich plaque regressing substance to be improved dramatically.

The amount of a hardly water-soluble or water-insoluble lipid-rich plaque regressing substance in a solid dispersion described above may vary depending on the dosage form, administration mode, carrier and the like, and it is usually 0.1 to 99% by weight based on the total amount of the formulation.

The amount of a hydrophilic polymer in a solid dispersion described above may vary depending on the dosage form, administration mode, carrier and the like, and it is usually 1 to 99.9% by weight based on the total amount of the formulation.

The amount of an additive in a solid dispersion described above may vary depending on the dosage form, administration mode and the like, and it is usually 0 to 99% by weight based on the total amount of the formulation.

The amount of a solid dispersion described above in an inventive pharmaceutical formulation may vary depending on the dosage form, administration mode, carrier and the like, and it is usually 0.1 to 100% by weight based on the total amount of the formulation.

The amount of additives in an inventive pharmaceutical formulation may vary depending on the dosage form, administration mode and the like, and it is usually 0 to 99.9% by weight based on the total amount of the formulation.

While the dose of an inventive concomitant formulation may vary depending on the type of the inventive compound, the subject's age, body weight, condition, and the dosage form as well as administration mode and duration, for example, the daily dose in a patient having hyperlipidemia (adult, body weight: about 60 kg) is about 0.01 to about 1000 mg/kg, preferably about 0.01 to about 100 mg/kg, more preferably about 0.1 to about 100 mg/kg, particularly about 0.1 to about 50 mg/kg, especially about 1.5 to about 30 mg/kg as an inventive compound, which is given intravenously at once or in several portions. It is a matter of course that the dose may vary depending on various factors as described above, and a less amount may sometimes be sufficient and an excessive amount should sometimes be required.

A concomitant drug may be employed in any amount within the range causing no problematic side effects. The daily dose of a concomitant drug is not limited particularly and may vary depending on the severity of the disease, the subject's age, sex, body weight and susceptibility as well as time and interval of the administration and the characteristics, preparation, type and active ingredient of the pharmaceutical formulation, and the daily oral dose per kg body weight in a mammal is about 0.001 to 2000 mg, preferably about 0.01 to 500 mg, more preferably about 0.1 to about 100 mg as medicaments, which is given usually in 1 to 4 portions.

When an inventive concomitant formulation is administered, it may be administered at the same time, but it is also possible that a concomitant drug is first administered and then an inventive compound is administered, or that the inventive compound is first administered and then the concomitant drug is administered. When such an intermittent administration is employed, the time interval may vary depending on the active ingredient administered, the dosage form and the administration mode, and for example, when the concomitant drug is first administered, the inventive compound may be administered within 1 minute to 3 days, preferably 10 minutes to 1 day, more preferably 15 minutes to 1 hour after the administration of the concomitant drug. When the inventive compound is first administered, for example, then the concomitant drug may be administered within 1 minute to 1 day, preferably 10 minutes to 6 hours, more preferably 15 minutes to 1 hour after the administration of the inventive compound.

In a preferred administration mode, for example, about 0.001 to 200 mg/kg of a concomitant drug formulated as an oral formulation is given orally as a daily dose, and, after about 15 minutes, about 0.005 to 100 mg/kg of an inventive compound formulated as an oral formulation is given orally as a daily dose.

The invention is further detailed in the following Examples, Formulation Examples and Experiments, which are not intended to restrict the invention.

A $^1$H NMR spectrum was measured by VARIAN GEMINI 200 (200 MHz) spectrophotometer using tetramethylsilane as an internal standard, and entire δ values are represented in ppm. A value indicated for a solvent mixture is a volume ratio of each solvent, unless otherwise specified. A % is a % by weight, unless otherwise specified. A ratio of the elution solvent in a chromatography on a silica gel is a volume ratio, unless otherwise specified. Room temperature (ambient temperature) employed here usually means a temperature from about 20 to about 30° C.

Each symbol in Examples is defined as shown below.

AcOEt: ethyl acetate, Me: methyl, Et: ethyl, THF: tetrahydrofuran, IPE: isopropylether, Et$_2$O: diethyl ether, decomp.: decomposition, s: singlet, d: doublet, t: triplet, q: quartet, dd: double doublet, dt: double triplet, m: multiplet, br: broad, J: coupling constant, Py: pyridyl, DBU: diazabicycloundecene, DMF: dimethylformamide, DPPA: diphenylphosphoryl azide, hex: hexane, Ac: acetyl, Ph: phenyl, Ts: tosyl, mCPBA: m-chloroperbenzoic acid, $^t$Bu: tert-butyl.

EXAMPLES

Reference Example 1

Synthesis of 6,7-dichloro-2-oxo-4-phenyl-2H-chromene-3-carboxylic acid

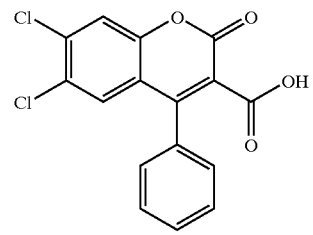

A mixture of (4,5-dichloro-2-hydroxyphenyl) (phenyl) methanone (1.5 g), diethyl malonate (1.28 ml) and DBU (0.25 ml) was stirred at 170° C. for 30 minutes. The reaction mixture was dissolved in ethyl acetate (50 ml), and washed with water followed by a 1 N solution of hydrochloric acid and a saturated aqueous solution of sodium chloride. After drying over magnesium sulfate, the solvent was distilled off under reduced presurre, and the residue was purified by a column chromatography (packing: silica gel, eluent: ethyl acetate-hexane=1:9). The resultant crude product of ethyl 6,7-dichloro-2-oxo-4-phenyl-2H-chromene-3-carboxylate was dissolved in acetic acid (10 ml) and concentrated hydrochloric acid (5 ml), and heated under reflux for 1 hour. The reaction solution was concentrated under reduced pressure, and the resultant residue was dissolved in a solvent mixture of THF (10 ml) and ethyl acetate (50 ml), and then washed with water followed by a saturated aqueous solution of sodium hydrogen carbonate and a saturated aqueous solution of sodium chloride. After drying over magnesium sulfate, the solvent was distilled off under reduced pressure, and the residue was purified by recrystallization from ethyl acetate to obtain the title compound (0.65 g, yield: 34%).

Melting point: 233–234° C.
NMR (CDCl$_3$) δ: 7.29–7.40 (3H, m), 7.48–7.58 (4H, m).
IR(KBr): 3400–2400, 1748, 1717 cm$^{-1}$.
Analysis for C$_{16}$H$_8$O$_4$Cl$_2$: Calcd (%): C:57.34H:2.41 Found (%): C:57.30H:2.50.

Reference Example 2–6

The compounds of table 1 were obtained by the method similar to that in Reference Example 1.

TABLE 1

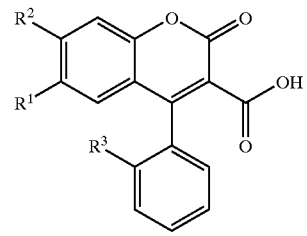

| Ref.Ex. number | R$^1$ | R$^2$ | R$^3$ | Yield (%) | Melting Point (° C.) (Recrystallization solvent) |
|---|---|---|---|---|---|
| 2 | Cl | Me | H | 63 | 227–228 (AcOEt) |
| 3 | Cl | Me | Me | 58 | 226–227 (AcOEt) |
| 4 | Me | Me | H | 81 | 205–206 (AcOEt) |
| 5 | Me | Me | Me | 27 | 222–223 (AcOEt) |
| 6 | (CH$_2$)$_4$ | | H | 7 | 92–93 (AcOEt) |

Reference Example 7

Synthesis of (6,7-dichloro-2-oxo-4-phenyl-2H-chromen-3-yl)acetic acid

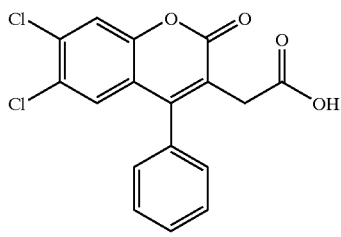

A solution of 6,7-dichloro-2-oxo-4-phenyl-2H-chromene-3-carboxylic acid (0.8 g) in THF (10 ml) was combined with DMF (1 drop) and oxalyl chloride (0.31 ml), and stirred at room temperature for 1 hour. After the reaction solution was concentrated under reduced pressure, the resultant residue was dissolved in THF (10 ml), and to which a solution of diazomethane prepared from N-methyl-N'-nitro-N-nitrosoguanidine (1.68 g) and potassium hydroxide (3.0 g) in ether (30 ml) was added dropwise. After the effervescence had ceased, the reaction solution was concentrated under reduced pressure. The resultant residue was dissolved in methanol (50 ml), combined with silver oxide, and heated under reflux for 30 minutes. After the insolubles were filtered off, the filtrate was concentrated under reduced pressure, and the residue was purified by a column chromatography (packing: silica gel, eluent: ethyl acetate-hexane= 1:4). The resultant crude product of methyl (6,7-dichloro-2-oxo-4-phenyl-2H-chromen-3-yl)acetate was dissolved in acetic acid (5 ml) and concentrated hydrochloric acid (2.5 ml), and heated under reflux for 1 hour. The reaction solution was concentrated under reduced pressure, and the resultant residue was dissolved in a solvent mixture of THF (10 ml) and ethyl acetate (50 ml), and then washed with water followed by a saturated aqueous solution of sodium hydrogen carbonate and a saturated aqueous solution of sodium chloride. After drying over magnesium sulfate, the solvent was distilled off under reduced pressure, and the residue was purified by recrystallization from ethyl acetate to obtain the title compound (0.52 g, yield: 62%).

Melting point: 222–223° C.

NMR (CDCl$_3$) δ: 3.43 (2H, s), 7.10 (1H, s), 7.20–7.36 (2H, m), 7.50–7.64 (4H, m.).

IR(KBr): 3400–2400, 1725, 1599 cm$^{-1}$.

Analysis for $C_{17}H_{10}O_4Cl_2 \cdot 0.3H_2O$ Calcd (%): C:57.59 H:3.01 Found (%): C:57.44 H:2.99.

Reference Example 8–12

The compounds of table 2 were obtained by the method similar to that in Reference Example 7.

TABLE 2

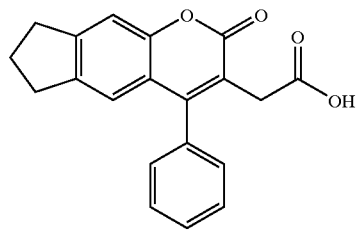

| Ref.Ex. number | R$^1$ | R$^2$ | R$^3$ | Yield (%) | Melting Point (° C.) (Recrystallization solvent) |
|---|---|---|---|---|---|
| 8 | Cl | Me | H | 50 | 216–217 (AcOEt) |
| 9 | Cl | Me | Me | 45 | 204–205 (AcOEt) |
| 10 | Me | Me | H | 43 | 228–229 (AcOEt) |
| 11 | Me | Me | Me | 49 | 205–206 (AcOEt) |
| 12 | (CH$_2$)$_4$ | | H | 52 | 196–197 (AcOEt) |

Reference Example 13

Synthesis of (2-oxo-4-phenyl-2,6,7,8-tetrahydrocyclopenta[g]chromen-3-yl)acetic acid A solution of (6-hydroxy-2,3-dihydro-1H-inden-5-yl)(phenyl)methanone (1.0 g) and triethylamine (0.98 ml) in THF (20 ml) was combined with ethyl succinyl chloride (0.55 ml) at 0° C., and stirred for 1 hour. The reaction solution was combined with water, and the product was extracted with ethyl acetate. The extract was washed with a 1 N solution of hydrochloric acid followed by a saturated aqueous solution of sodium chloride. After drying over magnesium sulfate, the solvent was distilled off under reduced pressure. The resultant residue was dissolved in toluene (10 ml), combined with DBU (0.25 ml), and heated under reflux for 2.5 hours. After cooling, the reaction solution was diluted with ethyl acetate (60 ml), and washed with water followed by a 1 N solution of hydrochloric acid and a saturated aqueous solution of sodium chloride. After drying over magnesium sulfate, the solvent was distilled off under reduced pressure, and the residue was purified by a column chromatography (packing: silica gel, eluent: ethyl acetate-hexane=1:2). The resultant crude product of ethyl (2-oxo-4-phenyl-2,6,7,8-tetrahydrocyclopenta[g]chromen-3-yl)acetate was dissolved in acetic acid (20 ml) and concentrated hydrochloric acid (10 ml), and heated under reflux for 1 hour. The reaction solution was concentrated under reduced pressure, and the resultant residue was dissolved in a solvent mixture of THF (5 ml) and ethyl acetate (50 ml), and then washed with water followed by a saturated aqueous solution of sodium hydrogen carbonate and a saturated aqueous solution of sodium chloride. After drying over magnesium sulfate, the solvent was distilled off under reduced pressure, and the residue was purified by recrystallization from ethyl acetate-isopropyl ether to obtain the title compound (0.95 g, yield: 70%).

Melting point: 216–218° C.

NMR (CDCl$_3$) δ: 2.09 (2H, m), 2.81 (2H, d, J=7 Hz), 2.99 (2H, d, J=7 Hz), 3.41 (2H, s), 6.82 (1H, s), 7.20–7.30 (3H, m), 7.50–7.60 (3H, m).

IR(KBr): 3400–2400, 1714, 1622 cm$^{-1}$.

Analysis for C$_{20}$H$_{16}$O$_4$ Calcd (%): C:74.99 H:5.03 Found (%): C:74.75 H:5.13.

Reference Example 14–20

The compounds of table 3 were obtained by the method similar to that in Reference Example 13.

TABLE 3

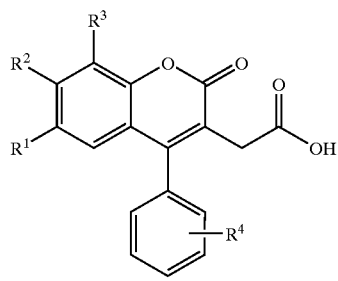

| Ref.Ex. number | R$^1$ | R$^2$ | R$^3$ | R$^4$ | Yield (%) | Melting Point (° C.) (Recrystallization solvent) |
|---|---|---|---|---|---|---|
| 14 | Cl | Cl | Cl | H | 13 | 244-246 (AcOEt) |
| 15 | F | F | H | H | 64 | 164-166 (IPE) |
| 16 | Me | Cl | H | H | 65 | 222-224 (AcOEt) |
| 17 | (CH$_2$)$_3$ | | H | 3-Me | 63 | 183-184 (AcOEt) |
| 18 | (CH$_2$)$_3$ | | H | 4-Me | 81 | 231-233 (AcOEt) |
| 19 | (CH$_2$)$_3$ | | H | 3,4-di-Me | 70 | 193-194 (AcOEt) |
| 20 | (CH$_2$)$_3$ | | H | 4-F | 86 | 231-234 (AcOEt) |

Reference Example 21
Synthesis of Ethyl 2-(7-chloro-6-methyl-2-oxo-4-phenyl-2H-chromen-3-yl)acetate

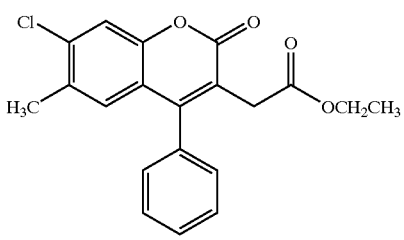

A solution of (4-chloro-2-hydroxy-5-methylphenyl)(phenyl)methanone (5.0 g) and triethylamine (5.65 ml) in THF (100 ml) was combined with ethyl succinyl chloride (3.47 ml) at 0° C., and stirred for 1 hour. The reaction solution was combined with water, and the product was extracted with ethyl acetate. The extract was washed with a 1 N solution of hydrochloric acid followed by a saturated aqueous solution of sodium chloride, and after drying over magnesium sulfate, the solvent was distilled off under reduced pressure. The resultant residue was dissolved in toluene (50 ml), combined with DBU (1.25 ml), and heated under reflux for 2.5 hours. After cooling, the reaction solution was diluted with ethyl acetate (100 ml), and washed with water followed by a 1 N solution of hydrochloric acid and a saturated aqueous solution of sodium chloride. After drying over magnesium sulfate, the solvent was distilled off under reduced pressure, and the residue was purified by a column chromatography (packing: silica gel, eluent: ethyl acetate-hexane=1:4) and further purified by recrystallization from ethyl acetate-hexane to obtain the title compound (3.86 g, yield: 53%).

Melting point: 132–133° C.

NMR (CDCl$_3$) δ: 1.23 (3H, t, J=7 Hz), 2.28 (2H, s), 3.36 (2H, s), 4.13 (2H, t, J=7 Hz), 6.84 (1H, s), 7.20–7.35 (2H, m), 7.41 (1H, s), 7.45–7.60 (3H, m).

IR(KBr): 1728, 1609, 1366, 1188 cm$^{-1}$.

Analysis for C$_{21}$H$_{17}$ClO$_4$ Calcd (%): C:67.32 H:4.80 Found (%): C:67.55 H:5.13.

Reference Example 22–23

The compounds of table 4 were obtained by the method similar to that in Reference Example 21.

TABLE 4

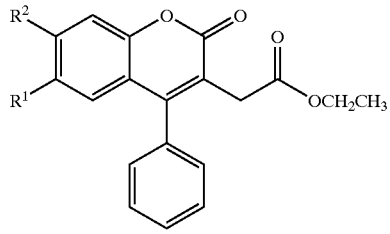

| Ref.Ex. number | R$^1$ | R$^2$ | Yield (%) | Melting Point (° C.) (Recrystallization solvent) |
|---|---|---|---|---|
| 22 | Me | H | 78 | 91–92 (Hexane) |
| 23 | Cl | Me | 71 | oil |

Reference Example 24

Synthesis of 2-[6-(bromomethyl)-7-chloro-2-oxo-4-phenyl-2H-chromen-3-yl]acetic acid

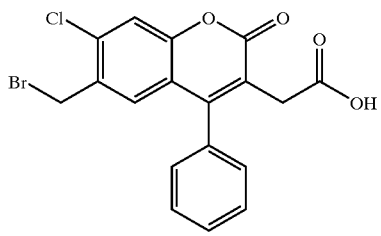

A solution of ethyl(7-chloro-6-methyl-2-oxo-4-phenyl-2H-chromen-3-yl)acetate (3.5 g) in ethyl acetate (50 ml) was combined with N-bromosuccinimide (2.1 g) and 2,2'-azoisobutyronitrile (48.3 mg), and heated under reflux for 1 hour. After cooling, the reaction solution was washed with water followed by a saturated aqueous solution of sodium hydrogen carbonate and a saturated aqueous solution of sodium chloride. After drying over magnesium sulfate, the solvent was distilled off under reduced pressure, and the residue was purified by a silica gel column chromatography (eluent: ethyl acetate-hexane=1:4) to obtain the crude crystal (approximately 2.6 g) of ethyl 2-[6-(bromomethyl)-7-chloro-2-oxo-4-phenyl-2H-chromen-3-yl]acetate. The crude crystal was dissolved in acetic acid (50 ml) and concentrated hydrochloric acid (25 ml), and heated under reflux for 30 minutes. The reaction solution was concentrated under reduced pressure, and the resultant residue was dissolved in a solvent mixture of THF (10 ml) and ethyl acetate (50 ml), and then washed with water followed by a saturated aqueous solution of sodium hydrogen carbonate and a saturated aqueous solution of sodium chloride. After drying over magnesium sulfate, the solvent was distilled off under reduced pressure, and the residue was washed with ethyl acetate to obtain a crude crystal (1.78 g, yield: 44%) of the title compound. The compound was used in the next reaction without further purification. NMR (CDCl$_3$) δ: 3.43 (2H, s), 4.58 (2H, s), 7.11 (1H, s), 7.20–7.30 (2H, m), 7.48 (1H, s), 7.50–7.65 (3H, m).

Reference Example 25–26

The compounds of table 5 were obtained by the method similar to that in Reference Example 24.

TABLE 5

| Ref.Ex. number | R$^1$ | R$^2$ | Yield (%) | NMR (CDCl$_3$) |
|---|---|---|---|---|
| 25 | CH$_2$Br | H | 50 | 3.44 (2H, s), 4.49 (2H, s), 7.03 (1H, d, J=2H), 7.20–7.35 (1H, m), 7.41 (1H, d, J=8 Hz), 7.50–7.65 (5H, m). |
| 26 | Cl | CH$_2$Br | 43 | 3.44 (2H, s), 4.71 (2H, s), 7.06 (1H, s), 7.20–7.70 (6H, m). |

Reference Example 27
Synthesis of ethyl(2,8-oxo-4-phenyl-2,6,7,8-tetrahydroxycyclopenta[g]chromen-3-yl)acetate

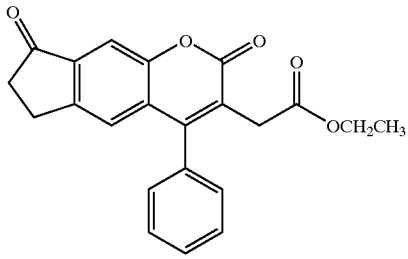

A suspension of chromium oxide (33 g) in methylene chloride (300 ml) was combined with 3,5-dimethylpyrazole (32 g) at −10° C. in one portion. After stirring at the same temperature for 15 minutes, ethyl(2-oxo-4-phenyl-2,6,7,8-tetrahydrocyclopenta[g]chromen-3-yl)acetate was added. After the reaction solution was stirred at −10° C. for 2 hours, and combined with water, and the organic layer was washed with diluted hydrochloric acid and water, and dried over magnesium sulfate. The solvent was distilled off under reduced pressure, the resultant residue was purified by a silica gel column chromatography (eluent: ethyl acetate), and further purified by recrystallization from ethyl acetate to obtain the title compound (1.2 g, yield: 15%).

Melting point: 145–148° C.
NMR (CDCl$_3$) δ: 1.23 (3H, t, J=9 Hz), 2.75 (2H, t, J=6 Hz), 3.08 (2H, t, J=6 Hz), 3.41 (2H, s), 4.14 (2H, q, J=9 Hz), 7.10 (1H, s), 7.28 (2H, m), 7.55 (3H, m), 7.71 (1H, s).
IR(KBr): 2980, 1715, 1615, 1563 cm$^{-1}$.
Analysis for C$_{22}$H$_{18}$O$_5$ Calcd (%): C:72.92H:5.01 Found (%): C:73.15H:5.20

Reference Example 28
Synthesis of (2,8-dioxo-4-phenyl-2,6,7,8-tetrahydrocyclopenta[g]chromen-3-yl)acetic acid

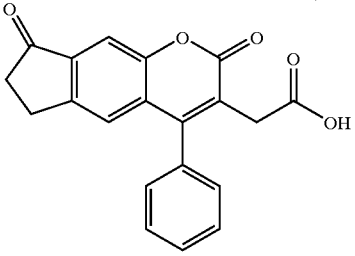

Ethyl(2,8-dioxo-4-phenyl-2,6,7,8-tetrahydrocyclopenta[g]chromen-3-yl)acetate (1.2 g) was dissolved in acetic acid (20 ml) and concentrated hydrochloric acid (10 ml), and heated under reflux for 30 minutes. The reaction solution was concentrated under reduced pressure, and the resultant residue was dissolved in a solvent mixture of THF (10 ml) and ethyl acetate (50 ml), and then washed with water followed by a saturated aqueous solution of sodium hydrogen carbonate and a saturated aqueous solution of sodium chloride. After drying over magnesium sulfate, the solvent was distilled off under reduced pressure, and the residue was purified by recrystallization from ethyl acetate to obtain the title compound (0.87 g, yield: 79%).

Melting point: 240° C. (decomp.).
NMR (CDCl$_3$+DMSO-d$_6$ 1 drop) δ: 2.74 (2H, t, J=6 Hz), 3.08 (2H, t, J=6 Hz), 3.40 (2H, s), 7.11 (1H, s), 7.32 (2H, m), 7.56 (3H, m), 7.68 (1H, s)
IR(KBr): 3400–2400, 1713 cm$^{-1}$.
Analysis for C$_{20}$H$_{14}$O$_5$ Calcd (%): C:71.85H:4.22 Found (%): C:71.40H:4.50.

Example 1
Synthesis of N-(2,6-dimethoxyphenyl)-2-(2-oxo-4-phenyl-2,6,7,8-tetrahydrocyclopenta[g]chromen-3-yl)acetamide

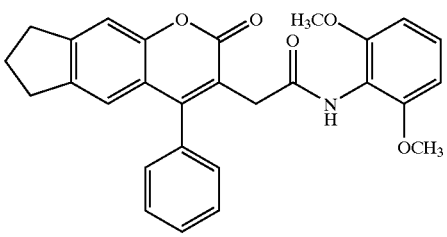

A solution of (2-oxo-4-phenyl-2,6,7,8-tetrahydrocyclopenta[g]chromen-3-yl)acetic acid (150 mg) in THF (10 ml) was combined with dimethylformamide (DMF, 1 drop) and oxalyl chloride (0.06 ml), and stirred at room temperature for 30 minutes. The reaction solution was concentrated under reduced pressure, and the resultant residue was dissolved in THF (10 ml), and added dropwise to a solution of 2,6-dimethoxyaniline (79 mg) and triethylamine (0.1 ml) in THF (5 ml). After stirring at room temperature for 1 hour, the solvent was distilled off under reduced pressure, and the resultant residue was combined with water, and extracted with ethyl acetate. The extract was washed with diluted hydrochloric acid followed by a 1 N solution of sodium hydroxide and water, dried over magnesium sulfate, and then concentrated. The resultant residue was purified by recrystallization from ethyl acetate-THF to obtain the title compound (146 mg, yield: 64%).

Melting point: 213–215° C.

NMR (CDCl₃) δ: 2.09 (2H, m), 2.81 (2H, t, J=7 Hz), 2.99 (2H, t, J=7 Hz), 3.46 (2H, br) 3.78 (6H, s), 6.54 (2H, d, J=8 Hz), 6.85 (1H, s), 7.14 (1H, t, J=8 Hz), 7.26 (1H, s), 7.43 (2H, m), 7.50 (1H, m).

IR(KBr): 1707, 1686, 1508 cm⁻¹.

Analysis for $C_{28}H_{25}NO_5 \cdot 0.2H_2O$ Calcd (%): C:73.25 H:5.58 N:3.05 Found (%): C:73.04 H:5.79 N:3.14.

Example 2–14

The compounds of table 6 were obtained using (2-oxo-4-phenyl-2,6,7,8-tetrahydrocyclopenta[g]chromen-3-yl)acetic acid by the method similar to that in Example 1.

(40 mg) in THF. After stirring at room temperature overnight, the reaction solution was combined with water, and extracted with ethyl acetate. The extract was washed with water, dried over magnesium sulfate, and then concentrated. The resultant residue was purified by recrystallization from ethyl acetate-THF to obtain the title compound as a colorless crystal (60 mg, 28%).

Melting point: 257–259° C.

NMR (CDCl₃) δ: 2.11 (2H, m), 2.27 (3H, m), 2.90 (2H, t, J=7 Hz), 2.99 (2H, t, J=7 Hz), 3.71 (6H, s), 6.54 (1H, s), 6,56 (2H, d, J=8 Hz), 6.86 (1H, bs), 7.06 (1H, s), 7.15 (1H, t, J=8 Hz), 7.33 (5H, m).

IR(KBr): 1699, 1655, 1306, 1144 cm⁻¹.

Analysis for $C_{25}H_{18}N_2O_3Cl_2 \cdot 0.3H_2O$ Calcd (%): C:63.79 H:3.98 N:5.95 Found (%): C:63.56 H:4.10 N:5.71.

TABLE 6

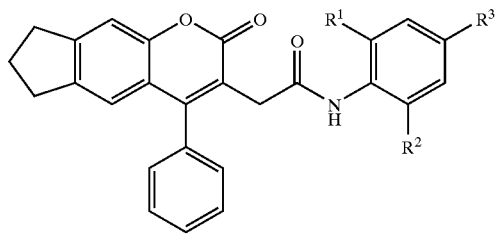

| Example number | R¹ | R² | R³ | Yield (%) | Melting Point (° C.) (Recrystallization solvent) |
|---|---|---|---|---|---|
| 2 | OEt | OEt | H | 64 | 216–219 (AcOEt-THF) |
| 3 | CH(CH₃)₂ | CH(CH₃)₂ | H | 40 | 261–263 (AcOEt-THF) |
| 4 | Et | Et | H | 54 | 279–281 (AcOEt-THF) |
| 5 | Me | OMe | H | 42 | 232–237 (AcOEt) |
| 6 | Et | H | H | 46 | 234–237 (AcOEt-THF) |
| 7 | OMe | H | H | 40 | 219–222 (AcOEt-THF) |
| 8 | OMe | OMe | Me | 73 | 237–239 (AcOEt-THF) |
| 9 | OMe | OH | H | 72 | 179–181 (AcOEt) |
| 10 | OMe | OMe | OH | 40 | 160 (decomp.) (AcOEt) |
| 11 | OH | OMe | OMe | 32 | 170–172 (AcOE) |
| 12 | OCF₃ | H | H | 21 | 191–194 (AcOEt) |
| 13 | OCH(CH₃)₂ | OCH(CH₃)₂ | H | 33 | 181–186 (AcOEt) |
| 14 | cyclopentyloxy | cyclopentyloxy | H | 47 | 224–226 (AcOEt) |

Example 15

Synthesis of N-(3,5-dichloro-4-pyridyl)-2-(2-oxo-4-phenyl-2,6,7,8-tetrahydrocyclopenta[g]chromen-3-yl)acetamide

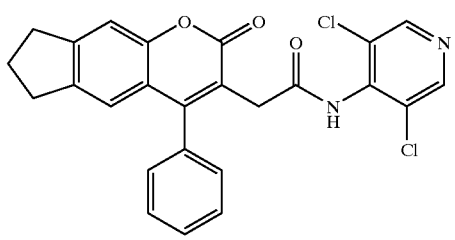

A solution of (2-oxo-4-phenyl-2,6,7,8-tetrahydrocyclopenta[g]chromen-3-yl)acetic acid (150 mg) in THF (10 ml) was combined with DMF (1 drop), and the mixture solution was combined with oxalyl chloride (0.06 ml), and stirred at room temperature for 30 minutes. The reaction solution was concentrated under reduced pressure, and the resultant residue was dissolved in THF (10 ml), and added dropwise to a suspension of 4-amino-3,5-dichloropyridine (100 mg) and sodium hydride (60%, in oil)

Example 16–21

The compounds of table 7 were obtained using (2-oxo-4-phenyl-2,6,7,8-tetrahydrocyclopenta [g] chromen-3-yl)acetic acid by the method similar to that in Example 15.

TABLE 7

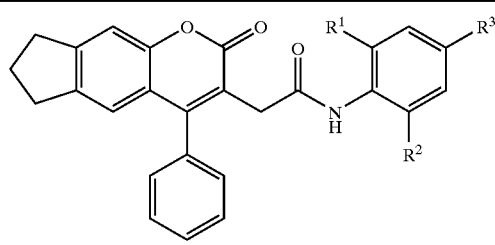

| Example number | R¹ | R² | R³ | Yield (%) | Melting Point (° C.) (Recrystallization solvent) |
|---|---|---|---|---|---|
| 16 | CF₃ | H | Cl | 55 | 198–200 (AcOEt) |
| 17 | F | F | F | 46 | 247–249 (THF-IPE) |
| 18 | CF₃ | F | H | 19 | 194–196 (AcOEt) |

TABLE 7-continued

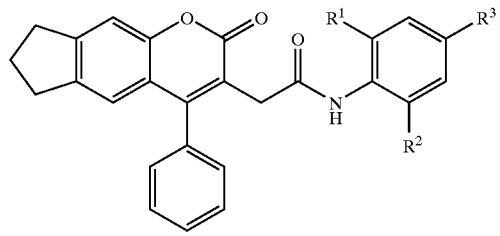

| Example number | R¹ | R² | R³ | Yield (%) | Melting Point (° C.) (Recrystallization solvent) |
|---|---|---|---|---|---|
| 19 | OCF₃ | H | Cl | 84 | 189–191 (AcOEt) |
| 20 | CF₃ | H | F | 57 | 186–187 (AcOEt) |
| 21 | CF₃ | H | CF₃ | 38 | 220–221 (AcOEt) |

Example 22–46

The compounds of table 8 to table 11 were obtained by the method similar to that in Example 1.

TABLE 8

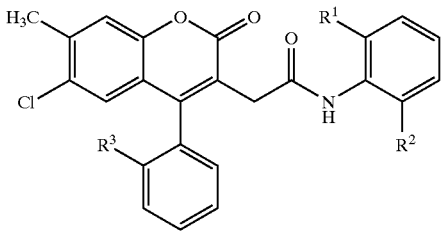

| Example number | R¹ | R² | R³ | Yield (%) | Melting Point (° C.) (Recrystallization solvent) |
|---|---|---|---|---|---|
| 22 | OMe | OMe | H | 57 | 231–232 (AcOEt) |
| 23 | OMe | OMe | Me | 61 | 176–177 (AcOEt) |
| 24 | OEt | OEt | H | 54 | 235–236 (AcOEt) |
| 25 | CH(CH₃)₂ | CH(CH₃)₂ | Cl | 51 | 245–246 (AcOEt) |
| 26 | Et | Et | H | 53 | 250–251 (AcOEt) |

TABLE 9

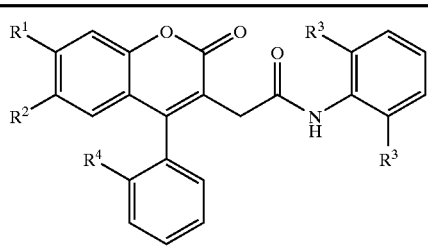

| Example number | R¹ | R² | R³ | R⁴ | Yield (%) | Melting Point (° C.) (Recrystallization solvent) |
|---|---|---|---|---|---|---|
| 27 | Me | Me | OMe | H | 75 | 236–237 (AcOEt) |
| 28 | Me | Me | OMe | Me | 74 | 166–167 (AcOEt) |
| 29 | Me | Me | OEt | H | 75 | 230–231 (AcOEt) |
| 30 | Me | Me | Et | H | 74 | 259–260 (AcOEt) |
| 31 | Me | Me | CH(CH₃)₂ | H | 74 | 252–253 (AcOEt) |
| 32 | (CH₂)₄ | | OMe | H | 63 | 227–228 (AcOEt) |
| 33 | (CH₂)₄ | | OEt | H | 60 | 196–197 (AcOEt) |

TABLE 9-continued

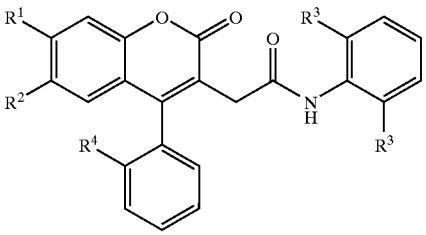

| Example number | R¹ | R² | R³ | R⁴ | Yield (%) | Melting Point (° C.) (Recrystallization solvent) |
|---|---|---|---|---|---|---|
| 34 | (CH₂)₄ | | CH(CH₃)₂ | H | 53 | 235–236 (AcOEt) |
| 35 | (CH₂)₄ | | Et | H | 55 | 240–241 (AcOEt) |

TABLE 10

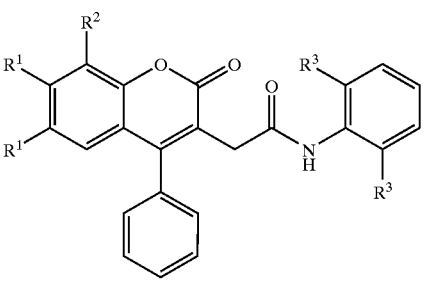

| Example number | R¹ | R² | R³ | Yield (%) | Melting Point (° C.) (Recrystallization solvent) |
|---|---|---|---|---|---|
| 36 | Cl | H | OMe | 48 | 249–250 (AcOEt) |
| 37 | Cl | H | OEt | 55 | 246–247 (AcOEt) |
| 38 | Cl | H | Et | 48 | 296–297 (AcOEt) |
| 39 | Cl | H | CH(CH₃)₂ | 55 | 289–290 (AcOEt) |
| 40 | Cl | Cl | OMe | 83 | 289–291 (THF) |
| 41 | F | H | OMe | 73 | 196–198 (AcOEt–THF) |
| 42 | F | H | CH(CH₃)₂ | 75 | 255–256 (AcOEt–THF) |
| 43 | F | H | OCH(CH₂)₃ | 55 | 249–252 (AcOEt) |
| 44 | F | H | cyclopentyloxy | 38 | 253–254 (AcOEt) |

TABLE 11

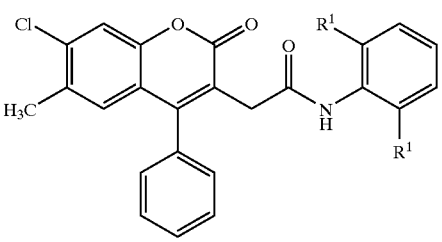

| Example number | R¹ | Yield (%) | Melting Point (° C.) (Recrystallization solvent) |
|---|---|---|---|
| 45 | OMe | 60 | 247–249 (THF) |
| 46 | CH(CH₃)₂ | 42 | 280–282 (THF) |

Example 47–69

The compounds of table 12 were obtained by the method similar to that in Example 15.

TABLE 12

[Structure: coumarin core with R¹, R² substituents on benzene ring, phenyl-R³ group at 4-position, and CH₂-C(=O)-NH-phenyl-R⁴ group at 3-position]

| Example number | R¹ | R² | R³ | R⁴ | Yield (%) | Melting Point (° C.) (Recrystallization solvent) |
|---|---|---|---|---|---|---|
| 47 | F | F | H | 2-CF₃, 4-Cl | 55 | 172–174 (AcOEt) |
| 48 | Cl | Cl | H | 2-CF₃, 4-Cl | 61 | 203–206 (AcOEt) |
| 49 | Me | Cl | H | 2-CF₃, 4-Cl | 74 | 236–239 (AcOEt-IPE) |
| 50 | Me | Cl | H | 2-CF₃, 4-F | 78 | 224–226 (AcOEt-IPE) |
| 51 | Me | Cl | H | 2,4-di-(CF₃) | 51 | 239–240 (AcOEt-IPE) |
| 52 | Me | Cl | H | 2-OCF₃, 4-Cl | 37 | 214–215 (AcOEt-IPE) |
| 53 | Me | Cl | 3-Cl | 2-CF₃, 4-Cl | 51 | 202–204 (AcOEt-IPE) |
| 54 | Me | Me | H | 2-CF₃, 4-Cl | 65 | 201–203 (AcOEt) |
| 55 | Cl | Me | H | 2-CF₃, 4-Cl | 93 | 214–216 (AcOEt) |
| 56 | (CH₂)₃ | | H | 2-CF₃ | 79 | 191–193 (AcOEt) |
| 57 | (CH₂)₃ | | 3-Me | 2-CF₃ | 68 | 205–207 (AcOEt) |
| 58 | (CH₂)₃ | | 3-Me | 2-CF₃, 4-F | 77 | 204–205 (AcOEt) |
| 59 | (CH₂)₃ | | 3-Me | 2-CF₃, 4-Cl | 59 | 182–184 (AcOEt) |
| 60 | (CH₂)₃ | | 4-Me | 2-CF₃ | 64 | 224–226 (AcOEt) |
| 61 | (CH₂)₃ | | 4-Me | 2-CF₃, 4-F | 68 | 234–236 (AcOEt) |
| 62 | (CH₂)₃ | | 4-Me | 2-CF₃, 4-Cl | 61 | 235–236 (AcOEt) |
| 63 | (CH₂)₃ | | 3,5-di-Me | 2-CF₃ | 81 | 264–265 (AcOEt) |
| 64 | (CH₂)₃ | | 3,5-di-Me | 2-CF₃, 4-F | 72 | 226–228 (AcOEt) |
| 65 | (CH₂)₃ | | 3,5-di-Me | 2-CF₃, 4-Cl | 78 | 221–223 (AcOEt) |
| 66 | (CH₂)₃ | | 4-F | 2-CF₃ | 74 | 221–223 (AcOEt) |
| 67 | (CH₂)₃ | | 4-F | 2-CF₃, 4-F | 88 | 234–236 (AcOEt) |
| 68 | (CH₂)₃ | | 4-F | 2-CF₃, 4-Cl | 71 | 232–234 (AcOEt) |
| 69 | Me | Cl | H | 2-CF₃ | 63 | 224–225 (AcOEt-IPE) |

Example 70

Synthesis of 2-[7-chloro-6-{(dimethylamino)methyl}-2-oxo-4-phenyl-2H-chromen-3-yl]-N-(2,6-dimethoxyphenyl)acetamide

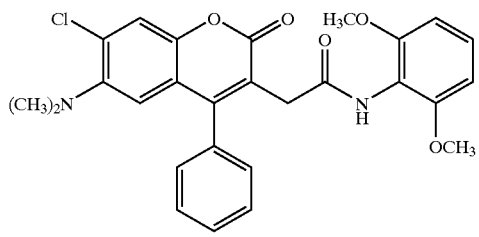

A solution of 2-[6-(bromomethyl)-7-chloro-2-oxo-4-phenyl-2H-chromen-3-yl]acetic acid (0.13 g) in THF (3 ml) was combined with DMF (1 drop) and oxalyl chloride (56 ml), and stirred at room temperature for 1 hour. The reaction solution was concentrated under reduced pressure, and the resultant residue was dissolved in THF (2 ml), and added dropwise to a solution of 2,6-dimethoxyaniline (46 ml) and triethylamine (86 ml) in THF (2 ml) at 0° C. After stirring for 1 hour, the reaction solution was combined with water, and the solution was extracted with ethyl acetate. The extract was washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. The resultant residue was dissolved in THF (2 ml), combined with a solution of dimethylamine (200 mg) in THF (1 ml), and stirred overnight. The reaction solution was concentrated under reduced pressure, and the resultant residue was dissolved in ethyl acetate (30 ml), and then washed with a saturated aqueous solution of sodium chloride. After drying over magnesium sulfate, the solvent was distilled off under reduced pressure. The resultant residue was purified by a silica gel column chromatography (eluent: chloroform-methanol-aqueous ammonia=30:1:0.1), and further purified by recrystallization from ethyl acetate to obtain the title compound (81 mg, yield: 50%).

Melting point: 221–223° C.

NMR (CDCl₃) δ: 2.17 (6H, s), 3.41 (2H, s), 3.48 (2H, brs), 3.79 (6H, brs), 6.54 (2H, d, J=8 Hz), 7.08 (1H, brs), 7.15 (1H, t, J=8 Hz), 7.35–7.60 (8H, m).

IR(KBr): 1732, 1661, 1560, 1478 cm⁻¹.

Analysis for $C_{28}H_{27}N_2O_5Cl$ Calcd (%): C:66.33 H:5.37 N:5.53 Found (%): C:66.17 H:5.38 N:5.22.

Example 71–73

The compounds of table 13 were obtained by the method similar to that in Example 70.

TABLE 13

(structure shown)

| Example number | R¹ | R² | Yield (%) | Melting Point (° C.) (Recrystallization solvent) |
|---|---|---|---|---|
| 71 | morpholin-4-yl | OMe | 53 | 209–211 (AcOEt) |
| 72 | NMe₂ | CH(CH₃)₂ | 54 | 301–303 (AcOEt) |
| 73 | morpholin-4-yl | CH(CH₃)₂ | 53 | 296–298 (AcOEt) |

Example 74

Synthesis of 2-[7-chloro-6-{(morpholin-4-yl)methyl}-2-oxo-4-phenyl-2H-chromen-3-yl]-N-(4-chloro-2-trifluoromethylphenyl)acetamide

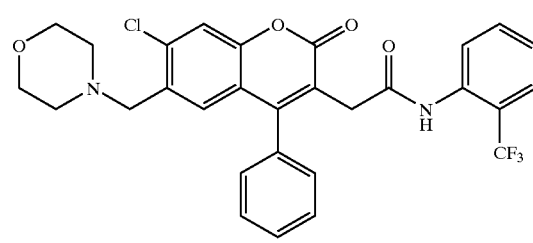

A solution of 2-[6-(bromomethyl)-7-chloro-2-oxo-4-phenyl-2H-chromen-3-yl]acetic acid (0.20 g) in THF (5 ml) was combined with DMF (1 drop) and oxalyl chloride (86 ml), and stirred at room temperature for 1 hour. The reaction solution was concentrated under reduced pressure to obtain the residue, which was dissolved in THF (3 ml), and added dropwise to a suspension of 4-chloro-2-trifluoromethylaniline (69 ml) and sodium hydride (60%, in oil) in THF (2 ml) at 0° C. After stirring at room temperature for 12 hours, the reaction solution was combined with water, and the product was extracted with ethyl acetate. The extract was washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. The resultant residue was dissolved in THF (2 ml), combined with morpholine (0.21 ml), and stirred for 3 days. The reaction solution was concentrated under reduced pressure, and the resultant residue was dissolved in ethyl acetate (30 ml), and then washed with a saturated aqueous solution of sodium chloride. After drying over magnesium sulfate, the solvent was distilled off under reduced pressure. The resultant residue was purified by a silica gel column chromatography (eluent: chloroform-methanol-aqueous ammonia=40:1:0.1), and further purified by recrystallization from ethyl acetate to obtain the title compound (112 mg, yield: 57%).

Melting point: 205–207° C.
NMR (CDCl₃) δ: 2.35–2.45 (4H, m), 3.45–3.65 (8H, m), 7.21 (1H, s), 7.30–7.40 (2H, m), 7.45 (1H, s), 7.45–7.65 (5H, m), 8.08 (1H, d, J=9 Hz), 8.24 (1H, brs).
IR(KBr): 1725, 1663, 1530, 1310 cm⁻¹.
Analysis for $C_{29}H_{23}N_2O_4Cl_2F_3$ Calcd (%): C:58.90 H:3.92 N:4.74 Found (%): C:58.90 H:3.89 N:4.61.

Example 75–79

The compounds of table 14 were obtained by the method similar to that in Example 74.

TABLE 14

(structure shown)

| Example number | R¹ | R² | Yield (%) | Melting Point (° C.) (Recrystallization solvent) |
|---|---|---|---|---|
| 75 | 4-phenyl-1-piperazinyl methyl | Cl | 74 | 201–203 (AcOEt-IPE) |
| 76 | CH₂NMe₂ | H | 35 | 176–178 (AcOEt-IPE) |
| 77 | morpholin-4-ylmethyl | H | 36 | 171–172 (AcOE-IPE) |
| 78 | Cl | CH₂NMe₂ | 95 | 215–217 (AcOEt-IPE) |
| 79 | Cl | morpholin-4-ylmethtyl | 69 | 216–218 (AcOEt-IPE) |

Example 80

Synthesis of [7-chloro-3-{2-(2,6-dimethoxyanilino)-2-oxoethyl}-2-oxo-4-phenyl-2H-chromen-6-yl]methyl acetate

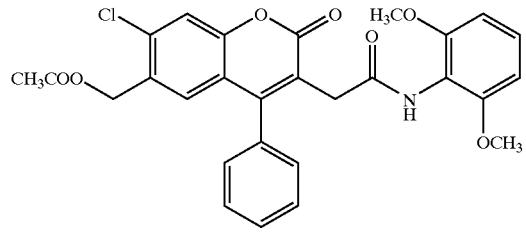

A solution of 2-[6-(bromomethyl)-7-chloro-2-oxo-4-phenyl-2H-chromen-3-yl]acetic acid (0.13 g) in THF (3 ml) was combined with DMF (1 drop) and oxalyl chloride (56 ml), and stirred at room temperature for 1 hour. The reaction solution was concentrated under reduced pressure, and the resultant residue was dissolved in THF (2 ml), and added dropwise to a solution of 2,6-dimethoxyaniline (46 ml) and triethylamine (86 ml) in THF (2 ml) at 0° C. After stirring for 1 hour, the reaction solution was combined with water, and the product was extracted with ethyl acetate. The extract was washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. The resultant residue was dissolved in DMF (2 ml), combined with anhydrous sodium acetate (150 mg), and stirred at 60° C. for 3 hours. The reaction solution was combined with water, and the product was extracted with ethyl acetate, and the extract was washed with a saturated aqueous solution of sodium chloride. After drying over magnesium sulfate, the solvent was distilled off under reduced pressure, and the resultant residue was purified by recrystallization from THF to obtain the title compound (61 mg, yield: 36%).

Melting point: 229–231° C.

NMR (CDCl₃) δ: 1.99 (3H, s), 3.50 (2H, brs), 3.78 (6H, brs), 5.09 (2H, s), 6.55 (2H, d, J=8 Hz), 7.06 (1H, brs), 7.16 (1H, t, J=8 Hz), 7.25–7.60 (8H, m).

IR(KBr): 1737, 1732, 1477, 1260 cm⁻¹.

Analysis for $C_{28}H_{24}NO_7Cl$ Calcd (%): C:64.43 H:4.63 N:2.68 Found (%): C:64.45 H:4.95 N:2.64.

Example 81

Synthesis of [7-chloro-3-{2-(2,6-isopropylanilino)-2-oxoethyl}-2-oxo-4-phenyl-2H-chromen-6-yl]]methyl acetate

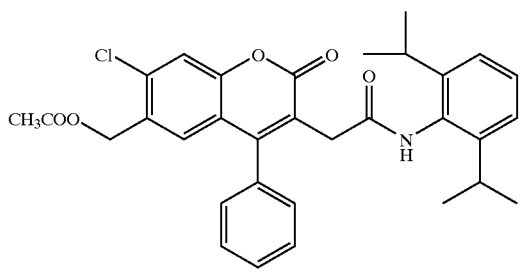

The title compound (yield: 27%) was obtained by the method similar to that in Example 80.

Melting point: 290–292° C.

NMR (CDCl₃) δ: 1.15 (12H, d, J=7 Hz), 1.99 (3H, s), 3.03 (2H, m), 3.53 (2H, s), 5.10 (2H, s), 7.00–7.60 (1H, m).

IR(KBr): 1732, 1647, 1532, 1364 cm⁻¹.

Analysis for $C_{32}H_{32}NO_5Cl$ Calcd (%): C:70.39 H:5.91 N:2.57 Found (%): C:70.41 H:5.67 N:2.58.

Example 82

Synthesis of [7-chloro-3-{2-(4-chloro-2-trifluoromethylanilino)-2-oxoethyl}-2-oxo-4-phenyl-2H-chromen-6-yl]methyl acetate

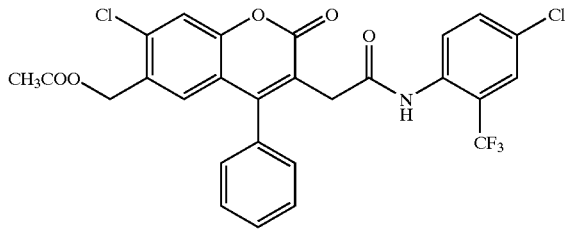

A solution of 2-[6-(bromomethyl)-7-chloro-2-oxo-4-phenyl-2H-chromen-3-yl]acetic acid (0.30 g) in THF (6 ml) was combined with DMF (1 drop) and oxalyl chloride (130 ml), and stirred at room temperature for 1 hour. The reaction solution was concentrated under reduced pressure to obtain the residue, which was dissolved in THF (3 ml), and added dropwise to a suspension of 4-chloro-2-fluoromethylaniline (104 ml) and sodium hydride (60%, in oil)(121 mg) in THF (2 ml) at 0° C. After stirring for 1 hour, the reaction solution was combined with water, and the product was extracted with ethyl acetate. The extract was washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. The resultant residue was dissolved in DMF (3 ml), combined with anhydrous sodium acetate (121 mg), and stirred at 60° C. for 3 hours. The reaction solution was combined with water, and the product was extracted with ethyl acetate, and the extract was washed with a saturated aqueous solution of sodium chloride. After drying over magnesium sulfate, the solvent was distilled off under reduced pressure to obtain the residue, which was purified by a silica gel column chromatography (eluent: ethyl acetate-hexane=1:2), and further purified by recrystallization from ethyl acetate to obtain the title compound (126 mg, yield: 45%).

Melting point: 186–187° C.

NMR (CDCl₃) δ: 1.99 (3H, s), 3.49 (2H, s), 5.10 (2H, s), 7.08 (1H, s), 7.30–7.40 (2H, m), 7.45–7.65 (6H, m), 8.08 (1H, d, J=9 Hz), 8.17 (1H, brs).

IR(KBr): 1725, 1663, 1530, 1310 cm⁻¹.

Analysis for $C_{27}H_{18}NO_5Cl_2F_3$ Calcd (%): C:57.46 H:3.21 N:2.48 Found (%): C:57.20 H:3.25 N:2.25

Example 83–84

The compounds of table 15 were obtained by the method similar to that in Example 82.

TABLE 15

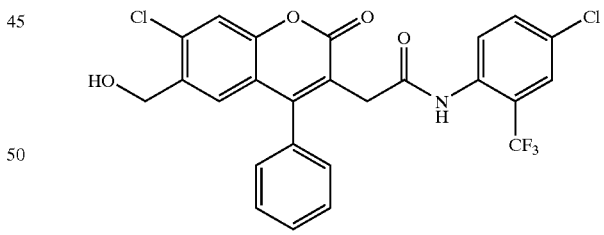

| Example number | R¹ | R² | Yield (%) | Melting Point (° C.) (Recrystallization solvent) |
|---|---|---|---|---|
| 83 | CH₂OAc | H | 35 | 184–185 (AcOEt) |
| 84 | Cl | CH₂OAc | 56 | 237–238 (AcOEt-IPE) |

Example 85

Synthesis of 2-[7-chloro-6-{(hydroxylmethyl)-2-oxo-4-phenyl-2H-chromen-3-yl)-N-(4-chloro-2-trifluoromethylphenyl)acetamide

[7-chloro-3-{2-(4-chloro-2-trifluoromethylanilino)-2-oxoethyl)-2-oxo-4-phenyl-2H-chromen-6-yl) methyl acetate ester (81 mg) was dissolved in a solvent mixture of THF (4 ml) and methanol (2 ml), combined with DBU (0.11 ml), and stirred at room temperature for 30 minutes. The reaction solution was diluted with ethyl acetate (30 ml), and then washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. The resultant residue was purified by a silica gel column chromatography (eluent: ethyl acetate), and further purified by recrystallization from ethyl acetate to obtain the title compound (34 mg, yield: 80%).

Melting point: 241–243° C.

NMR (CDCl$_3$) δ: 1.85 (1H, t, J=6 Hz), 3.48 (2H, s), 4.70 (2H, d, J=6 Hz), 7.21 (1H, s), 7.30–7.40 (2H, m), 7.45–7.65 (6H, m), 8.08 (1H, d, J=9 Hz), 8.19 (1H, brs).

IR(KBr): 1699, 1655, 1306, 1144 cm$^{-1}$.

Analysis for C$_{25}$H$_{16}$NO$_4$Cl$_2$F$_3$ Calcd (%): C:57.49H:3.09 N:2.68 Found (%): C:57.52H:3.09 N:2.57.

Example 86–87

The compounds of table 16 were obtained by the method similar to that in Example 85.

TABLE 16

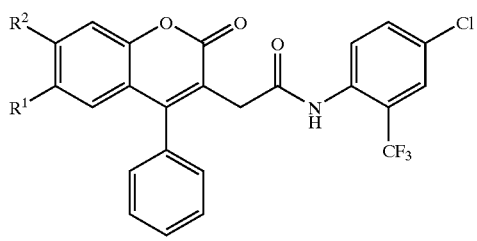

| Example number | R$^1$ | R$^2$ | Yield (%) | Melting Point (° C.) (Recrystallization solvent) |
|---|---|---|---|---|
| 86 | CH$_2$OH | H | 37 | 226–227 (AcOEt) |
| 87 | Cl | CH$_2$OH | 46 | 220–222 (AcOEt-IPE) |

Example 88–89

The compounds of table 17 were obtained by the method similar to that in Example 15.

TABLE 17

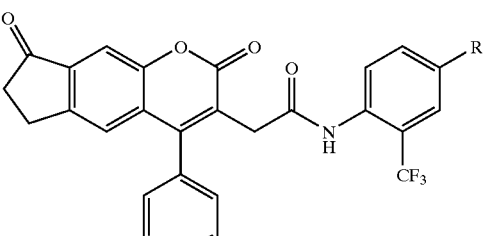

| Example number | R | Yield (%) | Melting Point (° C.) (Recrystallization solvent) |
|---|---|---|---|
| 88 | F | 52 | 180–183 (AcOEt) |
| 89 | Cl | 33 | 189–192 (THF-IPE) |

Reference Example 29–31

The compounds of table 18 were obtained by the method similar to that in Reference Example 7.

TABLE 18

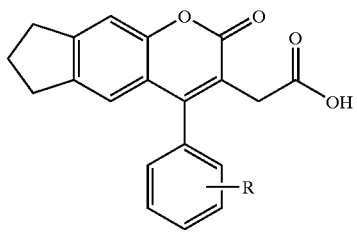

| Ref.Ex. number | R | Yield (%) | Melting Point (° C.) (Recrystallization solvent) |
|---|---|---|---|
| 29 | 3-CF$_3$ | 82 | 159–161 (Et$_2$O-hexane) |
| 30 | 4-CF$_3$ | 82 | 202–204 (IPE) |
| 31 | 3,5-di-(CF$_3$) | 75 | 193-195 (IPE-hexane) |

Reference Example 32–34

The compounds of table 19 were obtained by the method similar to that in Reference Example 27.

TABLE 19

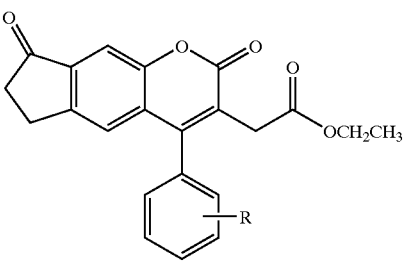

| Ref.Ex. number | R | Yield (%) | Melting Point (° C.) (Recrystallization solvent) |
|---|---|---|---|
| 32 | 3,5-di-Me | 16 | 174–276 (AcOEt) |
| 33 | 3-Me | 12 | 182–184 (AcOEt) |
| 34 | 3-CF$_3$ | 22 | 142–143 (Et$_2$O-hexane) |

Reference Example 35–37

The compounds of table 20 were obtained by the method similar to that in Reference Example 28.

TABLE 20

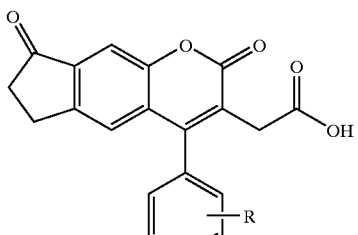

| Ref. Ex. number | R | Yield (%) | Melting Point (° C.) (Recrystallization solvent) |
|---|---|---|---|
| 35 | 3,5-di-Me | 70 | 187–190 (AcOEt) |
| 36 | 3-Me | 89 | 247 (decomp.) (AcOEt) |
| 37 | 3-CF$_3$ | 90 | 200–202 (Et$_2$O-IPE) |

Example 90–95

The compounds of table 21 were obtained by the method similar to that in Example 15.

TABLE 21

| Example number | R¹ | R² | Yield (%) | Melting Point (° C.) (Recrystallization solvent) |
|---|---|---|---|---|
| 90 | F  | 3-CF₃ | 58 | 213–214 (AcOEt-IPE) |
| 91 | Cl | 3-CF₃ | 70 | 206–207 (THF-IPE) |
| 92 | F  | 4-CF₃ | 78 | 250–252 (THF-IPE) |
| 93 | Cl | 4-CF₃ | 55 | 249–250 (AcOEt) |
| 94 | F  | 3,5-di-(CF₃) | 58 | 278–280 (THF-IPE) |
| 95 | Cl | 3,5-di-(CF₃) | 70 | 254–256 (THF-IPE) |

Example 96–101

The compounds of table 22 were obtained by the method similar to that in Example 15.

TABLE 22

| Example number | R¹ | R² | Yield (%) | Melting Point (° C.) (Recrystallization solvent) |
|---|---|---|---|---|
| 96  | F  | 3,5-di-Me | 19 | 274–276 (AcOEt-IPE) |
| 97  | Cl | 3,5-di-Me | 12 | 274–276 (THF-IPE) |
| 98  | F  | 3-Me | 49 | 216–217 (AcOEt) |
| 99  | Cl | 3-Me | 60 | 225–227 (AcOEt-IPE) |
| 100 | F  | 3-CF₃ | 19 | 227–229 (AcOEt-IPE) |
| 101 | Cl | 3-CF₃ | 43 | 122–123 (AcOEt-hexane) |

Reference Example 38

Synthesis of 3-(2-methylphenyl)-6,7-dihydro-5H-indeno[5,6-b]furan-2-carboxylic acid

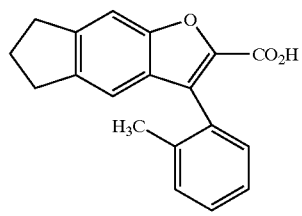

A solution of (6-hydroxy-2,3-dihydro-1H-inden-5-yl)(2-methylphenyl)methanone (2.0 g) in DMF (50 ml) was combined with sodium hydride (60%, in oil) (400 mg) with cooling in ice. After stirring at the same temperature for 30 minutes, the mixture was combined with ethyl bromoacetate (1 ml), and stirred for 1 hour. The reaction solution was combined with water and extracted with ethyl acetate. The extract was washed with water, and then dried over magnesium sulfate, and the solvent was distilled off under reduced pressure. The resultant residue was dissolved in toluene (50 ml), and combined with DBU (2 ml). The reaction solution was heated under reflux overnight, and then combined with water, and extracted with ethyl acetate. The extract was washed with water, and then dried over magnesium sulfate, and the solvent was distilled off under reduced pressure. The resultant residue was purified by a column chromatography (packing: silica gel, eluent: ethyl acetate-hexane=1:3) to obtain a crude product of ethyl 3-(2-methylphenyl)-6,7-dihydro-5H-indeno[5,6-b]furan-2-carboxylate. The resultant crude product of ester was dissolved in a solvent mixture of THF (50 ml) and methanol (30 ml), combined with a 1 N solution of sodium hydroxide (30 ml), and stirred at room temperature for 3 hours. The reaction solution was concentrated under reduced pressure, and the resultant residue was combined with water and extracted with ethyl acetate after acidifying with diluted hydrochloric acid. The extract was washed with water, and then dried over magnesium, and the solvent was distilled off under reduced pressure. The resultant residue was purified by recrystallization from ethyl acetate to obtain the title compound (0.9 g, yield: 39%) as a colorless crystal.

Melting point: 213–215° C.

NMR (CDCl₃) δ: 2.13 (2H, m), 2.17 (3H, m), 2.91 (2H, t, J=8 Hz), 3.04 (2H, t, J=8 Hz), 7.11 (1H, s), 7.26 (2H, m), 7.32 (2H, m), 7.45 (1H, s).

IR(KBr): 3400–2400, 1720 cm⁻¹.

Analysis for $C_{19}H_{16}O_3$

Calcd (%): C:78.06H:5.52

Found (%): C:77.82H:5.59.

Reference Example 39–53

The compounds of table 23 and table 24 were obtained by the method similar to that in Reference Example 38.

TABLE 23

| Ref.Ex. number | R | Yield (%) | Melting Point (° C.) (Recrystallization solvent) |
|---|---|---|---|
| 39 | 3-Me | 72 | 240–244 (AcOEt) |
| 40 | 4-Me | 76 | 240–244 (AcOEt) |

TABLE 23-continued

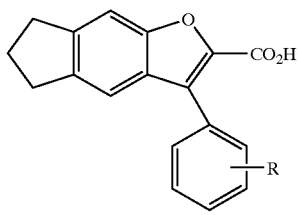

| Ref.Ex. number | R | Yield (%) | Melting Point (° C.) (Recrystallization solvent) |
|---|---|---|---|
| 41 | H | 63 | 230–231 (AcOEt) |
| 42 | 4-F | 48 | 215–218 (AcOEt) |
| 43 | 4-OMe | 85 | 240–243 (AcOEt) |

TABLE 24

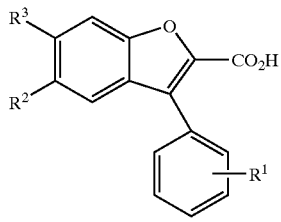

| Ref. Ex. number | $R^1$ | $R^2$ | $R^3$ | Yield (%) | Melting Point (° C.) (Recrystallization solvent) |
|---|---|---|---|---|---|
| 44 | 2-Me | Cl | Me | 53 | 224–225 (AcOEt) |
| 45 | H | Me | Me | 46 | 268–269 (AcOEt) |
| 46 | 2-Me | Me | Me | 39 | 218–219 (AcOEt) |
| 47 | 3-Me | Me | Me | 62 | 224–226 (AcOEt) |
| 48 | 2-Me | Me | Cl | 78 | 190–220 (AcOEt) |
| 49 | 3-Me | Me | Cl | 33 | 210–213 (AcOEt) |
| 50 | 2-Me | Cl | Cl | 62 | 193–195 (AcOEt-hexane) |
| 51 | 2-Me | F | F | 40 | 206–208 (AcOEt) |
| 52 | 2-Me | $(CH_2)_4$ | | 86 | Amorphous |
| 53 | 3-Me | $(CH_2)_4$ | | 34 | 228–230 (AcOEt) |

Example 102
N-(2,6-Dimethoxyphenyl)-N'-[3-(2-methylphenyl)-6,7-dihydro-5H-indeno[5,6-b]furan-2-yl]urea

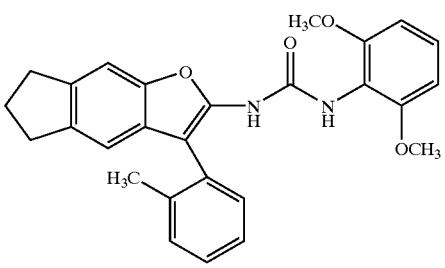

A solution of 3-(2-methylphenyl)-6,7-dihydro-5H-indeno[5,6-b]furan-2-carboxylic acid (3 g), triethylamine (2.2 ml) and DPPA (2.9 ml) in benzene (200 ml) was stirred at room temperature for 1 hour, and then heated under reflux for 1 hour. After cooling to room temperature, to the reaction solution 2,6-dimethoxyaniline (1.6 g) was added and then heated under reflux for 1 hour. The reaction solution was combined with water and chloroform, and the organic layer was washed with diluted hydrochloric acid followed by a saturated aqueous solution of sodium hydrogen carbonate and water, and after drying over magnesium sulfate, the solvent was distilled off under reduced pressure. The resultant residue was purified by a silica gel column chromatography (eluent: chloroform), and further purified by recrystallization from THF-chloroform to obtain the title compound as a colorless crystal (2.4 g, 53%).

Melting point: 270° C. (decomp.).

NMR (CDCl$_3$) δ: 2.11 (2H, m), 2.27 (3H, m), 2.90 (2H, t, J=7 Hz), 2.99 (2H, t, J=7 Hz), 3.71 (6H, s), 6.54 (1H, s), 6.56 (2H, d, J=8 Hz), 6.86 (1 h, bs), 7.06 (1H, s), 7.15 (1H, t, J=8 Hz), 7.33 (5H, m).

IR(KBr): 3241, 1659, 1557 cm$^{-1}$.

Analysis for $C_{27}H_{26}N_2O_4$ Calcd (%): C:78.28 H:5.92 N:6.33 Found (%): C:73.15 H:6.00 N:6.29.

Example 102–103

The compounds of table 25 and table 26 were obtained by the method similar to that in Example 101.

TABLE 25

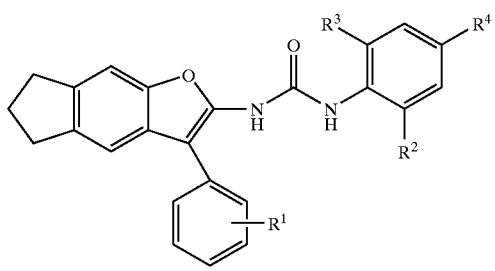

| Example number | $R^1$ | $R^2$ | $R^3$ | $R^4$ | Yield (%) | Melting Point (° C.) (Recrystallization solvent) |
|---|---|---|---|---|---|---|
| 102 | 3-Me | OMe | OMe | H | 19 | 208 (decomp.) (AcOEt) |
| 103 | 4-Me | OMe | OMe | H | 53 | 236 (decomp.) (AcOEt) |
| 104 | H | OMe | OMe | H | 50 | 238–241 (AcOEt) |
| 105 | 2-Me | Et | Et | H | 28 | 250 (decomp.) (AcOEt) |

TABLE 25-continued

| Example number | R¹ | R² | R³ | R⁴ | Yield (%) | Melting Point (° C.) (Recrystallization solvent) |
|---|---|---|---|---|---|---|
| 106 | 3-Me | Et | Et | H | 23 | 225–228 (AcOEt) |
| 107 | 4-Me | Et | Et | H | 26 | 250–254 (AcOEt) |
| 108 | H | Et | Et | H | 42 | 248–251 (AcOEt) |
| 109 | 2-Me | OEt | OEt | H | 45 | 227 (decomp.) (AcOEt) |
| 110 | 3-Me | OEt | OEt | H | 14 | 210–212 (AcOEt) |
| 111 | H | OEt | OEt | H | 45 | 210–212 (AcOEt) |
| 112 | 2-Me | CH(CH₃)₂ | CH(CH₃)₂ | H | 33 | 238 (decomp.) (AcOEt) |
| 113 | 3-Me | CH(CH₃)₂ | CH(CH₃)₂ | H | 34 | 235 (decomp.) (AcOEt) |
| 114 | 3-Me | OMe | Me | H | 19 | 208 (decomp.) (AcOEt) |
| 115 | 2-Me | OMe | OMe | Me | 69 | 280 (decomp.) (AcOEt-hex) |
| 116 | 2-Me | OMe | OH | H | 78 | 210–212 (THF) |
| 117 | 2-Me | OMe | OMe | OH | 27 | 224–227 (AcOEt) |
| 118 | 2-Me | OMe | OH | OMe | 36 | 218–221 (AcOEt) |
| 119 | 2-Me | OMe | OMe | F | 45 | 280 (decomp.) (CH₂Cl₂) |
| 120 | 4-F | OMe | OMe | H | 36 | 246 (decomp.) (AcOEt) |
| 121 | 4-OMe | OMe | OMe | H | 58 | 238 (decomp.) (AcOEt) |

TABLE 26

| Example number | R¹ | R² | R³ | R⁴ | Yield (%) | Melting Point (° C.) (Recrystallization solvent) |
|---|---|---|---|---|---|---|
| 122 | 2-Me | Cl | Me | OMe | 35 | 282 (decomp.) (THF) |
| 123 | H | Me | Me | OMe | 28 | 252 (decomp.) (THF) |
| 124 | 2-Me | Me | Me | OMe | 39 | 238 (decomp.) (AcOEt) |
| 125 | 3-Me | Me | Me | OMe | 47 | 230 (decomp.) (AcOEt) |
| 126 | 2-Me | Me | Cl | OMe | 34 | 242 (decomp.) (AcOEt) |
| 127 | 3-Me | Me | Cl | OMe | 34 | 238 (decomp.) (AcOEt) |
| 128 | 3-Me | Me | Cl | Et | 23 | 235–239 (AcOEt) |
| 129 | 2-Me | Cl | Cl | OMe | 17 | 275–277 (THF) |
| 130 | 2-Me | F | F | OMe | 26 | 194–196 (THF) |
| 131 | 2-Me | (CH₂)₄ | | OMe | 26 | 195 (decomp.) (AcOEt) |
| 132 | 3-Me | (CH₂)₄ | | OMe | 47 | 215 (decomp.) (AcOEt) |
| 133 | 3-Me | (CH₂)₄ | | Et | 32 | 235 (decomp.) (AcOEt) |

TABLE 27

| Ref.Ex. number | R¹ | R² | R³ | Yield (%) | Melting Point (° C.) (Recrystallization solvent) |
|---|---|---|---|---|---|
| 54 | (CH₂)₄ | | 3-Me | 89 | 203–206 (AcOEt-IPE) |
| 55 | Me | Cl | 3-Cl | 58 | 262–264 (AcOEt-IPE) |
| 56 | (CH₂)₃ | | 3-Cl | 63 | 210–213 (AcOEt-IPE) |
| 57 | (CH₂)₄ | | 3-Cl | 73 | 233–238 (AcOEt-IPE) |
| 58 | Me | Cl | 4-CF₃ | 96 | 231–234 (AcOEt-hexane) |
| 59 | (CH₂)₃ | | 3,4-Me₂ | 87 | 189–191 (AcOEt) |
| 60 | (CH₂)₃ | | 3-Cl, 4-F | 97 | 243–244 (AcOEt) |
| 61 | Me | Cl | 3,4-Me₂ | 86 | 225–227 (AcOEt) |
| 62 | Br | Me | H | 82 | 256–257 (THF) |
| 63 | OMe | Cl | H | 61 | 254–257 (AcOH-H₂O) |

Reference Example 54–63

Reference Example 64–65

The compounds of table 27 were obtained by the method similar to that in Reference Example 13.

The compounds of table 28 were obtained by the method similar to that in Reference Example 27.

TABLE 28

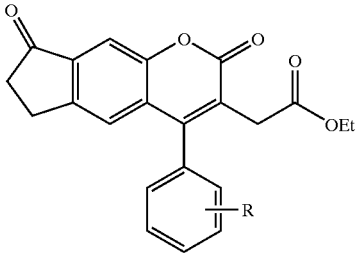

| Ref.Ex. number | R | Yield (%) | Melting Point (° C.) (Recrystallization solvent) |
|---|---|---|---|
| 64 | 3-Cl | 82 | 164–165 (AcOEt) |
| 65 | 4-$CF_3$ | 37 | 134–135 ($Et_2$O-hexane) |

Reference Example 66–67

The compounds of table 29 were obtained by the method similar to that in Reference Example 28.

TABLE 29

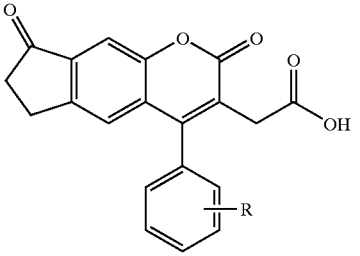

| Ref.Ex. number | R | Yield (%) | Melting Point (° C.) (Recrystallization solvent) |
|---|---|---|---|
| 66 | 3-Cl | 89 | 173 (decomp.) (AcOEt) |
| 67 | 4-$CF_3$ | 84 | 245 (decomp.) ($Et_2$O-IPE) |

Example 134–153

The compounds of table 30 were obtained by the method similar to that in Example 1.

TABLE 30

| Example number | $R^1$ | $R^2$ | $R^3$ | $R^4$ | Yield (%) | Melting Point (° C.) (Recrystallization solvent) |
|---|---|---|---|---|---|---|
| 134 | $(CH_2)_2CO$ | | 3-Cl | 2,6-(i-Pr)$_2$ | 11 | 232–234 (THF-AcOEt) |
| 135 | $(CH_2)_2CO$ | | 3-Me | 2,6-(i-Pr)$_2$ | 4 | 203–206 (THF-AcOEt) |
| 136 | $CO(CH_2)_2$ | | 3-Cl | 2,6-(OMe)$_2$ | 46 | 268–271 (THF-AcOEt) |
| 137 | Me | Cl | 3-Cl | 2,6-Me$_2$, 4-Cl | 16 | 292–295 (THF-IPE) |
| 138 | Me | Cl | 3-Cl | 2-Me, 4-Cl | 42 | 247–249 (AcOEt-IPE) |
| 139 | Me | Cl | 3-Cl | 2-Me, 4-F | 74 | 242–245 (AcOEt-IPE) |
| 140 | Me | Cl | 3-Cl | 2-$CH_2$OH, 4-Cl | 41 | 150 (decomp.) (THF-AcOEt) |
| 141 | Me | Cl | 3-Cl | 2-$CH_2$OMe, 4-Cl | 34 | 180–184 (AcOEt-IPE) |
| 142 | Me | Cl | 3-Cl | 2-$CH_2OC_2H_4$OMe, 4-Cl | 48 | 126–128 (AcOEt-IPE) |
| 143 | Me | Cl | 3-Cl | 2-Me | 79 | 239–240 (AcOEt-IPE) |
| 144 | Me | Cl | 3-Cl | 2-Et | 80 | 201–203 (AcOEt-IPE) |
| 145 | Me | Cl | 3-Cl | 2-iPr | 64 | 205–207 (AcOEt-IPE) |
| 146 | Me | Cl | 3-Cl | 2-Et, 4-Cl | 66 | 228–231 (THF-AcOEt) |
| 147 | Me | Cl | 3-Cl | 2-Et, 4-F | 37 | 226–227 (THE-AcOEt) |
| 148 | Me | Cl | 3-Cl | 2,3-Me$_2$ | 56 | 250–251 (THF-AcOEt) |
| 149 | Me | Cl | 3-Cl | 2,4-Me$_2$ | 69 | 220–222 (AcOEt-IPE) |
| 150 | Me | Cl | 3-Cl | 2,5-Me$_2$ | 59 | 224–226 (AcOEt-IPE) |
| 151 | Me | Cl | 3-Cl | 2,3-($CH_2$)4 | 48 | 242–247 (AcOEt-IPE) |
| 152 | Me | Cl | 3-Cl | 2,4-Cl$_2$ | 54 | 207–210 (AcOEt-IPE) |
| 153 | Me | Cl | 3-Cl | 2-Cl, 4-F | 44 | 211–213 (AcOEt-IPE) |

Example 154–179

The compounds of table 31 were obtained by the method similar to that in Example 15.

TABLE 31

[Chemical structure: coumarin core with R¹ and R² on the benzo ring, a phenyl substituent with R³ at the 4-position, and a CH₂C(O)NH-phenyl-R⁴ group at the 3-position]

| Example number | R¹ | R² | R³ | R⁴ | Yield (%) | Melting Point (° C.) (Recrystallization solvent) |
|---|---|---|---|---|---|---|
| 154 | (CH$_2$)$_2$CO | | 3-Cl | 2-CF$_3$, 4-Cl | 31 | 180 (decomp.) (AcOEt) |
| 155 | (CH$_2$)$_2$CO | | 3-Cl | 2-CF$_3$, 4-F | 27 | 150 (decomp.) (AcOEt) |
| 156 | CO(CH$_2$)$_2$ | | 4-CF$_3$ | 2-CF$_3$, 4-F | 34 | 146–148 (THF-IPE) |
| 157 | CO(CH$_2$)$_2$ | | H | 2-CF$_3$, 4-Cl | 32 | 257–260 (THF-AcOEt) |
| 158 | CO(CH$_2$)$_2$ | | H | 2-CF$_3$, 4-F | 51 | 257–259 (THF-AcOEt) |
| 159 | (CH$_2$)$_4$ | | H | 2-CF$_3$, 4-Cl | 85 | 232–234 (THF-AcOEt) |
| 160 | (CH$_2$)$_4$ | | H | 2-CF$_3$, 4-F | 47 | 231–232 (AcOEt) |
| 161 | (CH$_2$)$_3$ | | 3,4-Me$_2$ | 2-CF$_3$, 4-Cl | 83 | 236–238 (AcOEt) |
| 162 | (CH$_2$)$_3$ | | 3,4-Me$_2$ | 2-CF$_3$, 4-F | 71 | 253–254 (AcOEt) |
| 163 | (CH$_2$)$_3$ | | 3-Cl, 4-F | 2-CF$_3$, 4-Cl | 85 | 221–223 (AcOEt) |
| 164 | (CH$_2$)$_3$ | | 3-Cl, 4-F | 2-CF$_3$, 4-F | 57 | 219–222 (AcOEt) |
| 165 | (CH$_2$)$_4$ | | 3-Me | 2-CF$_3$, 4-Cl | 42 | 192–196 (AcOEt-IPE) |
| 166 | (CH$_2$)$_4$ | | 3-Me | 2-CF$_3$, 4-F | 60 | 215–216 (AcOEt-IPE) |
| 167 | Me | | 3-Cl | 2-CF$_3$, 4-F | 50 | 210–211 (AcOEt-hexane) |
| 168 | (CH$_2$)$_3$ | | 3-Cl | 2-CF$_3$, 4-Cl | 78 | 215–219 (AcOEt-hexane) |
| 169 | (CH$_2$)$_3$ | | 3-Cl | 2-CF$_3$, 4-F | 82 | 219–222 (AcOEt-hexane) |
| 170 | (CH$_2$)$_4$ | | 3-Cl | 2-CF$_3$, 4-Cl | 40 | 214–217 (AcOEt-hexane) |
| 171 | (CH$_2$)$_4$ | | 3-Cl | 2-CF$_3$, 4-F | 45 | 220–224 (AcOEt-hexane) |
| 172 | Me | Cl | 4-CF$_3$ | 2-CF$_3$, 4-Cl | 71 | 261–264 (AcOEt-IPE) |
| 173 | Me | Cl | 4-CF$_3$ | 2-CF$_3$, 4-F | 67 | 250–252 (AcOEt-IPE) |
| 174 | Me | Cl | 3,4-Me$_2$ | 2-CF$_3$, 4-Cl | 67 | 253–254 (THF-IPE) |
| 175 | Me | Cl | 3,4-Me$_2$ | 2-CF$_3$, 4-F | 67 | 240–241 (THF-IPE) |
| 176 | Br | Me | H | 2-CF$_3$, 4-Cl | 58 | 223–225 (AcOEt) |
| 177 | Br | Me | H | 2-CF$_3$, 4-F | 56 | 237–238 (AcOEt) |
| 178 | OMe | Cl | H | 2-CF$_3$, 4-Cl | 81 | 246–247 (THF-EtOH) |
| 179 | OMe | Cl | H | 2-CF$_3$, 4-F | 52 | 218–220 (THF-EtOH) |

Example 180–202

The compounds of table 32 and table 33 were obtained by the method similar to that in Example 74.

TABLE 32

[Chemical structure: 7-Cl coumarin with R¹ at 6-position, 4-phenyl, and CH₂C(O)NH-phenyl(R²,R³) at 3-position]

| Example number | R¹ | R² | R³ | Yield (%) | Melting Point (° C.) (Recrystallization solvent) |
|---|---|---|---|---|---|
| 180 | NHMe | CF$_3$ | Cl | 65 | 205–207 (AcOEt) |
| 181 | NH(CH$_2$)$_3$O(CH$_2$)$_3$CH$_3$ | CF$_3$ | Cl | | 104–106 (ACOEt-hexane) |
| 182 | NEt$_2$ | CF$_3$ | Cl | 87 | 163–164 (AcOEt-IPE) |

TABLE 32-continued

| Example number | R¹ | R² | R³ | Yield (%) | Melting Point (° C.) (Recrystallization solvent) |
|---|---|---|---|---|---|
| 183 | —N(piperazine)N—Me | CF₃ | Cl | 58 | 159 (AcOEt-IPE) |
| 184 | —N(piperazine)N—SO₂Me | CF₃ | Cl | 73 | 205–208 (AcOEt-IPE) |
| 185 | —N(piperazine)N—CH₂Ph | CF₃ | Cl | 49 | 158–160 (AcOEt-IPE) |
| 186 | —N(piperazine)N—(CH₂)₂O(CH₂)₂CH₃ | CF₃ | Cl | 50 | 173–175 (AcOEt-IPE) |
| 187 | —N(piperazine)N—(2-Py) | CF₃ | Cl | 96 | 205–207 (AcOEt-IPE) |
| 188 | —N(piperazine)N—C₆H₄—OH | CF₃ | Cl | 77 | 193 (decomp.) (AcOEt-IPE) |
| 189 | —N(piperidine) | CF₃ | Cl | 74 | 191–194 (AcOEt-IPE) |
| 190 | —N(piperidine)—OH | CF₃ | Cl | 86 | 203–207 (AcOEt) |

TABLE 33

| 191 | —N(piperidine)(Ph)(OH) | CF₃ | Cl | 89 | 194–197 (AcOEt-IPE) |

TABLE 33-continued

| No. | R¹ | R² | R³ | Yield (%) | mp (°C) (solvent) |
|---|---|---|---|---|---|
| 192 | N-piperidine-4-Ph | CF₃ | Cl | 73 | 196–197 (AcOEt-IPE) |
| 193 | N-tetrahydropyridine-4-Ph | CF₃ | Cl | 20 | 201–204 (AcOEt-IPE) |
| 194 | N-piperidine-4-(N-piperidinyl) | CF₃ | Cl | 32 | 186–188 (AcOEt) |
| 195 | N(Me)(2-Py) | CF₃ | Cl | 20 | 219–220 (THF-IPE) |
| 196 | NEt₂ | CF₃ | F | 25 | 206–207 (AcOEt-hexane) |
| 197 | morpholino | CF₃ | F | 87 | 200–206 (AcOEt-hexane) |
| 198 | 4-Ph-piperazin-1-yl | CF₃ | F | 83 | 203–204 (AcOEt-hexane) |
| 199 | 4-SO₂Me-piperazin-1-yl | CF₃ | F | 82 | 216–218 (AcOEt-IPE) |
| 200 | N-tetrahydropyridine-4-Ph | CF₃ | F | 84 | 198–200 (AcOEt-EtOH) |
| 201 | N(Me)(2-Py) | CF₃ | F | 32 | 207–208 (THF-TPE) |
| 202 | 4-Ph-piperazin-1-yl | Me | Cl | 22 | 239–241 (THF-IPE) |

Example 203

Synthesis of 2-[7-chloro-2-oxo-4-phenyl-6-[(pyridine-2-ylthio)methyl]-2H-chromen-3-yl]-N-[4-chloro-2-(trifluoromethyl)phenyl]acetamide

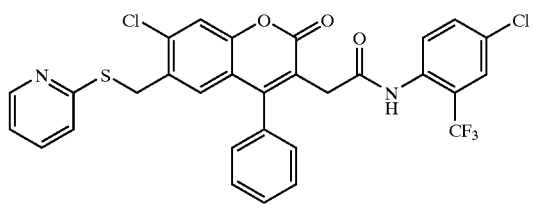

A solution of 2-[6-(bromomethyl)-7-chloro-2-oxo-4-phenyl-2H-chromen-3-yl]acetic acid (0.21 g) in THF (5 ml) was combined with DMF (1 drop) and oxalyl chloride (86 ml), and stirred at room temperature for 1 hour. The reaction solution was concentrated under reduced pressure, and the resultant residue was dissolved in THF (3 ml) and added dropwise to a suspension of 4-chloro-2-trifluoromethylaniline (72 ml) and sodium hydride (60%, in oil) (23 mg) in THF (2 ml) at 0° C. After stirring at room temperature for 12 hours, the reaction solution was combined with water, and the product was extracted with ethyl acetate. The extract was washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. The resultant residue was dissolved in THF (10 ml), combined with 2-mercaptopyridine (0.088 g) and DBU (0.118 ml), and stirred at room temperature for 24 hours. The reaction solution was combined with water, and extracted with ethyl acetate. The extract was washed with a saturated brine, and then dried over magnesium sulfate, and concentrated under reduced pressure. The resultant residue was recrystallized from ethyl acetate-diisopropyl ether to obtain the title compound as a colorless crystal (205 mg, 65%). Melting point: 213–215° C.

Example 204

Synthesis of 2-[7-chloro-2-oxo-4-phenyl-6-[(pyridin-2-ylthio)methyl]-2H-chromen-3-yl]-N-[4-fluoro-2-(trifluoromethyl)phenyl]acetamide

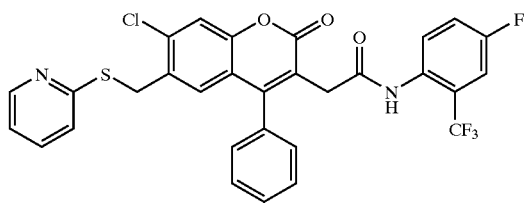

The title compound (yield: 71%) was obtained by the method similar to that in Example 203. Melting Point: 195-196° C. (AcOEt-IPE).

Example 205

Synthesis of 2-[6-[[acetyl(methyl)amino]methyl]-7-chloro-2-oxo-4-phenyl-2H-chromen-3-yl]-N-[4-chloro-2-(trifluoromethyl)phenyl]acetamide

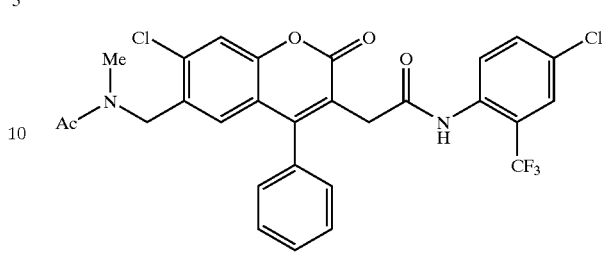

A solution of 2-[6-[(methylamino)methyl]-7-chloro-2-oxo-4-phenyl-2H-chromen-3-yl]-N-[4-chloro-2-(trifluoromethyl)phenyl]acetamide (Example 180)(0.20 g) in THF (5 ml) was combined with triethylamine (0.11 ml) and acetyl chloride (0.033 ml), and stirred for 3 hours. The reaction solution was combined with water and extracted with ethyl acetate. The extract was washed with a saturated aqueous solution of sodium bicarbonate followed by a saturated brine, and then dried over magnesium sulfate, and concentrated under reduced pressure. The resultant residue was purified by column chromatography (packing: silica gel, eluent: ethyl acetate-hexane=1:4), and further recrystallized from ethyl acetate-diisopropyl ether to obtain the title compound as a colorless crystal (105 mg, 48%). Melting point: 199–201° C.

Example 206

Synthesis of 2-[6-[[benzoyl(methyl)amino]methyl]-7-chloro-2-oxo-4-phenyl-2H-chromen-3-yl]-N-[4-chloro-2-(trifluoromethyl)phenyl]acetamide

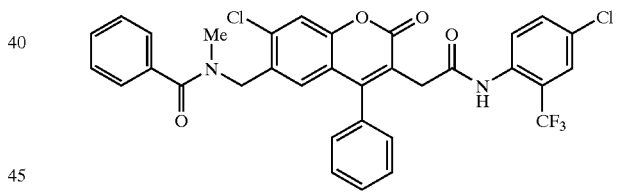

The title compound (yield: 66%) was obtained by the method similar to that in Example 205. Melting Point: 215-216° C. (AcOEt-Hexane).

Example 207

Synthesis of 2-[7-chloro-2-oxo-4-phenyl-6-(piperazin-1-yl)methyl-2H-chromen-3-yl]-N-[4-chloro-2-(trifluoromethyl)phenyl]acetamide

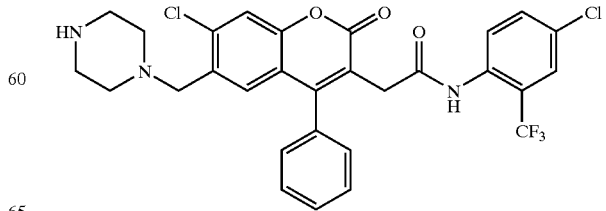

A solution of 2-6-(bromomethyl)-7-chloro-2-oxo-4-phenyl-2H-chromen-3-yl]acetic acid (0.28 g) in THF (7 ml) was combined with DMF (1 drop) and oxalyl chloride (120 ml), and stirred at room temperature for 1 hour. The reaction solution was concentrated under reduced pressure to obtain the residue, which was dissolved in THF (5 ml) and added dropwise to a suspension of 4-chloro-2-trifluoromethylaniline (101 ml) and sodium hydride (60%, in oil) (32 mg) in THF (3 ml) at 0° C. After stirring at room temperature for 12 hours, the reaction solution was combined with water, and the product was extracted with ethyl acetate. The extract was washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. The resultant residue was dissolved in THF (10 ml), combined with tert-butyl 1-piperidinecarboxylate (0.191 g) and triethylamine (0.14 ml), and heated under reflux for 5 hours. The reaction solution was combined with water and extracted with ethyl acetate. The extract was washed with a saturated brine, dried over magnesium sulfate, and then concentrated under reduced pressure. The resultant residue was dissolved in acetic acid (10 ml), combined with concentrated hydrochloric acid (10 ml), and then heated under reflux for 30 minutes. The reaction solution was combined with water and extracted with ethyl acetate. The extract was washed with a saturated sodium bicarbonate followed by a saturated brine, dried over magnesium sulfate, and then the extract was concentrated under reduced pressure. The resultant residue was recrystallized from ethyl acetate-diisopropyl ether to obtain the title compound as a colorless crystal (122 mg, 30%). Melting point: 237–242° C.

Example 208

Synthesis of 2-(7-chloro-6-hydroxy-2-oxo-4-phenyl-2H-chromen-3-yl)-N-[4-chloro-2-(trifluoromethyl)phenyl]acetamide

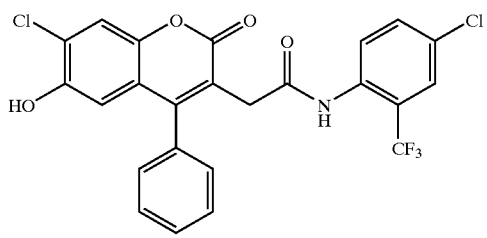

A solution of 2-(7-chloro-6-methoxy-2-oxo-4-phenyl-2H-chromen-3-yl)-N-[4-chloro-2-(trifluoromethyl)phenyl]acetamide (Example 178) (3.20 g) in methylene chloride (10 ml) was combined with a 1 M solution of boron tribromide/methylene chloride (31.6 ml, 13.6 mmol), and stirred at room temperature for 3 days. The reaction solution was poured into an ice water, to which concentrated hydrochloric acid was then added. The precipitate was filtered and washed with isopropanol followed by ether to obtain the title compound as a colorless crystal (2.05 g, 64%). An aliquot was recrystallized from THF-isopropyl ether to measure a melting point. Melting point: 246–247° C.

Example 209

Synthesis of 2-(7-chloro-6-hydroxy-2-oxo-4-phenyl-2H-chromen-3-yl)-N-[4-fluoro-2-(trifluoromethyl)phenyl]acetamide

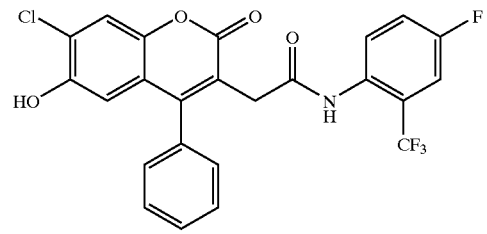

The title compound (yield: 58%) was obtained by the method similar to that in Example 208. Melting Point: 240–243° C. (AcOEt-Hexane).

Example 210

Synthesis of 2-(7-chloro-2-oxo-4-phenyl-6-(2-propoxyethoxy)-2H-chromene-3-yl)-N-[4-chloro-2-(trifluoromethyl)phenyl]acetamide

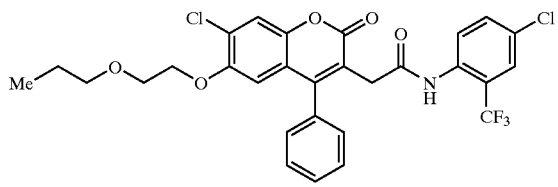

A solution of 2-(7-chloro-6-hydroxy-2-oxo-4-phenyl-2H-chromen-3-yl)-N-[4-chloro-2-(trifluoromethyl)phenyl]acetamide (Example 208) (0.30 g) in DMF (5 ml) was combined with 2-chloroethyl ethyl ether (0.31 ml), potassium carbonate (0.23 g) and sodium iodide (0.15 g), and stirred at 120° C. for 30 minutes. The reaction solution was combined with water and extracted with ethyl acetate. The extract was washed with a saturated brine, and then dried over magnesium sulfate, and concentrated under reduced pressure. The resultant residue was recrystallized from ethyl acetate-diisopropyl ether to obtain the title compound as a colorless crystal (151 mg, 43%). Melting point: 170–171° C.

Example 211–213

The compounds of table 34 were obtained by the method similar to that in Example 210.

TABLE 34

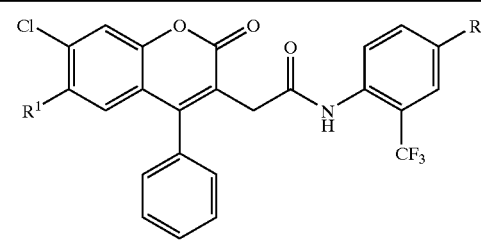

| Example number | $R^1$ | $R^2$ | Yield (%) | Melting Point (° C.) (Recrystallization solvent) |
|---|---|---|---|---|
| 211 | $O(CH_2)_2O(CH_2)_2CH_3$ | F | 32% | 161–162 (AcOEt-IPE) |
| 212 | $O(CH_2)_2OPh$ | Cl | 54% | 176–177 (AcOEt-IPE) |
| 213 | $O(CH_2)_2OPh$ | F | 52% | 189–190 (AcOEt-IPE) |

Example 214

Synthesis of N-[4-fluoro-2-(trifluoromethyl)phenyl]-2-(8-hydroxy-2-oxo-4-phenyl-2,6,7,8-tetrahydrocyclopenta[g]chromen-3-yl)acetamide

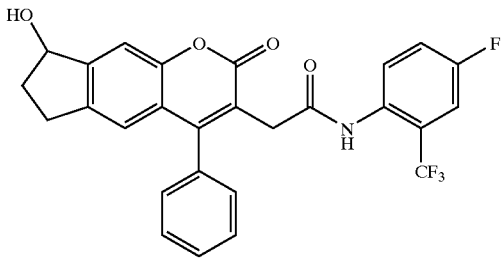

A suspension of NaBH$_4$ (30 mg) in DME (2 ml) was combined with 2-(2,8-dioxo-4-phenyl-2,6,7,8-tetrahydrocyclopenta[g]chromen-3-yl)-N-[4-fluoro-2-(trifluoromethyl)phenyl]-acetamide (Example 88) (170 mg) with cooling in ice, and further combined with methanol, and stirred at room temperature for 10 minutes. The reaction solution was poured into diluted hydrochloric acid, which was then extracted with ethyl acetate. The extract was washed with water, and then dried over magnesium sulfate, and concentrated under reduced pressure to obtain the title compound as a colorless crystal (110 mg, yield: 65%). An aliquot was recrystallized from ethyl acetate to measure a melting point. Melting point: 217–218° C.

Example 215

Synthesis of N-[4-fluoro-2-(trifluoromethyl)phenyl]-2-[8-hydroxy-4-(3-methylphenyl)-2-oxo-2,6,7,8-tetrahydrocyclopenta[g]chromen-3-yl]acetamide

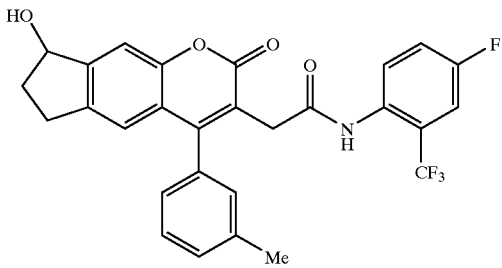

The title compound (yield: 82%) was obtained by the method similar to that in Example 214. Melting Point: 225–227° C. (AcOEt).

Example 216

Synthesis of N-[4-fluoro-2-(trifluoromethyl)phenyl]-2-(4-phenyl-2-oxo-2,6-dihydrocyclopenta[g]chromen-3-yl)acetamide

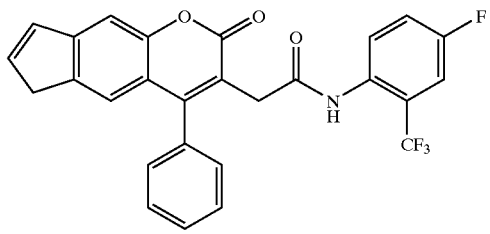

A solution of N-[4-fluoro-2-(trifluoromethyl)phenyl]-2-(8-hydroxy-2-oxo-4-phenyl-2,6,7,8-tetrahydrocyclopenta[g]chromen-3-yl)acetamide (Example 214) (250 mg) in toluene (50 ml) was combined with p-TsOH monohydrate (300 mg), and heated under reflux for 30 minutes. After the reaction solution was concentrated, the resultant residue was purified by a silica gel column chromatography (eluent: hexane-ethyl acetate=3:1) to obtain the title compound as a colorless crystal (200 mg, yield: 74%). An aliquot was recrystallized from THF to measure a melting point. Melting point: 217–218° C.

Example 217

Synthesis of N-[4-fluoro-2-(trifluoromethyl)phenyl]-2-[4-(3-methylphenyl)-2-oxo-2,6-dihydrocyclopenta[g]chromen-3-yl]acetamide

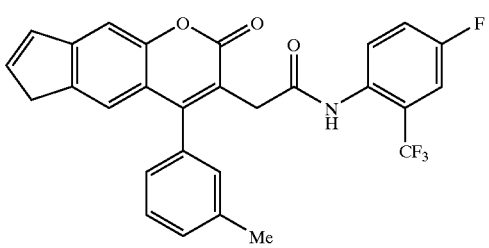

The title compound (yield: 55%) was obtained by the method similar to that in Example 216. Melting Point: 196–197° C. (AcOEt-Hexane).

Example 218

Synthesis of Methyl (2E)-3-[3-[2-[[4-fluoro-2-(trifluoromethyl)phenyl]amino]-2-oxoethyl]-7-methyl-2-oxo-4-phenyl-2H-chromen-6-yl]propenoate

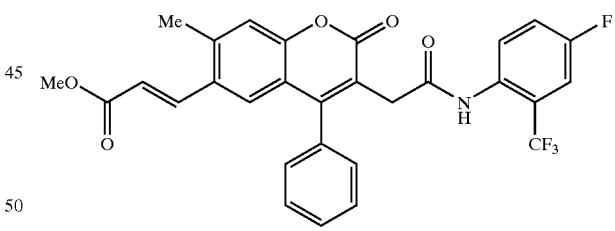

A solution of 2-(6-bromo-7-methyl-2-oxo-4-phenyl-2H-chromen-3-yl)-N-[4-fluoro-2-(trifluoromethyl)phenyl]acetamide (Example 177) (500 mg) in DMF (5 mL) was combined with methyl acrylate (0.14 mL), Et$_3$N (0.21 mL), Pd(OAc)$_2$ (5 mg) and triphenylphosphine (10 mg) under argon atmosphere, and stirred with heating at 120° C. for 10 hours. The reaction solution was combined with water and extracted with ethyl acetate. The extract was washed with diluted hydrochloric acid followed by an aqueous solution of NaHCO$_3$ and water, and then dried over magnesium sulfate, and concentrated under reduced pressure to obtain the title compound as a colorless crystal (360 mg, yield: 72%). An aliquot was recrystallized from ethyl acetate to measure a melting point. Melting point: 233–236° C.

Reference Example 68
Synthesis of ethyl 2-(6,7-dimethyl-2-oxo-4-phenyl-2H-chromen-3-yl)acetate

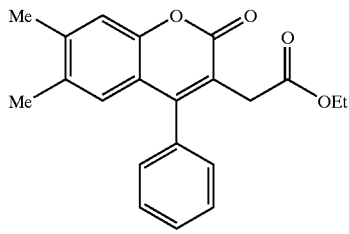

The title compound (yield: 75%) was obtained by the method similar to that in Reference Example 21. Melting point: 127–128° C. (AcOEt-Hxane)

Reference Example 69
Synthesis of ethyl 2-[6,7-bis(acetoxymethyl)-2-oxo-4-phenyl-2H-chromen-3-yl]acetate

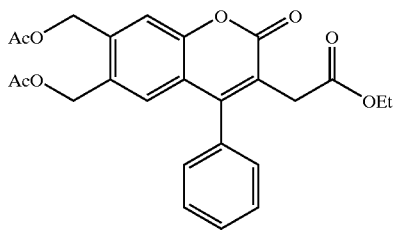

A solution of ethyl 2-(6,7-dimethyl-2-oxo-4-phenyl-2H-chromene-3-yl)acetate (0.50 g) in ethyl acetate (20 ml) was combined with N-bromosuccinimide (0.66 g) and 2,2'-azoisobutyronitrile (24.4 mg), and heated under reflux for 1 hour. After cooling, the reaction solution was washed with water followed by a saturated aqueous solution of sodium hydrogen carbonate and a saturated aqueous solution of sodium chloride. After drying over magnesium sulfate, the solvent was distilled off under reduced pressure. The resultant residue was dissolved in DMF (10 ml), combined with anhydrous sodium acetate (488 mg), and stirred at 60° C. for 5 hours. The reaction solution was combined with water, and the product was extracted with ethyl acetate, and the extract was washed with a saturated aqueous solution of sodium chloride. After drying over magnesium sulfate, the solvent was distilled off under reduced pressure. The resultant residue was purified by a silica gel column chromatography (eluent: ethyl acetate-hexane), and further recrystallized from ether-diisopropyl ether to obtain the title compound (281 mg, yield: 42%). Melting point: 95–96° C.

Reference Example 70
Synthesis of Ethyl 2-[6,7-bis(hydroxymethyl)-2-oxo-4-phenyl-2H-chromen-3-yl]acetate

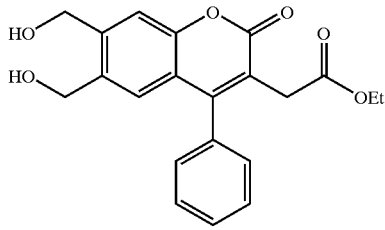

A solution of ethyl 2-[6,7-bis(acetoxymethyl)-2-oxo-4-phenyl-2H-chromen-3-yl]acetate (240 mg) in ethanol (4 ml) was combined with DBU (0.4 ml), and stirred at room temperature for 30 minutes. The reaction solution was diluted with ethyl acetate (30 ml), and then washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. The resultant residue was recrystallized from ether to obtain the title compound (167 mg, yield: 86%). Melting point: 130–131° C.

Reference Example 71
Synthesis of ethyl 2-(2,8-dioxo-4-phenyl-6,8-dihydro-2H-furo[3,4-g]chromen-3-yl)acetate

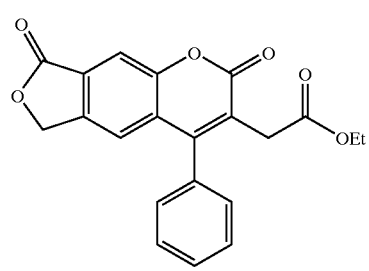

A solution of ethyl 2-[6,7-bis(hydroxymethyl)-2-oxo-4-phenyl-2H-chromen-3-yl]acetate (150 mg) in dichloromethane (3 ml) was combined with manganese dioxide (1.5 g), and stirred at room temperature overnight. After the catalyst was filtered off, the filtrate was concentrated under reduced pressure to obtain the residue, which was recrystallized from THF to obtain the title compound (98 mg, yield: 66%).

Melting point: 222–223° C.

Reference Example 72
Synthesis of 2-(2,8-dioxo-4-phenyl-6,8-dihydro-2H-furo[3,4-g]chromen-3-yl)acetic acid

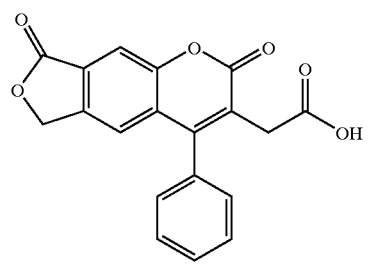

Ethyl 2-(2,8-dioxo-4-phenyl-6,8-dihydro-2H-furo[3,4-g]chromen-3-yl)acetate (58 mg) was dissolved in acetic acid (2 ml) and concentrated hydrochloric acid (1 ml), and heated under reflux for 30 minutes. The reaction solution was concentrated under reduced pressure to obtain the residue, which was dissolved in a solvent mixture of THF (10 ml) and ethyl acetate (50 ml), and then washed with water followed by a saturated aqueous solution of sodium chloride. After drying over magnesium sulfate, the solvent was distilled off under reduced pressure, and the residue was recrystallized from THF-isopropyl ether to obtain the title compound (72 mg, yield: 92%). Melting point: 226–227° C.

Example 219
Synthesis of 2-[7-chloro-6-(cyanomethyl)-2-oxo-4-phenyl-2H-chromen-3-yl]-N-(4-chloro-2-trifluoromethylphenyl)acetamide

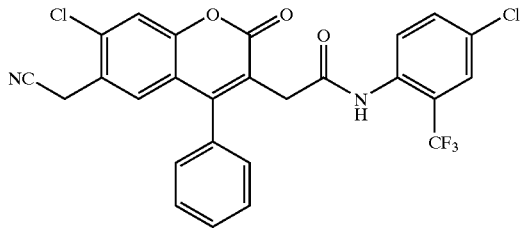

A solution of 2-[6-(bromomethyl)-7-chloro-2-oxo-4-phenyl-2H-chromen-3-yl]acetic acid (1.6 g) in THF (40 ml) was combined with DMF (5 drops) and oxalyl chloride (0.7 ml), and stirred at room temperature for 1 hour. The reaction solution was concentrated under reduced pressure to obtain the residue, which was dissolved in THF (20 ml) and added dropwise to a suspension of 4-chloro-2-trifluoromethylaniline (0.55 ml) and sodium hydride (60%, in oil) (176 mg) in THF (20 ml) at 0° C. After stirring at room temperature for 12 hours, the reaction solution was combined with water, and the product was extracted with ethyl acetate. The extract was washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. The resultant crude crystal of 2-[6-(bromomethyl)-7-chloro-2-oxo-4-phenyl-2H-chromene-3-yl]-N-(4-chloro-2-trifluoromethylphenyl)acetamide was dissolved in DMF (6 ml), combined with sodium cyanide (0.13 g), and stirred for 3 hours. The reaction solution was combined with water to form a precipitate, which was filtered and washed with water followed by methanol and ether. The precipitate thus obtained was purified by a silica gel column chromatography (eluent: chloroform-ethyl acetate-hexane=5:1:4), and further recrystallized from THF-diisopropyl ether to obtain the title compound (480 mg, yield: 55%). Melting point: 247–248° C.

Example 220
Synthesis of 2-[6-(aminoethyl)-7-chloro-2-oxo-4-phenyl-2H-chromen-3-yl]-N-(4-chloro-2-trifluoromethylphenyl)acetamide

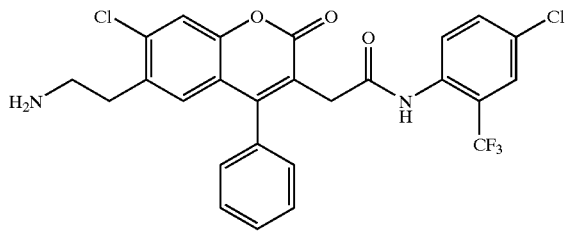

A solution of 2-[7-chloro-6-(cyanomethyl)-2-oxo-4-phenyl-2H-chromen-3-yl]-N-(4-chloro-2-trifluoromethylphenyl)acetamide (100 mg) in THF (5 ml) was combined with Raney-cobalt (100 mg), and stirred under hydrogen atmosphere (4.5 atm) at room temperature for 7 hours. After the catalyst was filtered off, the filtrate was concentrated under reduced pressure to obtain the residue, which was recrystallized from ethyl acetate to obtain the title compound (27 mg, yield: 27%). Melting point: 165–167° C.

Example 221
Synthesis of 2-(2,8-dioxo-4-phenyl-6,8-dihydro-2H-furo[3,4-g]chromen-3-yl)-N-[4-fluoro-2-(trifluoromethyl)phenyl]acetamide

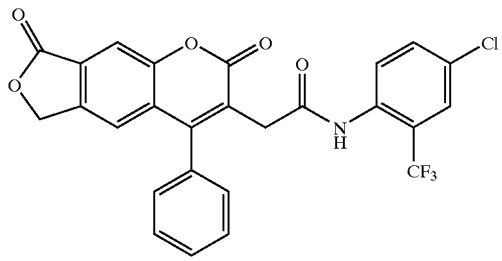

The title compound (yield: 71%) was obtained by the method similar to that in Example 15. Melting Point: 253–254° C. (AcOEt-IPE).

Example 222
Synthesis of 2-[7-chloro-6-[(1-oxide-4-phenyl-1-piperazinyl)methyl]-2-oxo-4-phenyl-2H-chromen-3-yl]-N-[4-chloro-2-(trifluoromethyl)phenyl]acetamide

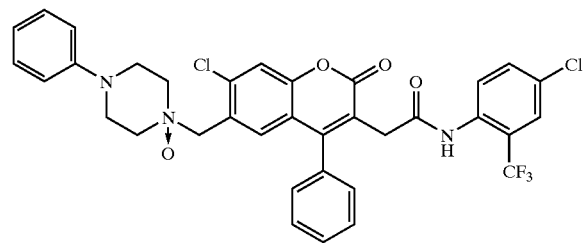

A solution of 2-[7-chloro-2-oxo-4-phenyl-6-[(4-phenyl-1-piperazinyl)methyl]-2H-chromen-3-yl]-N-[4-chloro-2-(trifluoromethyl)phenyl]acetamide (1.0 g) in chloroform (5 ml) was combined with mCPBA (0.41 g), and stirred at room temperature for 30 minutes. The reaction solution was subjected as it was to a silica gel column chromatography (eluent: ethyl acetate-methanol-aqueous ammonia=85:15:1) for purification, and followed by recrystallization from ethyl acetate-diisopropyl ether to obtain the title compound (218 mg, yield: 21%). Melting point: 157–159° C.

Example 223
Synthesis of 2-[7-chloro-6-[(4-oxide-4-phenyl-1-piperazinyl)methyl]-2-oxo-4-phenyl-2H-chromen-3-yl]-N-[4-chloro-2-(trifluoromethyl)phenyl]acetamide

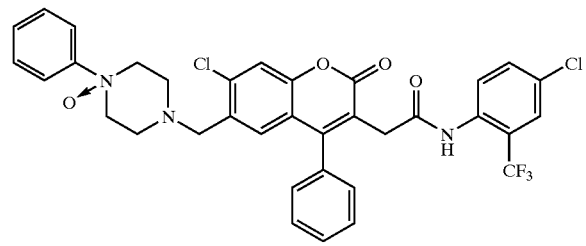

A solution of 2-[7-chloro-2-oxo-4-phenyl-6-[(4-phenyl-1-piperazinyl)methyl]-2H-chromen-3-yl]-N-[4-chloro-2-(trifluoromethyl)phenyl]acetamide (1.0 g) in chloroform (5 ml) was combined with mCPBA (0.41 g), and stirred at room temperature for 30 minutes. The reaction solution was subjected as it was to a silica gel column chromatography (eluent: ethyl acetate-methanol-aqueous ammonia=85:15:1)

to fractionate 2-[7-chloro-6-[(1-oxide-4-phenyl-1-piperazinyl)methyl]-2-oxo-4-phenyl-2H-chromen-3-yl]-N-[4-chloro-2-(trifluoromethyl)phenyl]acetamide (Example 222), after which the remaining trace components were further purified by HPLC (CHIRALCEL OD, hexane-ethanol=8:2) to obtain the title compound (71 mg, yield: 7%). Melting point: 183–184° C.

Example 224

Synthesis of 2-[7-chloro-2-oxo-4-phenyl-6-[(4-phenyl-1-piperazinyl)methyl]-2H-chromen-3-yl]-N-[4-chloro-2-(trifluoromethyl)phenyl]acetamide hydrochloride

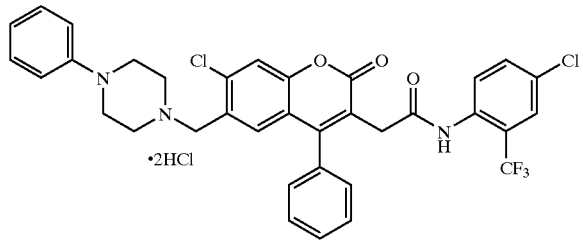

A solution of 2-[6-(bromomethyl)-7-chloro-2-oxo-4-phenyl-2H-chromen-3-yl]acetic acid (0.41 g) in THF (10 ml) was combined with DMF (1 drop) and oxalyl chloride (0.2 ml), and stirred at room temperature for 1 hour. The reaction solution was concentrated under reduced pressure to obtain the residue, which was dissolved in THF (5 ml) and added dropwise to a suspension of 4-chloro-2-trifluoromethylaniline (0.14 ml) and sodium hydride (60%, in oil) (44 mg) in THF (5 ml) at 0° C. After stirring at room temperature for 12 hours, the reaction solution was combined with water, and the product was extracted with ethyl acetate. The extract was washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. A solution of the resultant crude crystal of 2-[6-(bromomethyl)-7-chloro-2-oxo-4-phenyl-2H-chromen-3-yl-N-(4-chloro-2-trifluoromethylphenyl)acetamide in DMF (10 ml) was combined with 1-phenyl-piperazine (0.166 g) and potassium carbonate (0.285 g), and stirred at 80° C. for 30 minutes. After cooling, the reaction solution was diluted with ethyl acetate (5 ml), and poured into water (120 ml). The precipitate formed was filtered and washed with water (20 ml) followed by ethanol (10 ml). The crystal filtered was dissolved in THF (6 ml), and then combined with concentrated hydrochloric acid (0.26 ml), and stirred for 20 minutes. The precipitate was filtered, and washed with ethyl acetate to obtain the title compound (491 mg, yield: 70%). Melting point: 238–239° C.

Example 225

Synthesis of 2-[7-chloro-2-oxo-4-phenyl-6-[(4-phenyl-1-piperazinyl)methyl]-2H-chromen-3-yl]-N-[4-chloro-2-(trifluoromethyl)phenyl]acetamide methansulfonate

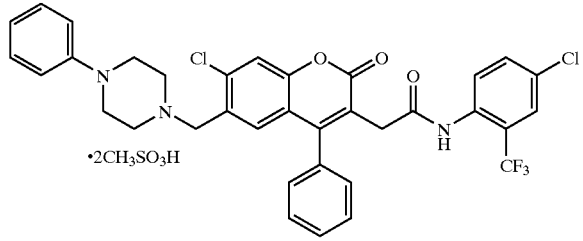

The title compound (yield: 67%) was obtained by the method similar to that in Example 224. Melting Point: 198–204° C. (THF-EtOH).

Example 226

Synthesis of 2-[7-chloro-2-oxo-4-phenyl-6-[(4-phenyl-1-piperazinyl)methyl]-2H-chromen-3-yl]-N-[4-chloro-2-(trifluoromethyl)phenyl]acetamide (Alternative Synthesis Method of the Compound of Example 75)

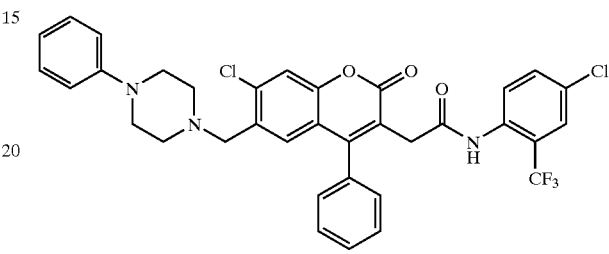

A solution of 2-[6-(bromomethyl)-7-chloro-2-oxo-4-phenyl-2H-chromen-3-yl]acetic acid (0.41 g) in THF (10 ml) was combined with DMF (1 drop) and oxalyl chloride (0.2 ml), and stirred at room temperature for 1 hour. The reaction solution was concentrated under reduced pressure to obtain the residue, which was dissolved in THF (5 ml) and added dropwise to a suspension of 4-chloro-2-trifluoromethylaniline (0.14 ml) and sodium hydride (66%, in oil) (44 mg) in THF (5 ml) at 0° C. After stirring at room temperature for 12 hours, the reaction solution was combined with water, and the product was extracted with ethyl acetate. The extract was washed with a 1 N solution of hydrochloric acid followed by a saturated aqueous solution of sodium chloride, a saturated aqueous solution of sodium hydrogen carbonate and a saturated aqueous solution of sodium chloride, and after drying over magnesium sulfate, the solvent was distilled off under reduced pressure. A solution of the resultant crude crystal of 2-[6-(bromomethyl)-7-chloro-2-oxo-4-phenyl-2H-chromen-3-yl]-N-(4-chloro-2-trifluoromethylphenyl)acetamide in DMF (10 ml) was combined with 1-phenyl piperazine (0.166 g) and potassium carbonate (0.285 g), and stirred at 80° C. for 30 minutes. After cooling, the reaction solution was diluted with ethyl acetate (5 ml), and poured into water (120 ml). The precipitate formed was filtered, and washed with water (20 ml) followed by ethanol (10 ml). The crystal filtered was dissolved in THF (6 ml), and then combined with concentrated hydrochloric acid (0.26 ml), and stirred for 20 minutes. The precipitate was filtered and washed with ethyl acetate. A suspension of the precipitate filtered in ethanol (10 ml) was combined with a saturated aqueous solution of sodium hydrogen carbonate (30 ml), and stirred for 20 minutes. The precipitate was filtered and washed with water (20 m) followed by ethanol (10 ml). The crystal filtered was dissolved in THF (20 ml), and then dried over magnesium sulfate, and then concentrated under reduced pressure. The resultant residue was recrystallized from THF-ethanol to obtain the title compound as a colorless crystal (0.431 g, yield: 63%). Melting point: 201–203° C.

Reference Example 73
Synthesis of ethyl [7-chloro-2-oxo-4-phenyl-6-[(4-phenylpiperazin-1-yl)methyl]-2H-chromen-3-yl]acetate.hydrochloride

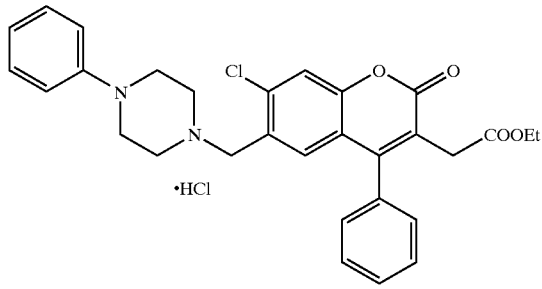

Ethyl (7-chloro-6-methyl-2-oxo-4-phenyl-2H-chromen-3-yl)acetate (100 g), N-bromosuccinimide (59.9 g) and 2-2'-azobis-2,4-dimethylvaleronitrile (3.48 g) were suspended in AcO$^t$Bu (700 ml) under nitrogen atmosphere, and stirred at 80° C. for 2 hours. The reaction solution was cooled, and treated dropwise with triethylamine (34.03 g) at 25° C. or lower over 10 minutes, followed by treatment dropwise with phenylpiperazine (45.47 g) at 40° C. or lower internal temperature over 15 minutes. After completing dropwise addition, the mixture was stirred for 2 hours. To the reaction solution was added dropwise ethanol (500 ml) over 15 minutes, and further added dropwise water (200 ml) over 15 minutes. After completing dropwise addition, the mixture was stirred at room temperature for 30 minutes, and further stirred with cooling in ice for 1 hour. The crystal formed was filtered and washed with 50% ethanol to obtain the crude crystal (100 g, yield: 69%) of ethyl [7-chloro-2-oxo-4-phenyl-6-[(4-phenylpiperazine-1-yl)methyl]-2H-chromene-3-yl]acetate.

The resultant crude crystal (70 g) was suspended in a mixture solution of ethanol (280 ml) and AcO$^t$Bu (280 ml), and combined with concentrated hydrochloric acid (12.2 ml) at 40° C. After stirring at 40° C. for 30 minutes, the mixture was cooled to room temperature, and further cooled with cooling in ice, and stirred for 1 hour. The crystal formed was filtered and washed with 50% ethanol to obtain the title compound (72 g, yield: 96%) as a white crystal.

NMR (CDCl$_3$) δ: 1.23 (3H, t, J=7 Hz), 3.20–3.50 (4H, m), 3.41 (2H, s), 3.50–3.65 (2H, m), 3.70–3.90 (2H, m), 4.14 (2H, q, J=7 Hz), 4.20–4.35 (2H, m), 6.95–7.10 (3H, m), 7.20–7.40 (5H, m), 7.52 (1H, s), 7.50–7.65 (3H, m), 7.80–7.90 (1H, brs).

Reference Example 74
Synthesis of [7-chloro-2-oxo-4-phenyl-6-[(4-phenylpiperazin-1-yl)methyl]-2H-chromen-3-yl]acetic acid

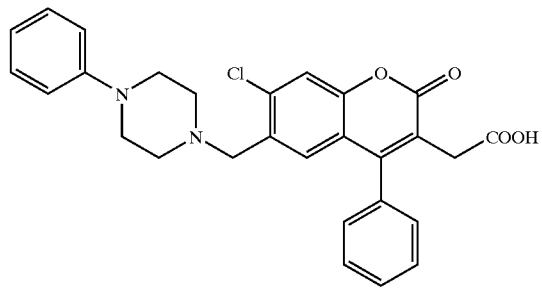

Ethyl [7-chloro-2-oxo-4-phenyl-6-[(4-phenylpiperazin-1-yl)methyl]-2H-chromen-3-yl]acetate.hydrochloride (40 g) was suspended in ethanol (120 ml), and combined with a 2 N aqueous solution of sodium hydroxide (144.5 ml). A yellow clear solution obtained by stirring at 70° C. for 1 hour was added dropwise to a mixture solution of ethanol (40 ml) and 6 N hydrochloric acid (49.4 ml) over 45 minutes. The reaction solution was adjusted to pH 5.5 to 6.0 with sodium hydrogen carbonate at 40° C. After pH became stable, the mixture was stirred at 35 to 40° C. internal temperature for 15 minutes, and cooled to room temperature, and stirred at room temperature for 30 minutes. The crystal formed was filtered and washed with 30% ethanol to obtain the title compound (34 g, yield: 96%) as a white crystal.

NMR (CDCl$_3$) δ: 2.45–2.70 (2H, m), 2.90–3.25 (3H, m), 3.39 (2H, s), 3.40–3.85 (4H, m), 4.20–4.40 (2H, m), 6.80–7.00 (2H, m), 7.10–7.70 (10H, m).

Reference Example 75
Synthesis of [6-(bromomethyl)-7-chloro-4-(3-chlorophenyl)-2-oxo-2H-chromene-3-yl]acetic acid

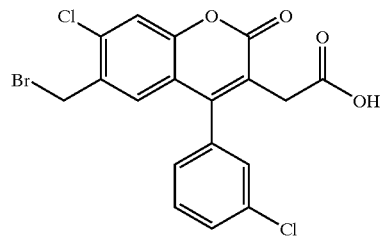

The title compound was obtained by the method similar to that in Reference Example 24.

NMR (CDCl$_3$) δ: 3.36 (1H, d, J=17 Hz), 3.47 (1H, d, J=17 Hz), 4.60 (2H, s), 7.07 (1H, s), 7.18 (1H, m), 7.28 (1H, m), 7.48 (1H, s), 7.55 (2H, m).

Example 227
Synthesis of 2-[7-chloro-2-oxo-4-phenyl-6-[(4-phenyl-1-piperazinyl)methyl]-2H-chromen-3-yl]-N-[4-chloro-2-(trifluoromethyl)phenyl]acetamide (Alternative Synthesis Method of the Compound of Example 75)

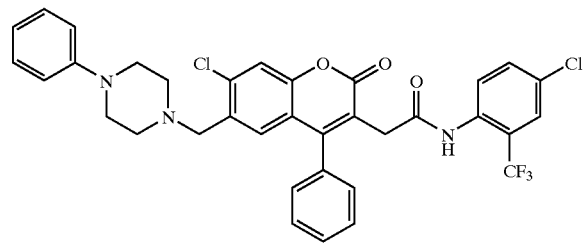

[7-Chloro-2-oxo-4-phenyl-6-[(4-phenylpiperazine-1-yl)methyl]-2H-chromen-3-yl]acetic acid (500 g) was suspended in a mixture solution of THF (5 L) and DMF (5 ml), and cooled to 5° C. or lower with cooling in ice. Thionyl chloride (150 ml) was added dropwise at the same temperature. After completing dropwise addition, the mixture was allowed to warm to room temperature, and stirred at 25 to 30° C. for 5 hours. The reaction solution was combined with toluene (2 L) and concentrated under reduced pressure. The resultant residue was suspended in THF (5 L), combined with 4-chloro-2-(trifluoromethyl)aniline (250 g), and refluxed at 80° C. for 5 hours. The reaction solution was cooled to 40° C., and combined with acetone (5 L) and water (2.5 L). The mixture was adjusted to pH 7.6 with 25% aqueous ammonia, and stirred at 15 to 20° C. for 30 minutes. The crystal precipitated was separated by centrifugal separator, and washed with acetone and water to obtain the title compound (487 g, yield: 71%).

Melting point: 201–203° C.

Example 228–248

The compounds of table 35 were obtained by the method similar to that in Example 74.

TABLE 35

| Example number | R$^1$ | R$^2$ | Yield (%) | Melting Point (° C.) (Recrystallization solvent) |
|---|---|---|---|---|
| 228 | 4-Cl | 2-CF$_3$, 4-Cl | 47 | 215–217 (AcOEt-hexane) |
| 229 | 4-Cl | 2-CF$_3$, 4-F | 22 | 185–187 (THF-AcOEt) |
| 230 | 3-Cl | 2-CF$_3$, 4-Cl | 42 | 203–205 (AcOEt-hexane) |
| 231 | 3-Cl | 2-CF$_3$, 4-F | 59 | 180–182 (THF-AcOEt) |
| 232 | 4-F | 2-CF$_3$, 4-Cl | 48 | 205–208 (AcOEt-hexane) |
| 233 | 4-F | 2-CF$_3$, 4-F | 43 | 201–202 (THF-AcOEt) |
| 234 | 3-F | 2-CF$_3$, 4-Cl | 86 | 196–199 (THF-AcOEt) |
| 235 | 3-F | 2-CF$_3$, 4-F | 61 | 180–182 (THF-AcOEt) |
| 236 | 3,4-F$_2$ | 2-CF$_3$, 4-Cl | 55 | 192–195 (THF-AcOEt) |
| 237 | 3,4-F$_2$ | 2-CF$_3$, 4-F | 46 | 196–199 (THF-AcOEt) |
| 238 | 3,4-F$_2$ | 2-Me, 4-Cl | 55 | 203–206 (THF-AcOEt) |
| 239 | 3-Me | 2-CF$_3$, 4-Cl | 58 | 190–192 (THF-AcOEt) |
| 240 | 3-Me | 2-CF$_3$, 4-F | 49 | 168–170 (THF-AcOEt) |
| 241 | 3-Me | 2-Me, 4-Cl | 67 | 235–238 (THF-AcOEt) |
| 242 | 3,4-(Me)$_2$ | 2-CF$_3$, 4-Cl | 70 | 208–211 (THF-AcOEt) |
| 243 | 3,4-(Me)$_2$ | 2-CF$_3$, 4-F | 77 | 186–187 (THF-AcOEt) |
| 244 | 3-CF$_3$ | 2-CF$_3$, 4-Cl | 41 | 183–186 (AcOEt-hexane) |
| 245 | 3-CF$_3$ | 2-CF$_3$, 4-F | 62 | 198–201 (THF) |
| 246 | 3-CF$_3$ | 2-Me, 4-Cl | 89 | 232–234 (THF) |
| 247 | 2,3,5-(Me)$_3$, 4-OH | 2-CF$_3$, 4-Cl | 22 | 216–218 (THF-AcOEt) |
| 248 | 2,3,5-(Me)$_3$, 4-OH | 2-CF$_3$, 4-F | 22 | 220–221 (THE-AcOEt) |

Example 249–268

The compounds of table 36 were obtained by the method similar to that in Example 74.

TABLE 36

| Example number | R$^1$ | R$^2$ | Yield (%) | Melting Point (° C.) (Recrystallization solvent) |
|---|---|---|---|---|
| 249 | H | 2-Me, 4-Cl | 66 | 213–216 (AcOEt-IPE) |
| 250 | H | 2,3,4-F$_3$ | 47 | 169–174 (AcOEt-IPE) |
| 251 | 4-Cl | 2-CF$_3$, 4-Cl | 49 | 194–197 (THF-AcOEt-hexane) |
| 252 | 4-Cl | 2-CF$_3$, 4-F | 49 | 178–184 (THF-AcOEt-hexane) |
| 253 | 4-Cl | 2-Me, 4-Cl | 55 | 218–220 (THF-AcOEt-hexane) |
| 254 | 3-Cl | 2-CF$_3$, 4-Cl | 51 | 193–195 (AcOEt-hexane) |
| 255 | 3-Cl | 2-CF$_3$, 4-F | 37 | 170–174 (AcOEt-hexane) |
| 256 | 3-Cl | 2-Me, 4-Cl | 41 | 199–200 (AcOEt-hexane) |
| 257 | 3-F | 2-CF$_3$, 4-Cl | 49 | 110–114 (AcOEt-hexane) |
| 258 | 3-F | 2-CF$_3$, 4-F | 40 | 184–187 (AcOEt-hexane) |
| 259 | 3-F | 2-Me, 4-Cl | 52 | 211–217 (AcOEt-hexane) |
| 260 | 4-Me | 2-CF$_3$, 4-Cl | 56 | 217–222 (THF-AcOEt-hexane) |

TABLE 36-continued

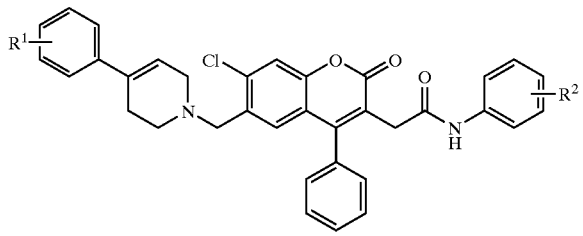

| Example number | R¹ | R² | Yield (%) | Melting Point (° C.) (Recrystallization solvent) |
|---|---|---|---|---|
| 261 | 4-Me | 2-CF₃, 4-F | 45 | 210–219 (THF-AcOEt-hexane) |
| 262 | 4-Me | 2-Me, 4-Cl | 27 | 189–191 (THF-AcOEt-hexane) |
| 263 | 3-Me | 2-CF₃, 4-Cl | 47 | 183–188 (AcOEt-hexane) |
| 264 | 3-Me | 2-CF₃, 4-F | 37 | 134–135 (AcOEt-hexane) |
| 265 | 3-Me | 2-Me, 4-Cl | 28 | 196–200 (AcOEt-hexane) |
| 266 | 3-CF₃ | 2-CF₃, 4-Cl | 10 | 194–196 (AcOEt) |
| 267 | 3-CF₃ | 2-CF₃, 4-F | 53 | 164–167 (AcOEt-hexane) |
| 268 | 3-CF₃ | 2-Me, 4-Cl | 14 | 120 (decomp.) (AcOEt) |

Example 269–271

The compounds of table 37 were obtained by the method similar to that in Example 74.

TABLE 37

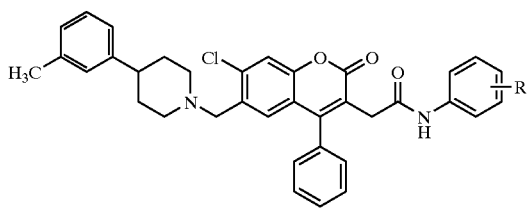

| Example number | R | Yield (%) | Melting Point (° C.) (Recrystallization solvent) |
|---|---|---|---|
| 269 | 2-CF₃, 4-Cl | 33 | 208–211 (AcOEt-hexane) |
| 270 | 2-CF₃, 4-F | 37 | 182–184 (AcOEt-hexane) |
| 271 | 2-Me, 4-Cl | 34 | 177–180 (AcOEt-hexane) |

Example 272–273

The compounds of table 38 were obtained by the method similar to that in Example 74.

TABLE 38

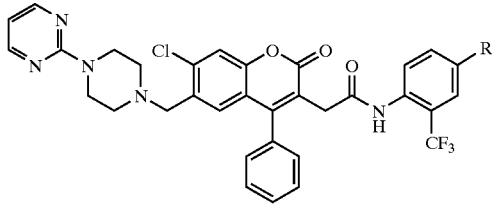

| Example number | R | Yield (%) | Melting Point (° C.) (Recrystallization solvent) |
|---|---|---|---|
| 272 | Cl | 52 | 214–217 (AcOEt-IPE) |
| 273 | F | 55 | 203–205 (AcOEt-IPE) |

Example 274–276

The compounds of table 39 were obtained by the method similar to that in Example 74.

TABLE 39

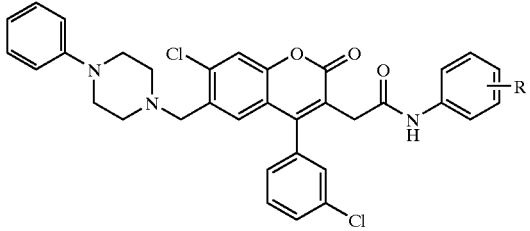

| Example number | R | Yield (%) | Melting Point (° C.) (Recrystallization solvent) |
|---|---|---|---|
| 274 | 2-CF₃, 4-Cl | 67 | 216–218 (THF-AcOEt) |
| 275 | 2-CF₃, 4-F | 64 | 227–229 (THF-AcOEt) |
| 276 | 2-Me, 4-Cl | 73 | 240–242 (THF-AcOEt) |

Example 277–283

The compounds of table 40 were obtained by the method similar to that in Example 203.

TABLE 40

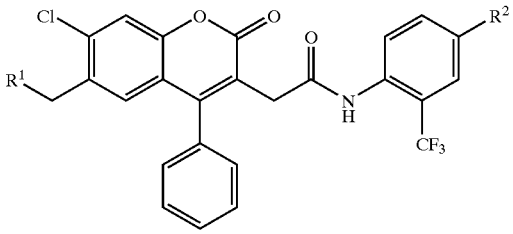

| Example number | R¹ | R² | Yield (%) | Melting Point (° C.) (Recrystallization solvent) |
|---|---|---|---|---|
| 277 | 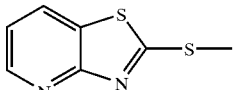 | Cl | 64 | 227–230 (THF-AcOEt) |
| 278 | 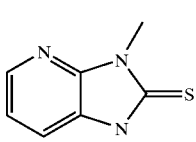 | Cl | 57 | 262–264 (THF-AcOEt) |
| 279 | 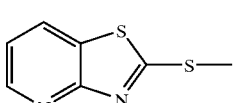 | F | 24 | 212–215 (THF-AcOEt) |
| 280 | 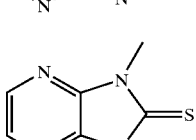 | F | 43 | 245–247 (THF-AcOEt) |
| 281 | 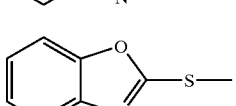 | Cl | 72 | 254–256 (THF-AcOEt) |
| 282 | 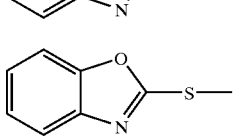 | F | 59 | 251–253 (THF-AcOEt) |
| 283 | CH₃(CH₂)₁₁S | Cl | 6 | 120–122 (THF-AcOEt) |

Reference Example 76–87

The compounds of table 41 were obtained by the method similar to that in Reference Example 13.

TABLE 41

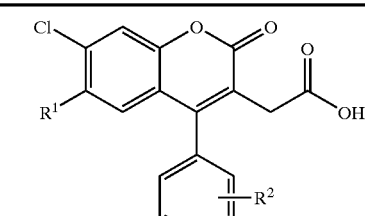

| Ref.Ex. number | R¹ | R² | Yield (%) | Melting Point (° C.) (Recrystallization solvent) |
|---|---|---|---|---|
| 76 | Me | 3-Me | 80 | 250–253 (AcOEt) |
| 77 | Me | 3,5-Me₂ | 61 | 228–230 (AcOEt-IPE) |
| 78 | Me | 4-F | 80 | 253–257 (AcOEt) |
| 79 | Me | 4-Cl | 87 | 238–241 (AcOEt) |
| 80 | Me | 3-Cl, 4-F | 88 | 258 (decomp.) (AcOEt) |

TABLE 41-continued

Cl-[coumarin structure with R1, phenyl-R2, CH2COOH]

| Ref.Ex. number | R¹ | R² | Yield (%) | Melting Point (° C.) (Recrystallization solvent) |
|---|---|---|---|---|
| 81 | Me | 3,4-F₂ | 77 | 262–264 (AcOEt) |
| 82 | Me | 3-Br | 93 | 270 (decomp.) (AcOEt) |
| 83 | Me | 4-OCF₃ | 93 | 183–186 (AcOEt) |
| 84 | Me | 3-OCF₃ | 71 | 187–191 (AcOEt) |
| 85 | F | H | 92 | 209–210 (AcOEt-hexane) |
| 86 | F | 3-Cl | 77 | 213–215 (IPE-hexane) |
| 87 | Me | 3-NO₂ | 74 | 260 (decomp.) (AcOEt) |

Example 284–307

The compounds of table 44 were obtained by the method similar to that in Example 15.

TABLE 42

| Example number | R¹ | R² | R³ | Yield (%) | Melting Point (° C.) (Recrystallization solvent) |
|---|---|---|---|---|---|
| 284 | Me | Cl | 3-Me | 85 | 235–237 (THF-AcOEt) |
| 285 | Me | F | 3-Me | 67 | 218–220 (THF-AcOEt) |
| 286 | Me | Cl | 3,5-(Me)₂ | 65 | 266–267 (THF) |
| 287 | Me | F | 3,5-(Me)₂ | 68 | 274–275 (THF) |
| 288 | Me | Cl | 4-Cl | 80 | 284–286 (THF-AcOEt) |
| 289 | Me | F | 4-Cl | 77 | 272–273 (THF-AcOEt) |
| 290 | Me | Cl | 4-F | 73 | 272–273 (THF-AcOEt) |
| 291 | Me | F | 4-F | 70 | 271–272 (THF-AcOEt) |
| 292 | Me | Cl | 3-Cl, 4-F | 83 | 240–241 (THF-AcOEt) |
| 293 | Me | F | 3-Cl, 4-F | 86 | 230–231 (THF-AcOEt) |
| 294 | Me | Cl | 3,4-F₂ | 69 | 248–251 (THF-AcOEt) |
| 295 | Me | F | 3,4-F₂ | 71 | 253–255 (THF-AcOEt) |
| 296 | Me | Cl | 3-Br | 81 | 221–222 (THF-AcOEt) |
| 297 | Me | F | 3-Br | 80 | 222–223 (THF-AcOEt) |
| 298 | Me | Cl | 4-OCF₃ | 76 | 239–241 (THF-AcOEt) |
| 299 | Me | F | 4-OCF₃ | 70 | 239–240 (THF-AcOEt) |
| 300 | Me | Cl | 3-OCF₃ | 40 | 171–175 (THF-AcOEt) |
| 301 | Me | F | 3-OCF₃ | 51 | 166–169 (THF-AcOEt) |
| 302 | Me | Cl | 3-NO₂ | 80 | 234–236 (THF-AcOEt) |
| 303 | Me | F | 3-NO₂ | 80 | 235–238 (THF-AcOEt) |
| 304 | F | Cl | H | 63 | 199–203 (AcOEt-hexane) |
| 305 | F | F | H | 68 | 204–206 (AcOEt-hexane) |
| 306 | F | Cl | 3-Cl | 67 | 200–201 (AcOEt-hexane) |
| 307 | F | F | 3-Cl | 77 | 206–207 (AcOEt-hexane) |

Example 308

Synthesis of methyl (2E)-3-[3-[7-chloro-3-(2-[[4-chloro-2-(trifluoromethyl)phenyl]amino]-2-oxoethyl)-6-methyl-2-oxo-2H-chromen-4-yl]phenyl]-2-propenoate

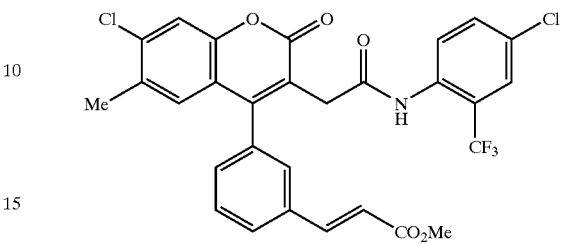

A solution of 2-[4-(3-bromophenyl)-7-chloro-6-methyl-2-oxo-2H-chromene-3-yl]-N-[4-chloro-2-(trifluoromethyl)phenyl]acetamide (500 mg) in DMF (5 ml) was combined with methyl acrylate (0.14 ml), triethylamine (0.21 ml), pd(OAc)₂ (5 ml) and triphenylphosphine (10 mg) under argon atmosphere, and heated at 120° C. for 3 hours. After the reaction was completed, the mixture was combined with water, and extracted with ethyl acetate. The extract was washed with water, dried over magnesium sulfate, and then concentrated. The resultant residue was purified by a silica gel chromatography (eluent: hexane-ethyl acetate=2:1), and then recrystallized from THF-ethyl acetate to obtain the title compound as a colorless crystal (333 mg, yield: 67%). Melting point: 202–204° C.

Example 309

Synthesis of (2E)-3-[3-[7-chloro-3-(2-[[4-chloro-2-(trifluoromethyl)phenyl]amino]-2-oxoethyl)-6-methyl-2-oxo-2H-chromen-4-yl]phenyl]-2-propenoic acid

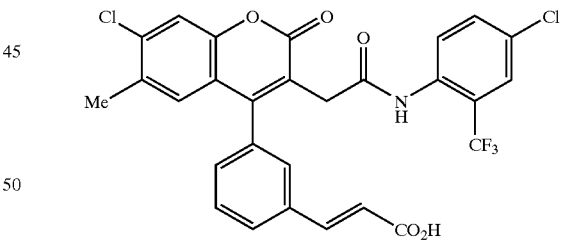

A solution of ethyl (2E)-3-[3-[7-chloro-3-(2-[[4-chloro-2-(trifluoromethyl)phenyl]amino]-2-oxoethyl)-6-methyl-2-oxo-2H-chromen-4-yl]phenyl]-2-propenoate (200 mg) in a mixture of ethanol (5 ml) and THF (2 ml) was combined with a 1 N aqueous solution of sodium hydroxide (3 ml), and stirred at room temperature for 4 hours. After 1 N hydrochloric acid (10 ml) was added, the mixture was extracted with ethyl acetate. The extract was washed with water, dried over magnesium sulfate, and then concentrated. The resultant crude crystal was recrystallized from THF-ethyl acetate to obtain the title compound as a colorless crystal (137 mg, yield: 70%). Melting point: 191–194° C.

Example 310

Synthesis of 2-[4-(3-aminophenyl)-7-chloro-6-methyl-2-oxo-2H-chromen-3-yl]-N-[4-chloro-2-(trifluoromethyl)phenyl]acetamide

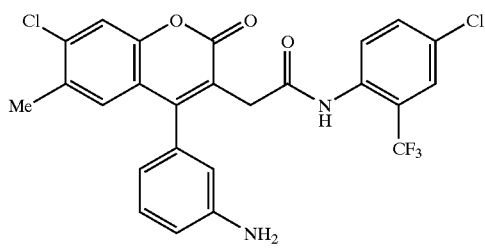

A mixture solution of 2-[7-chloro-6-methyl-4-(3-nitrophenyl)-2-oxo-2H-chromen-3-yl]-N-[4-chloro-2-(trifluoromethyl)phenyl]acetamide (300 mg) in ethanol (2 ml) and THF (5 ml) was combined with Raney-nickel (50 mg), and stirred under hydrogen atmosphere at room temperature for 5 hours. After catalyst was filtered off, the reaction solution was concentrated. The resultant residue was purified by a silica gel chromatography (eluent: hexane-ethyl acetate=2:1), and further recrystallized from THF-ethyl acetate to obtain the title compound as a colorless crystal (166 mg, yield: 59%). Melting point: 206–207° C.

Example 311–316

The compounds of table 43 were obtained by the method similar to that in Example 1.

TABLE 43

| Example number | R$^1$ | R$^2$ | Yield (%) | Melting Point (° C.) (Recrystallization solvent) |
|---|---|---|---|---|
| 311 | 3-Cl | 3,5-(CF$_3$)$_2$ | 72 | 236–237 (THF-AcOEt) |
| 312 | 3-Cl | 2,5-(CF$_3$)$_2$ | 64 | 242–244 (THF-AcOEt) |
| 313 | 3,5-(Me)$_2$ | 2-Me, 4-Cl | 64 | 275–276 (THF) |
| 314 | Me | 2,3,5-(Me)$_3$, 4-OH | 49 | 150–151 (THF-AcOEt) |
| 315 | Me | 2,3,5-(Me)$_3$, 4-OH | 70 | 173–176 (THF-AcOEt) |
| 316 | Me | 2,3,5-(Me)$_3$, 4-OH | 73 | 248 (decomp.) (THF-IPE) |

Reference Example 88–93

The compounds of table 44 were obtained by the method similar to that in Reference Example 13.

TABLE 44

| Ref.Ex. number | R | Yield (%) | Melting Point (° C.) (Recrystallization solvent) |
|---|---|---|---|
| 88 | 7-Cl | 83 | 178–181 (AcOEt-IPE) |
| 89 | 6-OMe, 7-Cl | 86 | 226–229 (AcOH-H$_2$O) |
| 90 | 6,7-Me$_2$ | 90 | 213–215 (AcOH) |
| 91 | 6-Cl, 7-Me | 85 | 218–220 (AcOH) |
| 92 | 6,7-Cl$_2$ | 79 | 231–233 (AcOH) |
| 93 | 6,7-F$_2$ | 80 | 199–201 (AcOH) |

Example 317–328

The compounds of table 45 were obtained by the method similar to that in Example 15.

TABLE 45

| Example number | R$^1$ | R$^2$ | Yield (%) | Melting Point (° C.C) (Recrystallization solvent) |
|---|---|---|---|---|
| 317 | 7-Cl | Cl | 70 | 160–164 (AcOEt-hexane) |
| 318 | 7-Cl | F | 61 | 170–175 (AcOEt-hexane) |
| 319 | 6-OMe, 7-Cl | Cl | 78 | 209–211 (AcOEt-hexane) |
| 320 | 6-OMe, 7-Cl | F | 78 | 202–206 (AcOEt-hexane) |
| 321 | 6,7-Me$_2$ | Cl | 76 | 206–208 (AcOEt-hexane) |
| 322 | 6,7-Me$_2$ | F | 76 | 200–202 (AcOEt-hexane) |
| 323 | 6-Cl, 7-Me | Cl | 82 | 222–225 (AcOEt-hexane) |
| 324 | 6-Cl, 7-Me | F | 85 | 196–199 (AcOEt-hexane) |
| 325 | 6,7-Cl$_2$ | Cl | 82 | 213–215 (AcOEt-hexane) |
| 326 | 6,7-Cl$_2$ | F | 87 | 222–224 (AcOEt-hexane) |
| 327 | 6,7-F$_2$ | Cl | 85 | 192–194 (AcOEt-hexane) |
| 328 | 6,7-F$_2$ | F | 70 | 176–178 (AcOEt-hexane) |

Reference Example 94

(4-Chloro-2-hydroxy-5-methylphenyl)(pyridin-3-yl)methanone

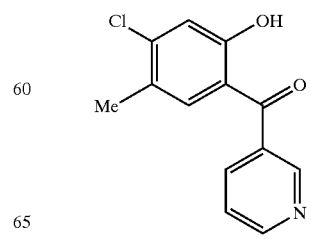

A solution of 3-pyridinecarbaldehyde (2.2 g) in THF (50 ml) was treated dropwise with a solution (50 ml) of Grignard reagent prepared from 1-bromo-4-chloro-2-methoxy-5-methylbenzene (5.0 g) and magnesium (0.8 g) in THF at 0° C., and stirred for 1 hour. The reaction solution was combined with a saturated aqueous solution of ammonium chloride, and extracted with ethyl acetate. The extract was washed with water, dried over magnesium sulfate, and concentrated under reduced pressure. The resultant residue was used in the next step without purification, combined with toluene (150 ml) and manganese dioxide (15 g), and heated under reflux with dehydrating using Deen Stark for 1 hour. After the reaction was completed, the reaction solution was filtered using celite, the filtrate was concentrated under reduced pressure. The resultant residue was combined with methylene chloride (50 ml) and a 1 N solution of BBr$_3$/methylene chloride (60 ml), and stirred at room temperature overnight. After the reaction was completed, water was added, and the solvent was distilled off under reduced pressure. The resultant residue was neutralized with the addition of a saturated aqueous solution of sodium hydrogen carbonate, and then extracted with ethyl acetate. The extract was washed with water, and then dried over magnesium sulfate, and concentrated under reduced pressure. The resultant residue was purified by a silica gel column (eluent: ethyl acetate) to obtain the title compound as an oil (2.4 g).

NMR (CDCl$_3$) δ: 2.28 (3H, s), 7.14 (1H, s), 7.37 (1H, s), 7.50 (1H, dd, J=8 Hz, 4 Hz), 8.00 (1H, m), 8.84 (1H, dd, J=4 Hz, 2H), 8.90 (1H, d, J=2 Hz), 11.75 (1H, s).

Reference Example 95

Synthesis of (7-chloro-6-methyl-2-oxo-4-pyridin-3-yl-2H-chromen-3-yl)acetic Acid.Hydrochloride

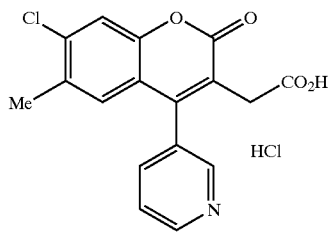

The title compound (yield: 67%) was obtained by the method similar to that in Reference Example 13. Melting Point: 279–281° C. (methanol).

Reference Example 96

Synthesis of [4-chloro-2-hydroxy-5-[(4-phenylpiperazin-1-yl)methyl]phenyl](pyridin-3-yl)methanone

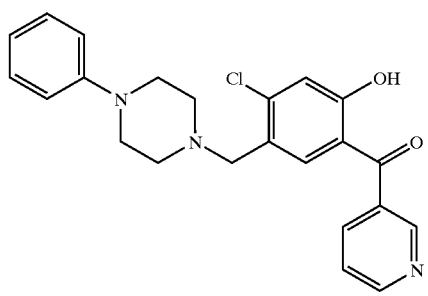

The title compound (yield: 63%) was obtained by the method similar to that in Reference Example 93.

NMR (CDCl$_3$) δ: 2.65 (4H, t, J=5 Hz), 3.14 (4H, t, J=5 Hz), 3.59 (2H, s), 6.80–9.00 (12H, m).

Reference Example 97

Synthesis of ethyl [7-chloro-2-oxo-6-[(4-phenylpiperazin-1-yl)methyl]-4-pyridin-3-yl-2H-chromen-3-yl]acetate

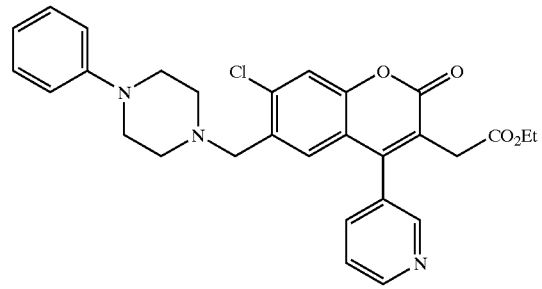

The title compound (yield: 22%) was obtained by the method similar to that in Reference Example 21. Melting Point: 153–157° C. (ethyl acetate-isopropyl ether).

Reference Example 98

Synthesis of ethyl [7-chloro-6-methyl-2-oxo-4-pyridin-3-yl-2H-chromen-3-yl]acetate (Alternative Synthesis Method of the Compound of Reference Example 21)

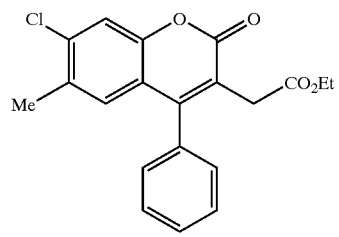

(4-Chloro-2-hydroxy-5-methylphenyl)(phenyl)methanone (130 g) was suspended in acetonitrile (325 ml), and combined with DBU (217 g) at room temperature. The mixture was heated to approximately 40° C., and treated dropwise with a solution of ethylsuccinyl chloride (147 g) in acetonitrile (234 ml) with keeping the reaction temperature at 40 to 45° C. After completing dropwise addition, the mixture was stirred at 40 to 45° C. for 30 minutes. The mixture was combined with water, stirred at 40° C. for 30 minutes, cooled to room temperature, and further stirred at 0 to 5° C. internal temperature with cooling in ice for 1 hour. The crystal precipitated was filtered, and washed with cooled CH$_3$CN—H$_2$O=3:2 to obtain the title compound as a slightly tan white crystal (140 g, yield: 74%).

NMR (CDCl$_3$) δ: 1.23 (3H, t, J=7 Hz), 2.28 (2H, s), 3.36 (2H, s), 4.13 (2H, t, J=7 Hz), 6.84 (1H, s), 7.20–7.35 (2H, m), 7.41 (1H, s), 7.45–7.60 (3H, m).

Example 329–330

The compounds of table 46 were obtained by the method similar to that in Example 15.

TABLE 46

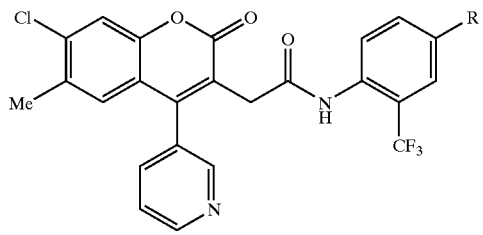

| Example number | R | Yield (%) | Melting Point (° C.) (Recrystallization solvent) |
|---|---|---|---|
| 329 | Cl | 64 | 212–215 (THF-AcOEt) |
| 330 | F | 53 | 213–215 (THF-AcOEt) |

Example 331

Synthesis of 2-[7-chloro-2-oxo-4-phenyl-6-[(4-phenyl-1-piperazinyl)methyl]-2H-chromen-3-yl]-N-(4-hydroxy-2,3,5-trimethylphenyl)acetamide

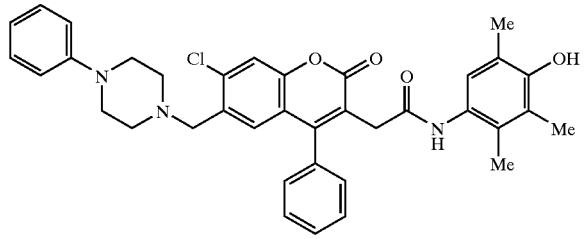

A solution of 2-[7-chloro-2-oxo-4-phenyl-6-[(4-phenyl-1-piperazinyl)methyl]-2H-chromen-3-yl]-N-(4-hydroxy-2,3,5-trimethylphenyl)acetic acid (200 mg) in DMF (2 ml) was combined with 4-amino-2,3,6-trimethylphenol (68 mg), 1-ethyl-3-(3-dimethylaminopropyl)carbodiimide (118 mg) and 1-hydroxybenzotriazole (83 mg), and stirred at room temperature overnight. The reaction solution was combined with water, and the precipitate formed was filtered. The resultant crude crystal was purified by a silica gel chromatography (eluent: hexane-ethyl acetate=1:1), and further recrystallized from ethyl acetate to obtain the title compound as a colorless crystal (84 mg, yield: 33%). Melting point: 193° C. (decomp.).

Example 332–333

The compounds of table 47 were obtained by the method similar to that in Example 331.

TABLE 47

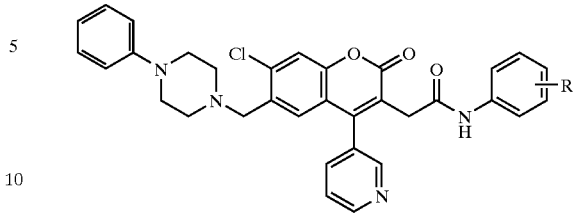

| Example number | R | Yield (%) | Melting Point (° C.) (Recrystallization solvent) |
|---|---|---|---|
| 332 | 2-Me, 4-Cl | 20 | 290–292 (AcOEt-IPE) |
| 333 | 2,3,5-(Me)$_3$, 4-OH | 36 | 242–246 (AcOEt-IPE) |

Example 334

Synthesis of 2-[7-chloro-2-oxo-6-[(4-phenyl-1-piperazinyl)methyl]-4-(3-pyridinyl)-2H-chromen-3-yl]-N-[4-chloro-2-(trifluoromethyl)phenyl]acetamide

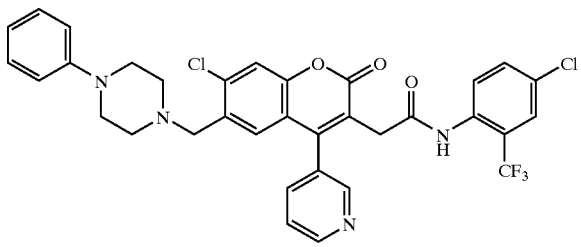

A suspension of ethyl 7-chloro-2-oxo-6-[(4-phenyl-1-piperazinyl)methyl]-4-(3-pyridinyl)-2H-chromen-3-yl] acetate (500 mg, 0.97 mmol) in ethanol (10 ml) was combined with a 2 N aqueous solution of sodium hydroxide (1.5 ml), and heated and stirred at 70° C. for 1 hour. After allowing to cool, the mixture was combined with 1 N hydrochloric acid (3 ml), and neutralized with a saturated aqueous solution of sodium hydrogen carbonate. The solvent was distilled off under reduced pressure, and the residue was boiled azeotropically with toluene to remove water. The resultant yellow powder (350 mg) was combined with THF (5 ml), DMF (1 drop) and thionyl chloride (0.22 ml), and stirred at room temperature for 2 hours. The solvent was distilled off under reduced pressure, and the residue was combined with THF (15 ml) and 2-amino-5-chlorobenzotrifluoride (0.38 ml, 2.1 mmol), and stirred at 80° C. for 15 hours. After allowing to cool, the mixture was combined with an aqueous solution of ammonium chloride, and extracted with ethyl acetate. The extract was washed with a saturated aqueous solution of sodium chloride, and dried over magnesium sulfate, and then the solvent was distilled off under reduced pressure. The resultant residue was purified by a silica gel column chromatography (eluent: hexane-ethyl acetate=1:1), and further recrystallized from ethyl acetate-isopropyl ether to obtain the title compound as a colorless crystal (102 mg, yield: 21%). Melting point: 214–216° C.

Example 335
Synthesis of 2-[7-chloro-2-oxo-6-[(4-phenyl-1-piperazinyl)methyl]-4-(3-pyridinyl)-2H-chromen-3-yl]-N-[4-fluoro-2-(trifluoromethyl)phenyl]acetamide

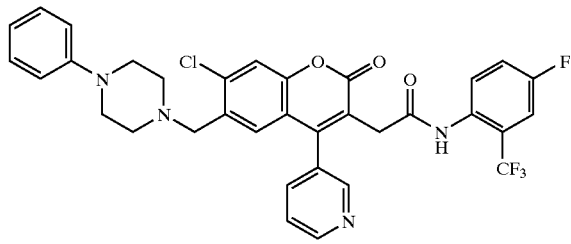

The title compound (yield: 21%) obtained by the method similar to that in Example 334. Melting point: 202–205° C. (ethyl acetate-isopropyl ether).

Example 336–337
The compounds of table 48 were obtained by the method similar to that in Example 308.

TABLE 48

| Example number | R | Yield (%) | Melting Point (° C.) (Recrystallization solvent) |
|---|---|---|---|
| 336 | Cl | 64 | 118 (decomp.) (AcOEt) |
| 337 | F | 39 | 193–196 (AcOEt) |

Example 338
Synthesis of ethyl 3-[3-[7-chloro-3-(2-[[4-chloro-2-(trifluoromethyl)phenyl]amino]-2-oxoethyl)-6-methyl-2-oxo-2H-chromen-4-yl]phenyl]-2-propionate

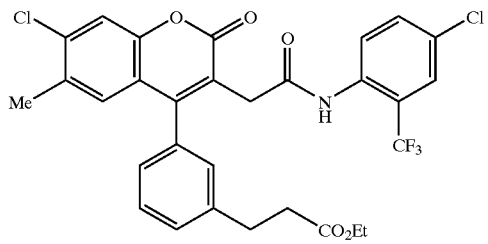

A mixture solution of ethyl (2E)-3-[3-[7-chloro-3-(2-[[4-chloro-2-(trifluoromethyl)phenyl]amino]-2-oxoethyl)-6-methyl-2-oxo-2H-chromen-4-yl]phenyl]-2-propenate (138 mg) in ethanol (5 ml) and THF (2 ml) was combined with Raney-nickel (approximately 100 mg), stirred under hydrogen atmosphere at room temperature for 4 hours. After the catalyst was filtered off using celite, the filtrate was concentrated. The resultant residue was purified by a silica gel chromatography (eluent: hexane-ethyl acetate=2:1), and recrystallized from ethyl acetate to obtain the title compound as a colorless crystal (131 mg, yield: 95%). Melting point: 116° C. (decomp.).

Example 339 to 340
The compounds of table 49 were obtained by the method similar to that in Example 309.

TABLE 49

| Example number | R | X | Yield (%) | Melting Point (° C.) (Recrystallization solvent) |
|---|---|---|---|---|
| 339 | F | CH=CH | 80 | 260–262 (AcOEt) |
| 340 | Cl | CH$_2$—CH$_2$ | 89 | 170–172 (AcOEt) |

In the Formulation Examples and Experiments described below, Compounds A, B and C are those shown below, respectively.

Compound A: 2-[6-chloro-2-oxo-4-(2-methylphenyl)-2H-chromen-3-yl]-N-(2,6-dimethoxyphenyl)acetamide;

Compound B: N-(2,6-dimethoxyphenyl)-N'-[3-(2-methylphenyl)-6,7-dihydro-5H-indeno[5,6-b]furan-2-yl]urea;

Compound C: N-(4-chloro-2-trifluoromethylphenyl)-2-(2-oxo-4-phenyl-2,6,7,8-tetrahydrocyclopenta[g]chromen-3-yl)acetamide.

Formulation Examples

A lipid-rich plaque regressing agent containing as an active ingredient a compound [I], [II], [III], [IV], [V] or [VI] or its salt of the present invention can be produced for example in the following formulations.

1. Capsule

| | |
|---|---|
| (1) Compound A | 10 mg |
| (2) Lactose | 90 mg |
| (3) Microcrystalline cellulose | 70 mg |
| (4) Magnesium stearate | 10 mg |
| 1 Capsule | 180 mg |

(1), (2) and (3) and ½ of (4) are mixed and granulated. To this, the remainder of (4) is added and the entire is encapsulated into a gelatin capsule.

2. Tablet

| | |
|---|---|
| (1) Compound A | 10 mg |
| (2) Lactose | 35 mg |
| (3) Corn starch | 150 mg |
| (4) Microcrystalline cellulose | 30 mg |
| (5) Magnesium stearate | 5 mg |
| 1 Tablet | 230 mg |

(1), (2), (3), ⅔ of (4) and ½ of (5) are mixed and granulated. To this granule, the remainder of (4) and (5) are added and compressed into a tablet.

3. Injection Formulation

| | | |
|---|---|---|
| (1) Compound A | 10 mg | |
| (2) Inositol | 100 mg | |
| (3) Benzyl alcohol | 20 mg | |
| 1 Ampoule | 130 mg | |

(1), (2) and (3) are dissolved in distlled water for injection to make the total volume 2 ml, and charged in an ampoule. All processes are conducted aseptically.

4. Capsule

| | |
|---|---|
| (1) Compound B | 10 mg |
| (2) Lactose | 90 mg |
| (3) Microcrystalline cellulose | 70 mg |
| (4) Magnesium stearate | 10 mg |
| 1 Capsule | 180 mg |

(1), (2) and (3) and ½ of (4) are mixed and granulated. To this, the remainder of (4) is added and the entire is encapsulated into a gelatin capsule.

5. Tablet

| | |
|---|---|
| (1) Compound B | 10 mg |
| (2) Lactose | 35 mg |
| (3) Corn starch | 150 mg |
| (4) Microcrystalline cellulose | 30 mg |
| (5) Magnesium stearate | 5 mg |
| 1 Tablet | 230 mg |

(1), (2), (3), ⅔ of (4) and ½ of (5) are mixed and granulated. To this granule, the remainder of (4) and (5) are added and compressed into a tablet.

6. Injection Formulation

| | |
|---|---|
| (1) Compound B | 10 mg |
| (2) Inositol | 100 mg |
| (3) Benzyl alcohol | 20 mg |
| 1 Ampoule | 130 mg |

(1), (2) and (3) are dissolved in distlled water for injection to make the total volume 2 ml, and charged in an ampoule. All processes are conducted aseptically.

7. Capsule

| | |
|---|---|
| (1) Compound C | 10 mg |
| (2) Lactose | 90 mg |
| (3) Microcrystalline cellulose | 70 mg |
| (4) Magnesium stearate | 10 mg |
| 1 Capsule | 180 mg |

(1), (2) and (3) and ½ of (4) are mixed and granulated. To this, the remainder of (4) is added and the entire is encapsulated into a gelatin capsule.

8. Tablet

| | |
|---|---|
| (1) Compound C | 10 mg |
| (2) Lactose | 35 mg |
| (3) Corn starch | 150 mg |
| (4) Microcrystalline cellulose | 30 mg |
| (5) Magnesium stearate | 5 mg |
| 1 Tablet | 230 mg |

(1), (2), (3), ⅔ of (4) and ½ of (5) are mixed and granulated. To this granule, the remainder of (4) and (5) are added and compressed into a tablet.

9. Injection Formulation

| | |
|---|---|
| (1) Compound C | 10 mg |
| (2) Inositol | 100 mg |
| (3) Benzyl alcohol | 20 mg |
| 1 Ampoule | 130 mg |

(1), (2) and (3) are dissolved in distlled water for injection to make the total volume 2 ml, and charged in an ampoule. All processes are conducted aseptically.

10. Capsule

| | |
|---|---|
| (1) Compound C | 10 mg |
| (2) Lactose | 90 mg |
| (3) Microcrystalline cellulose | 70 mg |
| (4) Magnesium stearate | 10 mg |
| 1 Capsule | 180 mg |

(1), (2) and (3) and ½ of (4) are mixed and granulated. To this, the remainder of (4) is added and the entire is encapsulated into a gelatin capsule.

11. Tablet

| | |
|---|---|
| (1) Compound C | 10 mg |
| (2) Lactose | 35 mg |
| (3) Corn starch | 150 mg |
| (4) Microcrystalline cellulose | 30 mg |
| (5) Magnesium stearate | 5 mg |
| 1 Tablet | 230 mg |

(1), (2), (3), ⅔ of (4) and ½ of (5) are mixed and granulated. To this granule, the remainder of (4) and (5) are added and compressed into a tablet.

12. Capsule

| | |
|---|---|
| (1) Compound C | 10 mg |
| (2) Lactose | 90 mg |
| (3) Microcrystalline cellulose | 70 mg |
| (4) Magnesium stearate | 10 mg |
| 1 Capsule | 180 mg |

(1), (2) and (3) and ½ of (4) are mixed and granulated. To this, the remainder of (4) is added and the entire is encapsulated into a gelatin capsule.

13. Tablet

| | |
|---|---|
| (1) Compound B | 10 mg |
| (2) Lactose | 35 mg |
| (3) Corn starch | 150 mg |
| (4) Microcrystalline cellulose | 30 mg |
| (5) Magnesium stearate | 5 mg |
| 1 Tablet | 230 mg |

(1), (2), (3), ⅔ of (4) and ½ of (5) are mixed and granulated. To this granule, the remainder of (4) and (5) are added and compressed into a tablet.

14. Capsule

| | |
|---|---|
| (1) Compound B | 10 mg |
| (2) Lactose | 90 mg |
| (3) Microcrystalline cellulose | 70 mg |
| (4) Magnesium stearate | 10 mg |
| 1 Capsule | 180 mg |

(1), (2) and (3) and ½ of (4) are mixed and granulated. To this, the remainder of (4) is added and the entire is encapsulated into a gelatin capsule.

15. Tablet

| | |
|---|---|
| (1) Compound A | 10 mg |
| (2) Lactose | 35 mg |
| (3) Corn starch | 150 mg |
| (4) Microcrystalline cellulose | 30 mg |
| (5) Magnesium stearate | 5 mg |
| 1 Tablet | 230 mg |

(1), (2), (3), ⅔ of (4) and ½ of (5) are mixed and granulated. To this granule, the remainder of (4) and (5) are added and compressed into a tablet.

16. Tablet

According to the formulation indicated below, a mixture of 175 g of Compound C, 175 g of D-mannitol, 118.65 g of corn starch and 105 g of croscarmellose sodium is mixed thoroughly using a vertical granulator (Model FM-VG-10, Powrex), and then kneaded with an aqueous solution in which 19.25 g of hydroxypropyl cellulose is dissolved (kneading condition: 400 rpm, 10 minutes). After drying the kneaded white material in a fluidized drier (FD-3S, Powrex) at the blowing temperature of 60° C. for 30 minutes, the material is sieved through a 1.5 mmϕ punching screen using a power mill (model P-3S, SHOWAKAGAKU KIKAI KOSAKUSHO). 525.14 g of this granule, 31 g of croscarmellose sodium and 1.86 g of magnesium stearate are added, and mixed in a mixer (model TM-15, SHOWAKAGAKU KIKAI KOSAKUSHO) for 5 minutes to obtain a granule for tablet compaction. This granule is compressed in 180 mg aliquots by a tabletting machine (Correct 19K, KIKUSUI SEISAKUSHO) using a 8.0 mmϕ edged plain mallet under 0.7 ton/cm2, whereby obtaining 2,350 tablets.

| | |
|---|---|
| Compound C | 50 mg |
| D-Mannitol | 50 mg |
| Corn starch | 33.9 mg |
| Croscarmellose sodium | 40 mg |
| Hydroxypropyl cellulose | 5.5 mg |
| Magnesium stearate | 0.6 mg |
| Total | 180.0 mg (per tablet) |

17. Solid Dispersion A

| | |
|---|---|
| Compound of Example 75 | 0.4 g |
| Hydroxypropylmethyl cellulose phthalate | 1.4 g |
| Lactose | 0.2 g |
| Total | 2.0 g |

The compound of Example 75 (0.4 g) was dissolved in methylene chloride (24 ml) and ethanol (16 ml), to which hydroxypropylmethyl cellulose phthalate (HP-50, SHINETSUKAGAKU, 1.4 g) was added and dissolved. To this solution, lactose (0.2 g) was added and suspended uniformly, and then the organic solvent was distilled off using a spray drier (YAMATO KAGAKU). The product was dried under reduced pressure using a vacuum drier for 14 hours to obtain a solid dispersion (1.4 g) of the compound of Example 75.

18. Solid Dispersion B

| | |
|---|---|
| Compound of Example 75 | 0.6 g |
| Hydroxypropylmethyl cellulose phthalate | 1.2 g |
| Lactose | 0.2 g |
| Total | 2.0 g |

The compound of Example 75 (0.6 g) was dissolved in methylene chloride (24 ml) and ethanol (16 ml), to which hydroxypropylmethyl cellulose phthalate (HP-50, SHINETSUKAGAKU, 1.2 g) was added and dissolved. To this solution, lactose (0.2 g) was added and suspended uniformly, and then the organic solvent was distilled off using a spray drier (YAMATO KAGAKU). The product was dried under reduced pressure using a vacuum drier for 14 hours to obtain a solid dispersion (1.4 g) of the compound of Example 75.

19. Tablet

| | |
|---|---|
| (1) Solid dispersion A | 50 mg |
| (2) Lactose | 34 mg |
| (3) Corn starch | 10.6 mg |
| (4) Corn starch (gelatinized) | 5 mg |
| (5) Magnesium stearate | 0.4 mg |
| (6) Calcium carboxymethyl cellulose | 20 mg |
| Total | 120 mg |

According to an ordinary method, (1) to (6) were mixed and compressed into a tablet using a tabletting machine. Using Solid dispersion B instead of Solid dispersion A, a tablet was also obtained.

Experiments

The lipid-rich plaque regressing effect of a compound [I], [II], [III], [IV], [V] or [VI] or its salt of the present invention is discussed below with referring to Experiments.

Experiment 1

[Method] A 5-week old male apo-lipoprotein E deficient mouse which exhibits a vascular lesion similar to a human arteriosclerotic lesion (hereinafter referred to as male apoE mouse) was maintained with an arteriosclerotic diet which was a CE-2 diet (normal diet, NIPPON CLEA) supplemented with 1.25% cholesterol for 8 weeks. Subsequently, each of only CE-2 powder, which is a normal diet, (control group, number of animals=8) and CE-2 powder supplemented with Compound A (number of animals=8) was given ad libitum during the period from the 9th week to the 12th week. Each animal was sacrificed by decapitation 12 weeks after initiation of the experiment, the vessel from the aortic arch to the femoral bifurcation was isolated and opened in the direction of the vascular axis, stained with oil red O (Sigma Aldrich Japan), photographed closely using a medical Nikkor (NIKON), and the photograph was scanned using a scanner (GT-6000, EPSON) and the image was processed using Adobe Photoshop. Thus, the image of the vessel was trimmed and the red color was extracted and modified into a two-tone gradation.

The two-tone image was subjected to an NIH image (National Institute of Health) to count pixels, whereby calculating the % lesion area based on the entire surface area of the internal wall of the vessel.

[Results] The lesion (plaque) area based on the vascular internal surface area was 31% in the group fed only the normal diet after 9th week. On the contrary, the administraiton of Compound A mixed with the normal diet at the dose of 27 mg/kg/day resulted in a marked reduction in the vascular lesion area to 15%, showing a significant ($p<0.01$, student's test) plaque regressing effect.

Experiment 2

[Method] A 6-week old male apo-lipoprotein E deficient mouse exhibiting a vascular lesion similar to a human arteriosclerotic lesion (hereinafter referred to as male apoE KO mouse) was maintained with an arteriosclerotic diet which was a CE-2 diet (normal diet, NIPPON CLEA) supplemented with 1.25% cholesterol for 8 weeks. Subsequently, from the 9th week to the 12th week, Compound B (0.5% methyl cellulose suspension: at 30 mg/kg/day) was administered orally, during the period only CE-2 powder, which is a normal diet, was given. The control group was maintained with only CE-2 diet. Each animal was sacrificed by decapitation 12 weeks after initiation of the experiment, the vessel from the aortic arch to the femoral bifurcation was isolated and opened in the direction of the vascular axis, stained with oil red O (Sigma Aldrich Japan), and subjected to an image analysis similarly to Experiment 1 to calculate the % lesion area based on the entire vascular internal wall area. The vessel specimen after the image analysis was homogenized in saline, and the amount of cholesteryl ester content in the aorta was measured in accordance with the method by Hara and Radin (Lipid Extract of tissues with a low-Toxicity solvent, Anal. Biochem., 90:420–426, 1978), that is, from the aorta stained with the oil red O was extracted the lipid by a glass homogenizer with hexane:isopropyl alcohol (3:2) and centrifuged. Subsequently, the supernatant was recovered and evaporated to dryness, and then dissolved in TESIT: dioxane (1:1). From this solution, its total cholesterol content (Cholesterol C test, WAKO) and the free cholesterol content (Free Cholesterol C test, WAKO) were examined. The data obtained were corrected for the wet weight of the aorta. The cholesteryl ester content (CE) was obtained by subtracting the free cholesterol content from the total cholesterol content. Since the sample, which was extracted with hexane:isopropyl alcohol and then evaporated to dryness, contained the oil red O which interferes with the absorption wavelength for the cholesterol measurement, the cholesterol content was calculated for each sample by subtracting the blank level (absorbance of oil red O in sample).

[Results] The results are shown in Table 50.

TABLE 50

| | Control group (n = 8) | Compound B group (n = 4) |
|---|---|---|
| % Lesion area | 22.6 ± 3.0 | 16.9 ± 1.6 |
| Aortic cholesteryl Ester content (μg/mg) | 9.42 ± 0.66 | 4.76 ± 0.46** | n: Number of animals,
**: $P < 0.05\%$ (Dunnett's test)

After maintaining apoE KO mice with the arteriosclerotic diet for 8 weeks followed by the normal diet for 4 weeks, the % lesion area was 22.6% and the aortic cholesteryl ester content was 9.42 μg/ml (control group). On the other hand, the arteriosclerotic diet for 8 weeks followed by the normal diet with 30 mg/kg/day of Compound B given by oral administraiton for 4 weeks resulted in the marked reduction of the lesion area to 16.9% and the aortic cholesteryl ester content to 4.76 μg/ml, which shows a plaque regressing effect.

Experiment 3

[Method] A 6-week old male apo-lipbprotein E deficient mouse exhibiting a vascular lesion similar to a human arteriosclerotic lesion (hereinafter referred to as male apoE KO mouse) was maintained with an arteriosclerotic diet which was a CE-2 diet (normal diet, NIPPON CLEA) supplemented with 1.25% cholesterol for 8 weeks. Subsequently, during the period from the 9th week to the 12th week, and Compound C (0.5% methyl cellulose suspension: at 10 mg/kg/day) was administered orally only, during the period only CE-2 powder, which is a normal diet, was given. The control group was maintained with only CE-2 diet. Each animal was sacrificed by decapitation 12 weeks after initiation of the experiment, the vessel from the aortic arch to the femoral bifurcation was isolated and opened in the direction of the vascular axis, stained with oil red O (Sigma Aldrich Japan), and subjected to an image analysis similarly to Experiment 1 to calculate the % lesion area based on the entire vascular internal wall area. The vessel specimen after the image analysis was homogenized in saline, and the amount of cholesteryl ester content in the aorta was measured by an enzymatic method similarly to Experiment 2 described above.

[Results] The results are shown in Table 51.

TABLE 51

| | Control group (n = 10) | Compound B group (n = 10) |
|---|---|---|
| % Lesion area | 31.2 ± 1.6 | 23.3 ± 1.8* |
| Aortic cholesteryl Ester content (μg/mg) | 6.83 ± 0.42 | 5.30 ± 0.37 | n: Number of animals
*$P < 0.05\%$ (Dunnett's test)

After maintaining apoE KO mice with the arteriosclerotic diet for 8 weeks followed by the normal diet for 4 weeks, the % lesion area was 31.2% and the aortic cholesteryl ester content was 6.83 μg/ml (control group). On the other hand, the arteriosclerotic diet for 8 weeks followed by the normal diet with 30 mg/kg/day of Compound C given by oral administraiton for 4 weeks resulted in the marked reduction of the lesion area to 23.3% and the aortic cholesteryl ester content to 5.30 µg/ml, which shows a plaque regressing effect.

INDUSTRIAL APPLICABILITY

Since the lipid-rich plaque regressing agent containing the compound [I], [II], [III], [IV], [V] or [VI], or their salts, or the prodrug thereof, of the present invention exhibits an excellent lipid-rich plaque regressing effect, they are useful in preventing and treating acute coronary artery syndrome such as acute myocardial infarction and unstable angina, peripheral artery occlusion and the like.

What is claimed is:

1. A compound selected from the group consisting of:
   (2E)-3-[3-[7-chloro-3-(2-[[4-chloro-2-(trifluoromethyl)phenyl]amino]-2-oxoethyl)-6-methyl-2-oxo-2H-chromen-4-yl]phenyl]propenoic acid;
   (2E)-3-[3-[7-chloro-3-(2-[4-fluoro-2-(trifluoromethyl)phenyl]amino]-2-oxoethyl)-6-methyl-2-oxo-2H-chromen-4-yl]phenyl]propenoic acid; and
   3-[3-[7-chloro-3-(2-[[4-chloro-2-(trifluorornethyl)phenyl]amino]-2-oxoethyl)-6-methyl-2-oxo-2H-chromen-4-yl]phenyl]propanoic acid, or a salt thereof.

2. A pharmaceutical composition comprising a compound according to claim 1 or a salt thereof, and a pharmaceutically acceptable carrier, excipient or diluent.

3. A method for regressing a lipid-rich plaque in a mammal in need thereof, comprising administering an effective amount of a compound according to claim 1 or a salt.

4. A method for treating acute coronary artery syndrome in a mammal in need thereof, comprising administering an effective amount of a compound of claim 1 or a salt thereof, to said mammal.

5. A method for treating acute myocardial infarction in a mammal in need thereof, comprising administering an effective amount of a compound of claim 1 or a salt thereof, to said mammal.

6. A method for treating unstable angina in a mammal in need thereof, comprising administering an effective amount of a compound of claim 1 or a salt thereof, to said mammal.

7. A method for treating peripheral artery occlusion in a mammal in need thereof, comprising administering an effective amount of a compound of claim 1 or a salt thereof, to said mammal.

* * * * *